US012752039B2

(12) United States Patent
Marmorstein et al.

(10) Patent No.: US 12,752,039 B2
(45) Date of Patent: Oct. 6, 2026

(54) FIBRIN HYDROGELS

(71) Applicant: Mayo Foundation for Medical Education and Research, Rochester, MN (US)

(72) Inventors: Alan D. Marmorstein, Rochester, MN (US); Jarel K. Gandhi, Modesto, CA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 368 days.

(21) Appl. No.: 18/036,787

(22) PCT Filed: Nov. 12, 2021

(86) PCT No.: PCT/US2021/059227
§ 371 (c)(1),
(2) Date: May 12, 2023

(87) PCT Pub. No.: WO2022/104128
PCT Pub. Date: May 19, 2022

(65) Prior Publication Data

US 2023/0414826 A1 Dec. 28, 2023

Related U.S. Application Data

(60) Provisional application No. 63/113,468, filed on Nov. 13, 2020.

(51) Int. Cl.
*A61L 24/00* (2006.01)
*A61L 24/10* (2006.01)

(52) U.S. Cl.
CPC ......... *A61L 24/0031* (2013.01); *A61L 24/106* (2013.01); *A61L 2300/442* (2013.01)

(58) Field of Classification Search
CPC ............... A61L 24/0031; A61L 24/106; A61L 2300/442
See application file for complete search history.

(56) References Cited

U.S. PATENT DOCUMENTS

| | | | | |
|---|---|---|---|---|
| 2019/0388579 | A1 | 12/2019 | Macphee et al. | |
| 2020/0061246 | A1 | 2/2020 | Marmorstein et al. | |
| 2020/0157497 | A1 | 5/2020 | Marmorstein et al. | |
| 2021/0213162 | A1* | 7/2021 | Brüggemann ....... | A61K 38/363 |

FOREIGN PATENT DOCUMENTS

| | | | |
|---|---|---|---|
| MD | 1425 Y | | 3/2020 |
| WO | WO 2001/093870 | | 12/2001 |
| WO | WO 2018/106414 | * | 6/2018 |
| WO | WO 2018/226648 | | 12/2018 |
| WO | WO 2020/017444 | | 1/2020 |
| WO | WO 2020/121290 | | 6/2020 |

OTHER PUBLICATIONS

Yao et al. (contrast Med. Mol. (2018) 22.*
AccessData.FDA.gov [online], "Drug Approval Package: VisionBlue (Trypan Blue) NDA #021670," approved on Dec. 16, 2004, retrieved on Jan. 2, 2024, retrieved from URL<https://www.accessdata.fda.gov/drugsatfda_docs/nda/2004/21-670_VisionBlue.cfm>, 2 pages.
AccessData.FDA.gov [online], "Drugs@FDA: FDA-Approved Drugs," available no later than Oct. 8, 2020, retrieved on Jan. 2, 2024, retrieved from URL<https://www.accessdata.fda.gov/scripts/cder/daf/index.cfm?event=overview.process&ApplNo=008041>, 1 page.
Ahmed et al., "Fibrin: a versatile scaffold for tissue engineering applications," Tissue Eng. Part B Rev., Jun. 2008, 14(2):199-215.
Avelar-Freitas et al., "Trypan blue exclusion assay by flow cytometry," Braz. J. Med. Biol. Res., Apr. 2014, 47(4):307-315.
Bacakova et al., "The potential applications of fibrin-coated electrospun polylactide nanofibers in skin tissue engineering," Int. J. Nanomedicine, Feb. 2016, 11:771-789.
Bateman et al., "The Effect of Thrombin Concentration on Fibrin Clot Structure Imaged by Multiphoton Microscopy and Quantified by Fractal Analysis," Microscopy and Microanalysis, Aug. 2005, 11(Suppl. 2):1018-1019.
Clauss, "[Rapid coagulation method for determination of fibrinogen]," Acta Haematol., 1957, 17(4):237-246 (with machine translation), 20 pages.
DailyMed.nlm.nih.gov [online], "Visionblue—trypan blue injection, solution," revised Dec. 2012, retrieved on Jan. 2, 2024, retrieved from URL<https://dailymed.nlm.nih.gov/dailymed/fda/fdaDrugXsl.cfm?setid=a44bc2ef-3d7f-4125-a7f7-c5969b1b4142&type=display>, 12 pages.
Edsall et al., "Effects of ions and neutral molecules on fibrin clotting," J. Biol. Chem., Aug. 1951, 191(2):735-756.
Extended European Search Report in European Appln. No. 21892920.6, dated Apr. 2, 2024, 21 pages.
Gandhi et al., "Alteration of fibrin hydrogel gelation and degradation kinetics through addition of azo dyes," J. Biomed. Mater. Res. A, Nov. 2021, 109(11):2357-2368.
Gandhi et al., "Enhanced Viability of Endothelial Colony Forming Cells in Fibrin Microbeads for Sensor Vascularization," Sensors (Basel.), Sep. 2015, 15(9):23886-23902.
Gandhi et al., "Fibrin hydrogels are safe, degradable scaffolds for sub-retinal implantation," PLoS One, Jan. 2020, 15(1):e0227641.
Gandhi et al., "Fibrin hydrogels as a xenofree and rapidly degradable support for transplantation of retinal pigment epithelium monolayers," Acta Biomater., Feb. 2018, 67:134-146.
Gandhi et al., "Human Fibrinogen for Maintenance and Differentiation of Induced Pluripotent Stem Cells in Two Dimensions and Three Dimensions," Stem Cells Transl. Med., Jun. 2019, 8(6):512-521.

(Continued)

*Primary Examiner* — Shirley V Gembeh
(74) *Attorney, Agent, or Firm* — Fish & Richardson P.C.

(57) ABSTRACT

This document provides fibrin hydrogels and methods and materials for making and using fibrin hydrogels. For example, this document provides fibrin hydrogels containing trypan blue (TB), Evans blue (EB), and/or one or more isomers thereof. Methods for making and using fibrin hydrogels containing TB, EB, and/or one or more isomers thereof also are provided.

12 Claims, 26 Drawing Sheets

(56) References Cited

OTHER PUBLICATIONS

Gandhi et al., "Perfusion Bioreactor Culture of Bone Marrow Stromal Cells Enhances Cranial Defect Regeneration," Plast. Reconstr. Surg., May 2019, 143(5):993e-1002e.
GenBank Accession No. AAGW02037995.1, "Oryctolagus cuniculus breed Thorbecke inbred cont2.37994, whole genome shotgun sequence," Aug. 31, 2009, 53 pages.
GenBank Accession No. AF080065.1, "Oryctolagus cuniculus prothrombin precursor, mRNA, partial cds," Jul. 25, 2016, 1 page.
GenBank Accession No. BD189695.1, "WO 2003004641-A/11: A method for preparing recombinant human thrombin," Aug. 5, 2014, 2 pages.
GenBank Accession No. M64982.1, "Human fibrinogen alpha chain gene, complete mRNAs," Mar. 30, 1994, 5 pages.
GenBank Accession No. M64983.1, "*Homo sapiens* fibrinogen beta chain (FGB), complete cds," May 18, 2000, 4 pages.
GenBank Accession No. X51473.1, "Human mRNA for fibrinogen gamma chain (partial)," Jul. 25, 2016, 2 pages.
Gissel et al., "Effects of an acidic environment on coagulation dynamics," J. Thromb. Haemost., Oct. 2016, 14(10):2001-2010.
International Search Report and Written Opinion in International Appln. No. PCT/US2021/059227, mailed on Mar. 29, 2022, 15 pages.
Jagusiak et al. "Amyloids, Congo red and the apple-green effect" Acta Biochimica Polonica., Mar. 2019, 66:39-46.
Jhanji et al., "Trypan blue dye for anterior segment surgeries," Eye (Lond.), Sep. 2011, 25(9):1113-1120.
Kaibara et al., "Effect of temperature on dynamic viscoelasticity during the clotting reaction of fibrin," Biochim. Biophys. Acta, Oct. 1977, 499(3):352-361.
Kheirkhah et al., "Inadvertent vitreous staining with trypan blue in pseudoexfoliation syndrome," Arch. Ophthalmol., Oct. 2010, 128(10):1372-1373.
Kurniawan et al., "Buffers Strongly Modulate Fibrin Self-Assembly into Fibrous Networks," Langmuir, Jun. 2017, 33(25):6342-6352.
Lee et al., "Multi-layered culture of human skin fibroblasts and keratinocytes through three-dimensional freeform fabrication," Biomaterials, Mar. 2009, 30(8):1587-1595.
Mishra et al., "Effect of prevascularization on in vivo vascularization of poly(propylene fumarate)/fibrin scaffolds," Biomaterials, Jan. 2016, 77:255-266.
Moreno-Arotzena et al., "Characterization of Fibrin and Collagen Gels for Engineering Wound Healing Models," Materials (Basel.), Apr. 2015, 8(4):1636-1651.
Moya et al., "Microfluidic Device to Culture 3D In Vitro Human Capillary Networks," Methods Mol. Biol., 2014, 1202:21-27.
Murphy et al., "Engineering fibrin hydrogels to promote the wound healing potential of mesenchymal stem cell spheroids," Acta Biomater., Dec. 2017, 64:176-186.
PubChem.com [online], "Evans blue," CID 9409, Jul. 2005, retrieved on Jan. 2, 2024, retrieved from URL<https://pubchem.ncbi.nlm.nih.gov/compound/9409>, 36 pages.
PubChem.com [online], "Trypan blue," CID 6296, Jul. 2005, retrieved on Jan. 2, 2024, retrieved from URL<https://pubchem.ncbi.nlm.nih.gov/compound/6296>, 77 pages.
Sierra, "Fibrin sealant adhesive systems: a review of their chemistry, material properties and clinical applications," J. Biomater. Appl., Apr. 1993, 7(4):309-352.
Spotnitz, "Fibrin Sealant: The Only Approved Hemostat, Sealant, and Adhesive—a Laboratory and Clinical Perspective," ISRN Surg., Mar. 2014, 2014: 203943, 28 pages.
Veckeneer et al., "Ocular toxicity study of trypan blue injected into the vitreous cavity of rabbit eyes," Graefes Arch Clin Exp Ophthalmol, Sep. 2001, 239(9):698-704.
Wang et al., "Fibrin Hydrogels for Endothelialized Liver Tissue Engineering with a Predesigned Vascular Network," Polymers (Basel.), Sep. 2018, 10(10):1048.
Wedgwood et al., "Rheological and Turbidity Study of Fibrin Hydrogels," Macromolecular Symposia, Dec. 2013, 334(1):117-125.
Weisel et al., "Fibrin Formation, Structure and Properties," Subcell. Biochem., 2017, 82:405-456.
Whelihan et al., "Thrombin generation and fibrin clot formation under hypothermic conditions: an in vitro evaluation of tissue factor initiated whole blood coagulation," J. Crit. Care, Feb. 2014, 29(1):24-30.
Xiao et al., "Evans Blue Inhibits HBV Replication Through a Dual Antiviral Mechanism by Targeting Virus Binding and Capsid Assembly," Front. Microbiol., Nov. 2019, 10:2638.
Office Action in JP Appln. No. 2023-528214, mailed on Jan. 6, 2026, 10 pages, with English Translation.
Redl et al., "Methods of Fibrin Seal Application," Thorac. Cardiovasc. Surgeon, 1982, 30:223-227.

* cited by examiner

Trypan Blue

Evans Blue

Trypan Blue
Evans Blue
Polyethylene Glycol
Sodium Fluorescein
Bismarck Brown R
Sodium Benzene Sulfonate
Congo Red
Alcian Blue
Brilliant Blue R
Indocyanine Green

FIBRIN HYDROGELS

CROSS-REFERENCE TO RELATED APPLICATIONS

This application is a National Stage application under 35 U.S.C. § 371 of International Application No. PCT/US2021/059227, having an International Filing Date of Nov. 12, 2021, which claims the benefit of U.S. Patent Application Ser. No. 63/113,468, filed on Nov. 13, 2020. The disclosures of the prior applications are considered part of (and are incorporated by reference in) the disclosure of this application.

BACKGROUND

1. Technical Field

This document relates to methods and materials for making and using fibrin hydrogels.

2. Background Information

Fibrin is an insoluble biological polymer formed through the activation of fibrinogen by the enzyme thrombin. Clinically fibrin has been used as tissue glue for decades, and, more recently, fibrin hydrogels have been used for a variety of tissue engineering applications (see, e.g., Ahmed et al., *Tissue Engineering Part B: Reviews,* 14:199-215 (2008)). The generation of high mechanical strength fibrin hydrogels in the laboratory can be facilitated by higher fibrin concentrations in tissue glues, but is limited by the rapid polymerization of fibrin at higher fibrinogen concentrations. As such, production of large or shaped higher mechanical strength fibrin hydrogels is difficult.

SUMMARY

This document provides methods and materials for making and using fibrin hydrogels. For example, this document provides fibrin hydrogels containing trypan blue (TB), Evans blue (EB), and/or one or more isomers thereof. In some cases, this document provides fibrin hydrogels containing a compound of Formula (I):

(I)

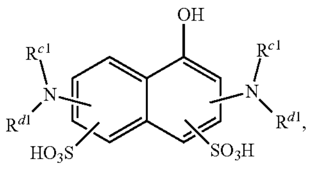

or a pharmaceutically acceptable salt thereof, wherein $R^{c1}$ and $R^{d1}$ are each independently selected from H and $C_{1-3}$ alkyl, or $R^{c1}$ and $R^{d1}$, together with the N atom to which they are attached form a group of formula:

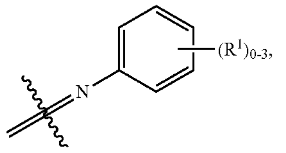

wherein each $R^1$ is independently selected from $C_{1-3}$ alkyl and $C_{1-3}$ alkoxy. For example, this document provides fibrin hydrogels containing a compound of Formula (II):

(II)

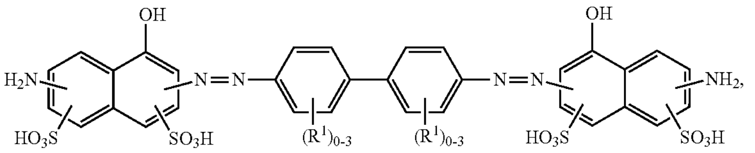

or a pharmaceutically acceptable salt thereof, wherein each $R^1$ is independently selected from $C_{1-3}$ alkyl and $C_{1-3}$ alkoxy. In some cases, a composition having a compound of Formula (II) or Formula (II) can include trypan blue (TB), Evans blue (EB), and/or one or more isomers thereof. This document also provides methods for making and using fibrin hydrogels containing TB, EB, and/or one or more isomers thereof. In some cases, this document provides methods for making and using fibrin hydrogels containing a compound of Formula (I) or Formula (II) such as TB, EB, and/or one or more isomers thereof.

As demonstrated herein, the inclusion of TB and/or EB in the gelation mix of fibrin gels slowed initial gelation without extending final gelation time, resulting in more uniform gels. For example, TB and/or EB can be used to increase the gelation time of fibrin hydrogels without negatively altering the final polymerization time or the shear modulus. Thus, the addition of TB and/or EB during thrombin mediated fibrin polymerization provides a unique and unrealized opportunity to improve the handling time of fibrin manufacture, thereby enabling the generation of high concentration, high strength, fibrin hydrogels for a variety of uses (e.g., for cell scaffolding applications at commercial scale). The increased handling time also can allow for the production of high mechanical strength fibrin gels having particular characteristics (e.g., particular topology) such as size, shape, and smoothness.

In general, one aspect of this document features fibrin hydrogels including (a) a fibrinogen polypeptide, (b) a thrombin polypeptide, and (c) Trypan Blue or an isomer thereof. The fibrin hydrogel can include Trypan Blue. The fibrin hydrogel can include an isomer of Trypan Blue. The fibrin hydrogel can include from about 10 mg/mL to about 60 mg/mL of the fibrinogen polypeptide (e.g., about 40 mg/mL of the fibrinogen polypeptide). The fibrin hydrogel can include from about 0.1 U/mL to about 1200 U/mL of the thrombin polypeptide (e.g., about 33 U/mL of the thrombin polypeptide). The fibrin hydrogel can include from about 0.0001% (w/w) to about 0.5% (w/w) of the Trypan Blue (e.g., about 0.15% (w/w) of the Trypan Blue). The polymerization time of the fibrin can be is from about 2 seconds to about 1200 seconds. The fibrin hydrogel can include fibrils having a diameter of from about 1 nanometer (nm) to about 400 nm. The fibrin hydrogel can include fibrils having a crosslinking density of from about 1 crosslink/μm$^2$ to about 5,000 crosslinks/μm$^2$. The fibrin hydrogel can have a shear modulus of from about 1900 Pa to about 2420 Pa. The surface area of the fibrin hydrogel can be from about 0.05 cm$^2$ to about 300 cm$^2$. The thickness of the fibrin hydrogel can be from about 0.1 μm to about 1,000 μm. The fibrin hydrogel can be made by injection molding.

In another aspect, this document features fibrin hydrogels including (a) a fibrinogen polypeptide, (b) a thrombin polypeptide, and (c) Evans Blue or an isomer thereof. The fibrin hydrogel can include Evans Blue. The fibrin hydrogel can include an isomer of Evans Blue. The fibrin hydrogel can include from about 10 mg/mL to about 60 mg/mL of the fibrinogen polypeptide (e.g., about 40 mg/mL of the fibrinogen polypeptide). The fibrin hydrogel can include from about 0.1 U/mL to about 1200 U/mL of the thrombin polypeptide (e.g., about 33 U/mL of the thrombin polypeptide). The fibrin hydrogel can include from about 0.0001% (w/w) to about 0.5% (w/w) of the Evans Blue (e.g., about 0.15% (w/w) of the Evans Blue). The polymerization time of the fibrin hydrogel can be from about 2 seconds to about 1200 seconds. The fibrin hydrogel can include fibrils having a diameter of from about 1 nm to about 400 nm. The fibrin hydrogel can include fibrils having a crosslinking density of from about 1 crosslink/μm$^2$ to about 5,000 crosslinks/μm$^2$. The fibrin hydrogel can include a shear modulus of from about 1600 Pa to about 2520 Pa. The surface area of the fibrin hydrogel can be from about 0.05 cm$^2$ to about 300 cm$^2$. The thickness of the fibrin hydrogel can be from about 0.1 μm to about 1,000 μm. The fibrin hydrogel can be made by injection molding.

In another aspect, this document features a fibrin hydrogel including (a) greater than about 30 mg/mL of a fibrinogen polypeptide, and (b) a thrombin polypeptide; where the fibrin hydrogel comprises a shear modulus of from about 1900 Pa to about 2420 Pa. The fibrin hydrogel can include from about 30 mg/mL to about 60 mg/mL of the fibrinogen polypeptide (e.g., about 40 mg/mL of the fibrinogen polypeptide). The fibrin hydrogel can include from about 0.1 U/mL to about 1200 U/mL of the thrombin polypeptide (e.g., about 33 U/mL of the thrombin polypeptide). The can include Trypan Blue or an isomer thereof. The fibrin hydrogel can include from about 0.0001% (w/w) to about 0.5% (w/w) of the Trypan Blue or the isomer. The fibrin hydrogel can include Evans Blue or an isomer thereof. The fibrin hydrogel can include from about 0.0001% (w/w) to about 0.5% (w/w) of the Evans Blue or the isomer. The polymerization time of the fibrin hydrogel can be from about 2 seconds to about 1200 seconds. The fibrin hydrogel can include fibrils having a diameter of from about 1 nanometer (nm) to about 400 nm. The fibrin hydrogel can include fibrils having a crosslinking density of from about 1 crosslink/μm$^2$ to about 5,000 crosslinks/μm$^2$. The surface area of the fibrin hydrogel can be from about 0.05 cm$^2$ to about 300 cm$^2$. The thickness of the fibrin hydrogel can be from about 0.1 μm to about 1,000 μm. The fibrin hydrogel can be made by injection molding.

In another aspect, this document features a fibrin hydrogel including (a) greater than about 30 mg/mL of a fibrinogen polypeptide, and (b) a thrombin polypeptide; wherein the polymerization time of the fibrin hydrogel is from about 2 seconds to about 1200 seconds. The fibrin hydrogel can include from about 30 mg/mL to about 60 mg/mL of the fibrinogen polypeptide (e.g., about 40 mg/mL of the fibrinogen polypeptide). The fibrin hydrogel can include from about 0.1 U/mL to about 1200 U/mL of the thrombin polypeptide (e.g., about 33 U/mL of the thrombin polypeptide). The can include Trypan Blue or an isomer thereof. The fibrin hydrogel can include from about 0.0001% (w/w) to about 0.5% (w/w) of the Trypan Blue or the isomer. The fibrin hydrogel can include Evans Blue or an isomer thereof. The fibrin hydrogel can include from about 0.0001% (w/w) to about 0.5% (w/w) of the Evans Blue or the isomer. The fibrin hydrogel can have a shear modulus of from about 1900 Pa to about 2420 Pa. The fibrin hydrogel can include fibrils having a diameter of from about 1 nanometer (nm) to about 400 nm. The fibrin hydrogel can include fibrils having a crosslinking density of from about 1 crosslink/μm$^2$ to about 5,000 crosslinks/μm$^2$. The surface area of the fibrin hydrogel can be from about 0.05 cm$^2$ to about 300 cm$^2$. The thickness of the fibrin hydrogel can be from about 0.1 μm to about 1,000 μm. The fibrin hydrogel can be made by injection molding.

In another aspect, this document features a fibrin hydrogel including (a) a fibrinogen polypeptide; (b) a thrombin polypeptide; and (c) a compound of Formula (I):

(I)

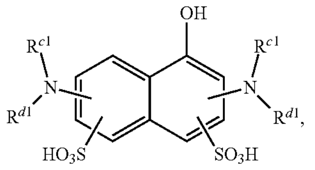

or a pharmaceutically acceptable salt thereof, where $R^{c1}$ and $R^{d1}$ are each independently selected from H and $C_{1-3}$ alkyl, or $R^{c1}$ and $R^{d1}$, together with the N atom to which they are attached form a group of formula:

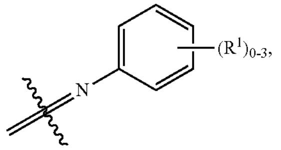

where each $R^1$ is independently selected from $C_{1-3}$ alkyl and $C_{1-3}$ alkoxy. The $R^{c1}$ and $R^{d1}$ can be each independently be selected from H and $C_{1-3}$ alkyl. The compound of Formula (I) can have the formula:

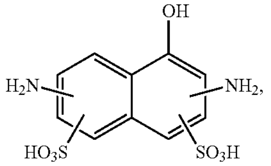

or a pharmaceutically acceptable salt thereof. The $R^{c1}$ and $R^{d1}$, together with the N atom to which they are attached can m a group of formula:

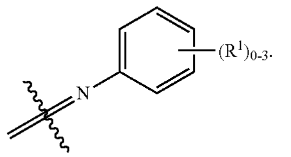

The $R^1$ can be $C_{1-3}$ alkyl. The $R^1$ can be $C_{1-3}$ alkoxy. The $R^{c1}$ and $R^{d1}$, together with the N atom to which they are attached can form a group of formula:

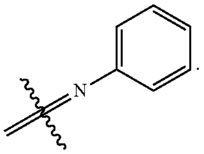 [SMILES: *=Nc1ccccc1]

The compound of Formula (I) can have the formula:

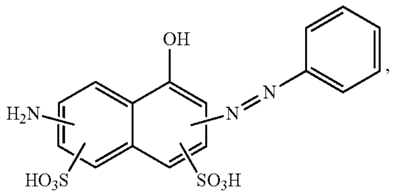

or a pharmaceutically acceptable salt thereof. The compound of Formula (I) can have the formula:

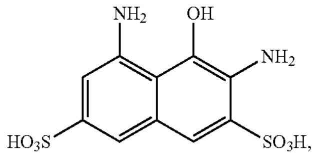

or a pharmaceutically acceptable salt thereof. The compound of Formula (I) can have the formula:

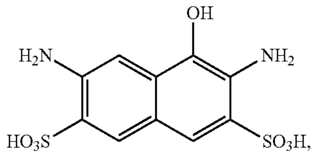

or a pharmaceutically acceptable salt thereof. The compound of Formula (I) can have the formula:

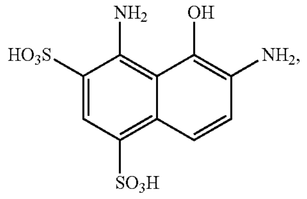 [SMILES: Nc1ccc2c(S(=O)(=O)O)cc(S(=O)(=O)O)c(N)c2c1O]

or a pharmaceutically acceptable salt thereof. The fibrin hydrogel can include from about 10 mg/mL to about 60 mg/mL of the fibrinogen polypeptide (e.g., about 40 mg/mL of the fibrinogen polypeptide). The fibrin hydrogel can include from about 0.1 U/mL to about 1200 U/mL of said thrombin polypeptide (e.g., about 33 U/mL of the thrombin polypeptide). The polymerization time of the fibrin hydrogel can be from about 2 seconds to about 1200 seconds. The fibrin hydrogel can include fibrils having a diameter of from about 1 nanometer (nm) to about 400 nm. The fibrin hydrogel can include fibrils having a crosslinking density of from about 1 crosslink/μm$^2$ to about 5,000 crosslinks/μm$^2$. The fibrin hydrogel can include a shear modulus of from about 1900 Pa to about 2420 Pa. The surface area of the fibrin hydrogel can be from about 0.05 cm$^2$ to about 300 cm$^2$. The thickness of the fibrin hydrogel can be from about 0.1 μm to about 1,000 μm. The fibrin hydrogel can be made by injection molding.

In another aspect, this document features a fibrin hydrogel including (a) a fibrinogen polypeptide; (b) a thrombin polypeptide; and (c) a compound of Formula (II):

(II)

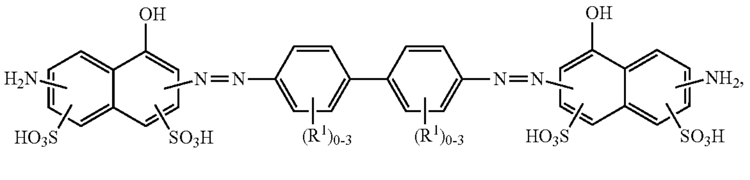

or a pharmaceutically acceptable salt thereof, where each $R^1$ can independently be selected from $C_{1-3}$ alkyl and $C_{1-3}$ alkoxy. The compound of Formula (II) can have the formula:

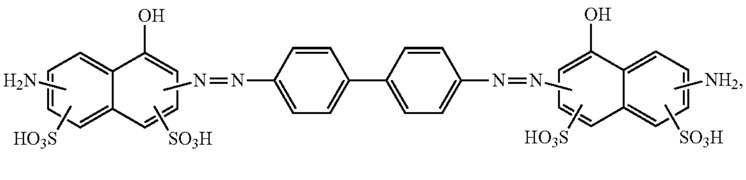

or a pharmaceutically acceptable salt thereof. The compound of Formula (II) can have the formula:

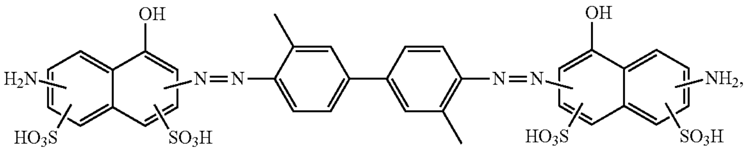

or a pharmaceutically acceptable salt thereof. The compound of Formula (II) can have the formula:

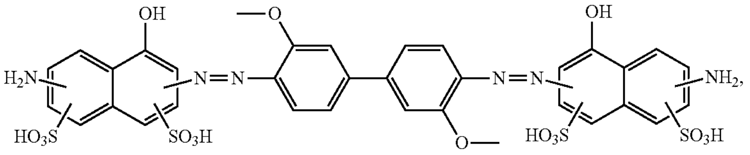

or a pharmaceutically acceptable salt thereof. The compound of Formula (II) can have the formula:

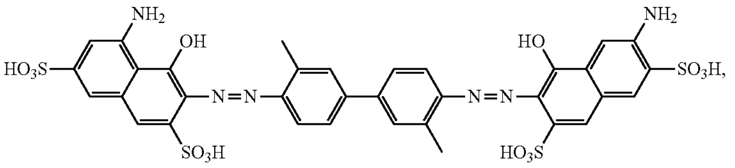 [SMILES: Cc1cc(-c2ccc(N=Nc3c(S(=O)(=O)O)cc4cc(S(=O)(=O)O)cc(N)c4c3O)c(C)c2)ccc1N=Nc1c(S(=O)(=O)O)cc2cc(S(=O)(=O)O)c(N)cc2c1O]

or a pharmaceutically acceptable salt thereof. The compound of Formula (II) can have the formula:

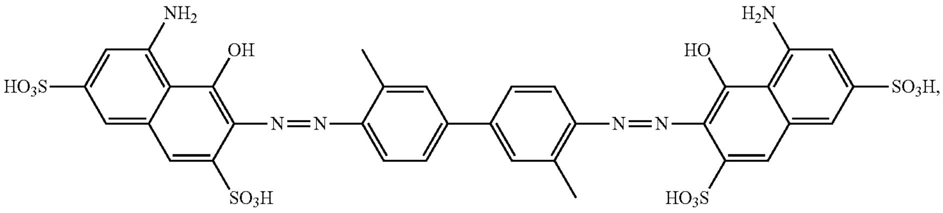 [SMILES: Cc1cc(-c2ccc(N=Nc3c(S(=O)(=O)O)cc4cc(S(=O)(=O)O)cc(N)c4c3O)c(C)c2)ccc1N=Nc1c(S(=O)(=O)O)cc2cc(S(=O)(=O)O)cc(N)c2c1O]

or a pharmaceutically acceptable salt thereof. The compound of Formula (II) can have the formula:

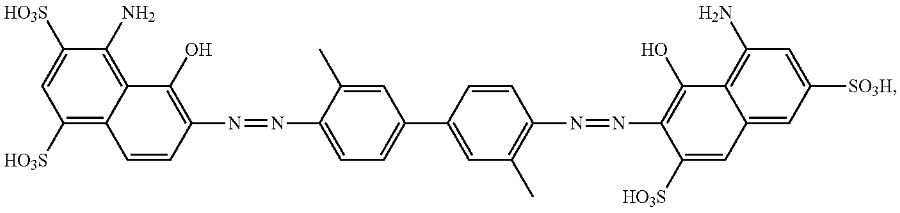 [SMILES: Cc1cc(-c2ccc(N=Nc3c(S(=O)(=O)O)cc4cc(S(=O)(=O)O)cc(N)c4c3O)c(C)c2)ccc1N=Nc1ccc2c(S(=O)(=O)O)cc(S(=O)(=O)O)c(N)c2c1O]

or a pharmaceutically acceptable salt thereof. The compound of Formula (II) can have the formula:

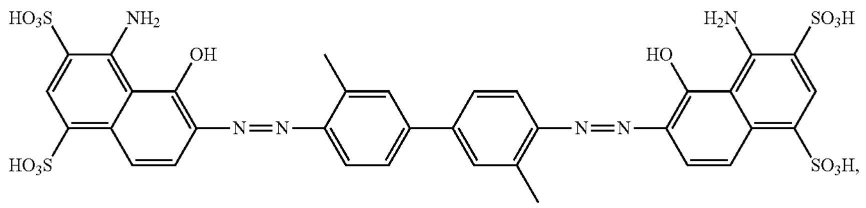 [SMILES: Cc1cc(-c2ccc(N=Nc3ccc4c(S(=O)(=O)O)cc(S(=O)(=O)O)c(N)c4c3O)c(C)c2)ccc1N=Nc1ccc2c(S(=O)(=O)O)cc(S(=O)(=O)O)c(N)c2c1O]

or a pharmaceutically acceptable salt thereof. The fibrin hydrogel can include from about 10 mg/mL to about 60 mg/mL of the fibrinogen polypeptide (e.g., about 40 mg/mL of the fibrinogen polypeptide). The fibrin hydrogel can include from about 0.1 U/mL to about 1200 U/mL of said thrombin polypeptide (e.g., about 33 U/mL of the thrombin polypeptide). The polymerization time of the fibrin hydrogel can be from about 2 seconds to about 1200 seconds. The fibrin hydrogel can include fibrils having a diameter of from about 1 nanometer (nm) to about 400 nm. The fibrin hydrogel can include fibrils having a crosslinking density of from about 1 crosslink/$\mu m^2$ to about 5,000 crosslinks/$\mu m^2$. The fibrin hydrogel can include a shear modulus of from about 1900 Pa to about 2420 Pa. The surface area of the fibrin hydrogel can be from about 0.05 $cm^2$ to about 300 $cm^2$. The thickness of the fibrin hydrogel can be from about 0.1 μm to about 1,000 μm. The fibrin hydrogel can be made by injection molding.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

(FIG. 3A) Graph of average clotting time of samples diluted in citrate buffer or citrate buffer with trypan blue (TB) added. Fibrinogen and thrombin was used from commercially available controls from the manufacturer. There is a statistical difference between the two groups ($n=10$, $p<0.001$). (FIG. 3B) Graph of average clotting time for the various chemical agent additives. Phosphate buffered saline (PBS), TB, Evans Blue (EB), Polyethylene Glycol (PEG), Sodium Fluorescein (SF), Brilliant Blue (BBr), Sodium Benzene Sulfonate (SBS). All dyes were used at a 4 mM concentration. A fixed 1:20 dilution of fibrinogen (Evicel) was used. The * indicates that the TB was statistically different from all other agents ($n=10$, $p<0.001$). EB yielded a clot time in excess of 70 seconds, beyond the detectable range of the instrument. Clot formation was verified within the cuvette after the experiment was run. (FIG. 3C) Photomicrographs of fibrin gels cast with PBS, TB, or EB. The PBS fibrin gel has highly variable opacities. The edges are stringy and not clearly defined. The TB and EB gels appear more homogeneous in construction, with defined edges and uniform surface texture. These gels were formed by briefly stirring the mixture solution.

(FIG. 4A) Graph of average clotting time at various concentrations of TB or EB. A fixed 1:20 dilution concentration of fibrinogen (Evicel) was used. EB appears to have a larger impact on clotting time than TB at the same dye concentration. (FIG. 4B) Graph of average clotting time at various fibrinogen concentrations with PBS, TB, or EB. A 0.4% w/v dye concentration was used. All 3 conditions confirmed the inverse relationship with fibrinogen concentration clotting time, as predicted by the Clauss Method. Fibrinogen concentration did not appear to alter the effect of the dye on clotting time.

(FIG. 5A) Graphs of modulus (g' and g") versus time of example fibrin gels made with 10 mg/mL fibrinogen, 1 U/mL thrombin, and 0.01% dye final concentration. The time window was adjusted to visualize the first instance in which g' exceeded g", the gelation time. The green arrow indicates the gelation time of that sample. (FIG. 5B) Graph of average gel times for the gels made with PBS, TB, EB or PEG. * indicates that TB and EB were both statistically different from all other groups ($n=3$, $p<0.001$).

(FIG. 7A) Graph of shear modulus versus time of example fibrin gels made with 40 mg/mL fibrinogen, 33 U/mL thrombin, and 0.12% dye final concentration. Both x and y axis are plotted as log base 10 to visualize the initial gelation kinetics. (FIG. 7B) Graph of the final polymerization time (fully set gel) for fibrin gels made with PBS, TB, EB, and PEG. There were no significant differences (p=0.65). (FIG. 7C) Graph of the gel time for fibrin gels made with 40 mg/mL fibrinogen, 33 U/mL thrombin, and 0.12% dye final concentration. TB and EB were statistically different (n=3. p=0.03). Gels made of PBS and PEG at these concentrations gelled prior to the first time point of 11 seconds and could not be accurately measured.

(FIG. 8A) Graph of shear modulus versus time of example fibrin gels made with 40 mg/mL fibrinogen, 33 U/mL thrombin, and 0.12% dye final concentration. (FIG. 8B) Graph of final shear modulus values for fibrin gels made with PBS, TB, EB, or PEG (n=3, p=0.08).

(FIG. 9A) Graph depicting the resultant time shift parameter, $x_c$, from modeling shear modulus data over time from fibrin gels formed with PBS, TB, EB or PEG. Data for g' versus time for each condition was modeled as a biexponential equation and is reported in Table 2. * indicates that TB and EB are significantly different (n=3, p<0.001) from all other groups. (FIG. 9B) Graph depicting the resultant ratio of reaction rates ($r_1/r_2$) from modeling shear modulus data over time from fibrin gels formed with PBS, TB, EB, or PEG. No statistical trend was achieved (n=3, p=0.057).

(FIG. 12A) Representative optical coherence tomography B-scan and en face view over time of an EB fibrin gel degraded with tissue plasminogen activator (tPA) and plasminogen (P). The fibrin gel was made with 40 mg/mL fibrinogen, 33 U/mL thrombin, 0.12% EB final concentrations using a custom polyoxymethylene (POM) mold. The degradation solution consisted of 1.6 U/mL P and 17,000 U/mL tPA in PBS at 37° C. (FIG. 12B) Representative graph of normalized fibrin gel thickness over time during degradation. (FIG. 12C) Graph showing the final degradation time for fibrin gels made of PBS, TB, and EB. There was no statistical difference (n=3, p=0.06), though it appears the EB gels took longer to completely degrade.

(FIG. 13A) Photomicrograph of a fibrin gel made with TB. The gel was made using a pressing method with a custom POM mold to create a ~200 μm thick sheet on the bottom of a 6 well cell culture plate. (FIG. 13B) Photomicrograph of induced pluripotent stem cell-derived retinal pigment epithelium (iPSC-RPE) cultured on a fibrin gel made with TB at 1 month. The fibrin gel appears clear even though the gel was cast using TB. (FIG. 13C) Photomicrograph of iPSC-RPE cultured on fibrin. RPE appear in their characteristic pigmented, hexagonal cobblestone monolayer phenotype. (FIG. 13D) Representative western blot analysis for B-actin (Beta-A), CRALBP (CRALB), MERTK, RPE65, and Best1 in iPSC-RPE cultured on fibrin hydrogels made with TB at 8 weeks.

(FIG. 14A) Schematic of a custom slide used to fabricate fibrin gels using injection molding technique. The total depth of the slide is ⅛" and the cavity has a depth of 0.008" (200 μm). The sprue hole (left) has a depth of 1/16" and the two air holes (right) have a depth of 1/32". (FIG. 14B) Representative slide fabricated by milling a sheet of polycarbonate. The gel/culture surface area is 15 $cm^2$.

(FIG. 17A) Photomicrograph of a slide lined up with a cover plate to visualize the sprue hole for injection molding the fibrin gels. (FIG. 17B) Photomicrograph of an aluminum holder with 5 slides lined up and fitted with cover plate to scale production. (FIG. 17C) Top view of the aluminum holder to visualize the sprue holes.

(FIG. 18A) Photomicrograph of a larger slide for scaled up production. The outer dimensions are 4"×4". The overall gel/culture surface area is 96 $cm^2$. (FIG. 18B) Photomicrograph of the larger slide fitted within a commercially available T150 flask for cell culture.

(FIG. 19A) Photomicrograph of cast fibrin gel. The slide is submerged in PBS within a 4 well rectangular plate. (FIG. 19B) Photomicrograph of iPSC-RPE cultured on fibrin gel slide for 1 month. RPE appear pigmented as phenotypically characteristic. The gel appears clear even though TB was used to cast the gel.

(FIG. 21A) Computer-aided drafting (CAD) image of an exemplary shield plate attached to a fibrin slide plate. (FIG. 21B). Top, bottom, and side views of an exemplary shield plate with a slide plate attached.

DETAILED DESCRIPTION

Figure 1:
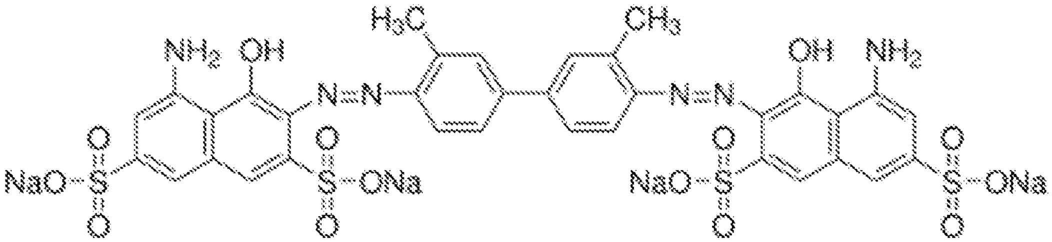
FIG. 1. Chemical structures of TB and EB.
Figure 1:
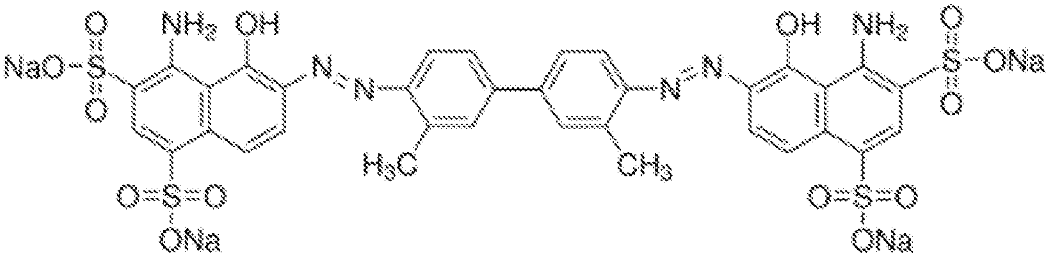

This document provides methods and materials for making and using fibrin hydrogels. For example, this document provides fibrin hydrogels containing TB, EB, and/or one or more isomers thereof. A fibrin hydrogel provided herein can include (a) one or more fibrinogen polypeptides, (b) one or more thrombin polypeptides, and (c) TB, EB, and/or one or more isomers thereof. In some cases, this document provides fibrin hydrogels containing TB, EB, and/or one or more isomers thereof. A fibrin hydrogel provided herein can include (a) one or more fibrinogen polypeptides, (b) one or more thrombin polypeptides, and (c) a compound of Formula (I):

(I)

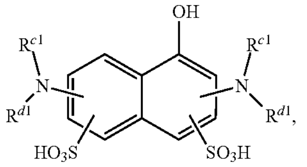

or a pharmaceutically acceptable salt thereof, wherein $R^{c1}$ and $R^{d1}$ are each independently selected from H and $C_{1-3}$ alkyl, or $R^{c1}$ and $R^{d1}$, together with the N atom to which they are attached form a group of formula:

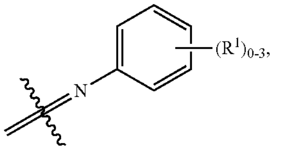

wherein each $R^1$ is independently selected from $C_{1-3}$ alkyl and $C_{1-3}$ alkoxy. For example, this document provides fibrin hydrogels containing a compound of Formula (II):

active fragment of a fibrinogen polypeptide (e.g., a truncated fibrinogen polypeptide or spliced fibrinogen polypeptide). For example a fibrinogen polypeptide can be an a chain polypeptide, a β chain polypeptide, and/or a γ chain polypeptide of the fibrinogen polypeptide. In some cases, a fibrinogen polypeptide can be obtained from (e.g., can be isolated from) one or more animals. For example, a fibrinogen polypeptide can be obtained from a fish (e.g., a salmon). For example, a fibrinogen polypeptide can be obtained from a mammal, such as a mammal to be treated using a fibrin hydrogel provided herein. Examples of fibrinogen polypeptides that can be included in a fibrin hydrogel provided herein (e.g., can be included in a gelation mixture for a fibrin hydrogel provided herein) include, without limitation, a Biologically Active Component 2 (e.g., EVICEL®), a Sealer Protein Concentrate (e.g. TISSEEL), a Vial 1 Fibrinogen Concentrate (e.g., BERIPLAST®), Fibrinogen Concentrate (e.g., BOLHEAL®), those set forth in the National Center for Biotechnology Information (NCBI) database at accession no. M64982 (version M64982.1), accession no. X51473 (version X51473.1), and accession no. M64983 (version M64983.1).

A fibrin hydrogel provided herein (e.g., a fibrin hydrogel including one or more fibrinogen polypeptides, one or more thrombin polypeptides, and TB, EB, and/or one or more isomers thereof) can include any amount of fibrinogen polypeptides (e.g., can include any amount of fibrinogen polypeptides within a gelation mixture prior to gelation of the fibrin hydrogel). In some cases, a fibrin hydrogel provided herein (e.g., a fibrin hydrogel including one or more fibrinogen polypeptides, one or more thrombin polypep- (II)

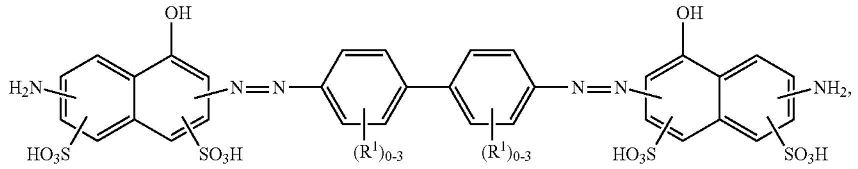

or a pharmaceutically acceptable salt thereof, wherein each $R^1$ is independently selected from $C_{1-3}$ alkyl and $C_{1-3}$ alkoxy. In some cases, a composition having a compound of Formula (II) can include TB, EB, and/or one or more isomers thereof. For example, a fibrin hydrogel can include a cross-linked network of fibrin formed by the polymerization of fibrin formed from fibrinogen polypeptides in the presence of thrombin polypeptides and TB, EB, and/or one or more isomers thereof.

A fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) any appropriate fibrinogen polypeptide(s). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) any appropriate fibrinogen polypeptide(s). In some cases, a fibrinogen polypeptide can be a synthetic polypeptide. In some cases, a fibrinogen polypeptide can be a recombinant polypeptide. In some cases, a fibrinogen polypeptide can be a biologically tides, and a compound of Formula (I) or Formula (II) such as TB, EB, and/or one or more isomers thereof) can include any amount of fibrinogen polypeptides (e.g., can include any amount of fibrinogen polypeptides within a gelation mixture prior to gelation of the fibrin hydrogel). In some cases, a fibrin hydrogel provided herein can include a fibrinogen polypeptide concentration that is greater than a fibrinogen polypeptide concentration typically found in plasma (e.g., in human plasma). For example, a gelation mixture for a fibrin hydrogel provided herein can include greater than about 5 milligrams fibrinogen polypeptides per milliliter of gelation mixture (mg/mL). In some cases, a fibrin hydrogel provided herein can include a fibrinogen polypeptide concentration that is greater than a fibrinogen polypeptide concentration typically found in fibrin glues (e.g., in a human fibrin glue). For example, a gelation mixture for a fibrin hydrogel provided herein can include greater than about 30 mg/mL fibrinogen polypeptides. In some cases, a fibrin hydrogel provided herein can include a fibrinogen concentration that is lower than a solubility concentration of saturated fibrinogen polypeptides solution concentration. For example, a gelation mixture for a fibrin hydrogel provided herein can include less than about 90 mg/mL fibrinogen polypeptides. In some cases, a fibrin hydrogel provided herein can include (e.g., can be formed from a gelation mixture including) from about 10 mg/mL to about 60 mg/mL fibrinogen polypeptides (e.g., from about 10 mg/mL to about 50 mg/mL, from about 10 mg/mL to about 40 mg/mL, from about 10 mg/mL to about 30 mg/mL, from about 10 mg/mL to about 20 mg/mL, from about 20 mg/mL to about 60 mg/mL, from about 30 mg/mL to about 60 mg/mL, from about 40 mg/mL to about 60 mg/mL, from about 50 mg/mL to about 60 mg/mL, from about 15 mg/mL to about 55 mg/mL, from about 20 mg/mL to about 50 mg/mL, from about 25 mg/mL to about 45 mg/mL, from about 30 mg/mL to about 40 mg/mL, from about 20 mg/mL to about 30 mg/mL, or from about 40 mg/mL to about 50 mg/mL fibrinogen polypeptides). For example, a gelation mixture for a fibrin hydrogel provided herein can include about 10 mg/mL fibrinogen polypeptides. For example, a gelation mixture for a fibrin hydrogel provided herein can include about 40 mg/mL fibrinogen polypeptides.

A fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) any appropriate thrombin polypeptide(s). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) any appropriate thrombin polypeptide(s). In some cases, a thrombin polypeptide can be a synthetic polypeptide. In some cases, a thrombin polypeptide can be a recombinant polypeptide. In some cases, a fibrinogen polypeptide can be a biologically active fragment of a thrombin polypeptide (e.g., an enzymatic domain of a thrombin polypeptide). In some cases, a thrombin polypeptide can be obtained from (e.g., can be isolated from) one or more animals, such as a mammal to be treated using a fibrin hydrogel provided herein. Examples of thrombin polypeptides that can be included in a fibrin hydrogel provided herein (e.g., can be included in a gelation mixture for a fibrin hydrogel provided herein) include, without limitation, Thrombin Vial (e.g., EVICEL®), Thrombin Solution (TISSEEL), Vial 3 Thrombin (BERIPLAST®), Thrombin Vial (e.g., BOLUHAL®), those set forth in the NCBI database at accession no. BD189695 (version BD189695.1), accession no. AAGW02037995 (version AAGW02037995.1), and accession no. AF080065 (version AF080065.1).

A fibrin hydrogel provided herein (e.g., a fibrin hydrogel including one or more fibrinogen polypeptides, one or more thrombin polypeptides, and TB, EB, and/or one or more isomers thereof) can include any amount of thrombin polypeptides (e.g., can include any amount of thrombin polypeptides within a gelation mixture prior to gelation of the fibrin hydrogel). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include any amount of thrombin polypeptides (e.g., can include any amount of thrombin polypeptides within a gelation mixture prior to gelation of the fibrin hydrogel). For example, a fibrin hydrogel provided herein can include (e.g., can be formed from a gelation mixture including) from about 0.1 unit thrombin polypeptides per mL of hydrogel (U/mL) to about 1200 U/mL thrombin polypeptides (e.g., from about 0.1 U/mL to about 1000 U/mL, from about 0.1 U/mL to about 800 U/mL, from about 0.1 U/mL to about 600 U/mL, from about 0.1 U/mL to about 400 U/mL, from about 0.1 U/mL to about 200 U/mL, from about 0.1 U/mL to about 100 U/mL, from about 0.1 U/mL to about 50 U/mL, from about 0.1 U/mL to about 25 U/mL, from about 0.1 U/mL to about 1 U/mL, from about 1 U/mL to about 1200 U/mL, from about 25 U/mL to about 1200 U/mL, from about 100 U/mL to about 1200 U/mL, from about 250 U/mL to about 1200 U/mL, from about 500 U/mL to about 1200 U/mL, from about 750 U/mL to about 1200 U/mL, from about 1 U/mL to about 1000 U/mL, from about 50 U/mL to about 750 U/mL, from about 100 U/mL to about 500 U/mL, from about 200 U/mL to about 300 U/mL, from about 0.5 U/mL to about 33 U/mL thrombin polypeptides, from about 1 U/mL to about 100 U/mL thrombin polypeptides, from about 10 U/mL to about 200 U/mL, from about 200 U/mL to about 400 U/mL, from about 300 U/mL to about 500 U/mL, from about 400 U/mL to about 600 U/mL, from about 500 U/mL to about 700 U/mL, from about 600 U/mL to about 800 U/mL, or from about 700 U/mL to about 900 U/mL). In some cases, a fibrin hydrogel provided herein can include about 1 U/mL thrombin polypeptides. In some cases, a fibrin hydrogel provided herein can include about 33 U/mL thrombin polypeptides.

When one or more fibrinogen polypeptides and/or one or more thrombin polypeptide(s) are obtained from (e.g., are isolated from) one or more animals, such as a mammal to be treated using a fibrin hydrogel provided herein, any appropriate method can be used to obtain the fibrinogen polypeptide(s) and/or the thrombin polypeptide(s). For example, one or more fibrinogen polypeptides and/or one or more thrombin polypeptides can be isolated from blood plasma obtained from one or more animals (e.g., a mammal to be treated using a fibrin hydrogel provided herein) using a precipitation technique (e.g. cryoprecipitation, ethanol precipitation, and ammonium sulfate precipitation), ultrafiltration, affinity chromatography, and high performance liquid chromatography (HPLC). In some cases, fibrinogen polypeptide(s) and/or thrombin polypeptide(s) can be obtained from a single animal. In some cases, fibrinogen polypeptide(s) and/or thrombin polypeptide(s) can be obtained from two or more animals (e.g., from a pooled sample from two or more animals). In some cases, fibrinogen polypeptide(s) and/or thrombin polypeptide(s) can be obtained from a mammal to be treated as described herein (e.g., can be autologous fibrinogen polypeptide(s) and/or autologous thrombin polypeptide(s)). In some cases, fibrinogen polypeptide(s) and/or thrombin polypeptide(s) can be obtained from one or more donor animals (e.g., can be allogeneic polypeptide(s) and/or allogeneic thrombin polypeptide(s)).

A fibrin hydrogel provided herein (e.g., a fibrin hydrogel including one or more fibrinogen polypeptides, one or more thrombin polypeptides, and a compound of Formula (I) or Formula (II) such as TB, EB, and/or isomers thereof) can include (e.g., can be formed from a gelation mixture including) a compound of Formula (I):

(I)

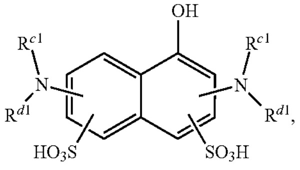

or a pharmaceutically acceptable salt thereof, wherein $R^{c1}$ and $R^{d1}$ are each independently selected from H and $C_{1-3}$ alkyl, or $R^{c1}$ and $R^{d1}$, together with the N atom to which they are attached form a group of formula:

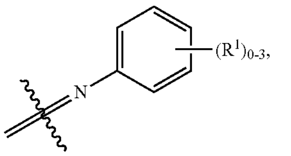

wherein each $R^1$ is independently selected from $C_{1-3}$ alkyl and $C_{1-3}$ alkoxy. In some embodiments, $R^{c1}$ and $R^{d1}$ are each independently selected from H and $C_{1-3}$ alkyl. In some embodiments, the compound of Formula (I) has formula:

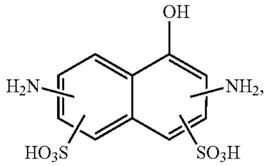

or a pharmaceutically acceptable salt thereof. In some embodiments, $R^{c1}$ and $R^{d1}$, together with the N atom to which they are attached form a group of formula:

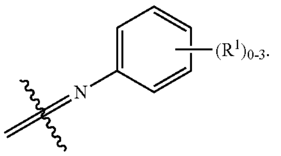

In some embodiments, $R^1$ is $C_{1-3}$ alkyl. In some embodiments, $R^1$ is $C_{1-3}$ alkoxy. In some embodiments, $R^{c1}$ and $R^{d1}$, together with the N atom to which they are attached form a group of formula:

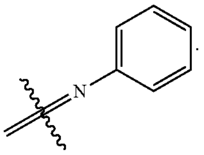 [SMILES: *=Nc1ccccc1]

In some embodiments, the compound of Formula (I) has formula:

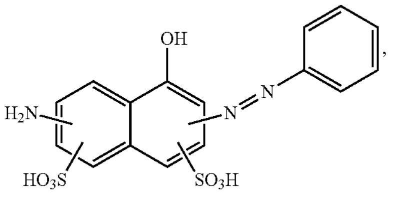

or a pharmaceutically acceptable salt thereof.

In some embodiments, the compound of Formula (I) has formula:

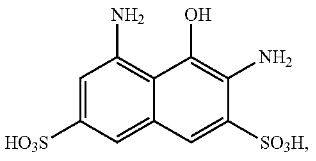 [SMILES: Nc1c(S(=O)(=O)O)cc2cc(S(=O)(=O)O)cc(N)c2c1O]

or a pharmaceutically acceptable salt thereof.

In some embodiments, the compound of Formula (I) has formula:

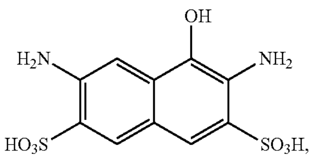 [SMILES: Nc1cc2c(O)c(N)c(S(=O)(=O)O)cc2cc1S(=O)(=O)O]

or a pharmaceutically acceptable salt thereof.

In some embodiments, the compound of Formula (I) has formula:

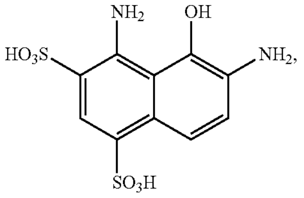 [SMILES: Nc1ccc2c(S(=O)(=O)O)cc(S(=O)(=O)O)c(N)c2c1O]

or a pharmaceutically acceptable salt thereof.

In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or isomers thereof) can include (e.g., can be formed from a gelation mixture including) a compound of Formula (II):

(II)

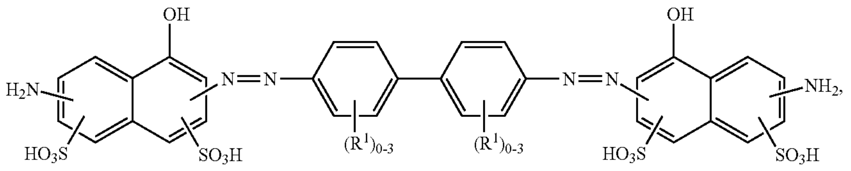

or a pharmaceutically acceptable salt thereof, wherein each $R^1$ is independently selected from $C_{1-3}$ alkyl and $C_{1-3}$ alkoxy.

In some embodiments, the compound of Formula (II) has formula:

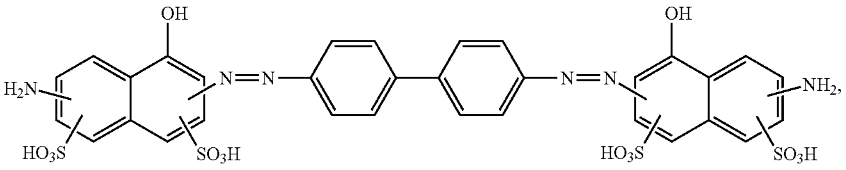

or a pharmaceutically acceptable salt thereof.

In some embodiments, the compound of Formula (II) has formula:

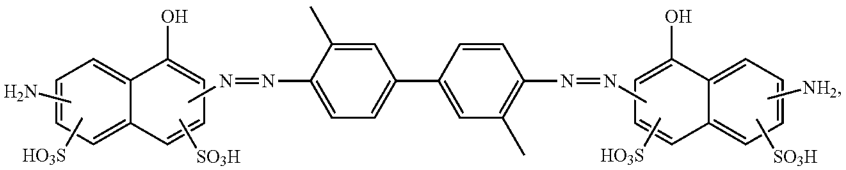

or a pharmaceutically acceptable salt thereof.

In some embodiments, the compound of Formula (II) has formula:

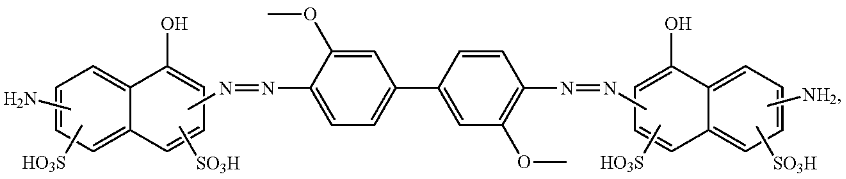

or a pharmaceutically acceptable salt thereof.

In some embodiments, the compound of Formula (II) has formula:

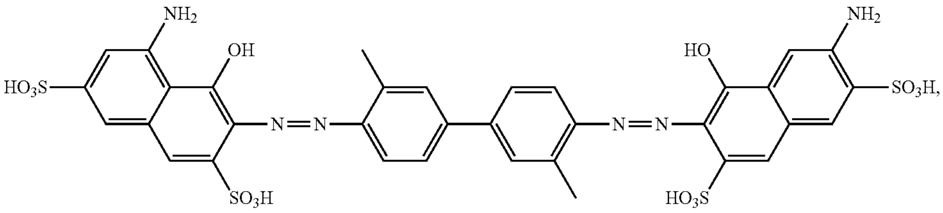 [SMILES: Cc1cc(-c2ccc(N=Nc3c(S(=O)(=O)O)cc4cc(S(=O)(=O)O)cc(N)c4c3O)c(C)c2)ccc1N=Nc1c(S(=O)(=O)O)cc2cc(S(=O)(=O)O)c(N)cc2c1O]

or a pharmaceutically acceptable salt thereof.

In some embodiments, the compound of Formula (II) has formula:

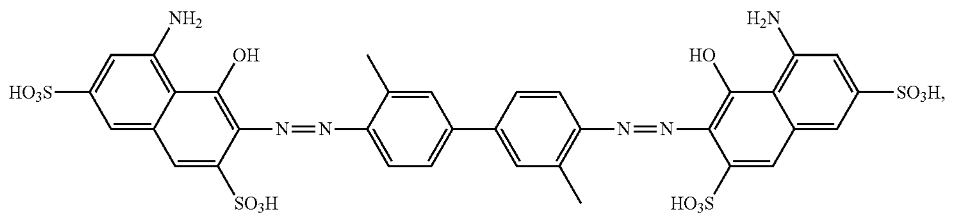

or a pharmaceutically acceptable salt thereof.

In some embodiments, the compound of Formula (II) has formula:

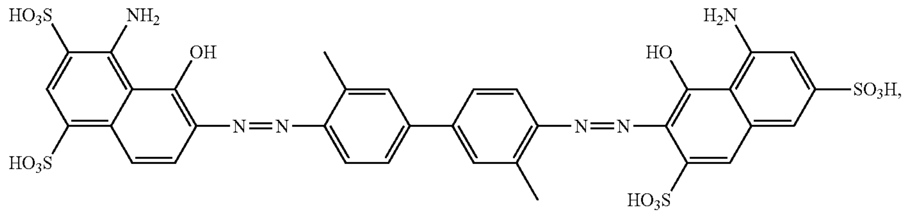 [SMILES: Cc1cc(-c2ccc(N=Nc3c(S(=O)(=O)O)cc4cc(S(=O)(=O)O)cc(N)c4c3O)c(C)c2)ccc1N=Nc1ccc2c(S(=O)(=O)O)cc(S(=O)(=O)O)c(N)c2c1O]

or a pharmaceutically acceptable salt thereof.

In some embodiments, the compound of Formula (II) has formula:

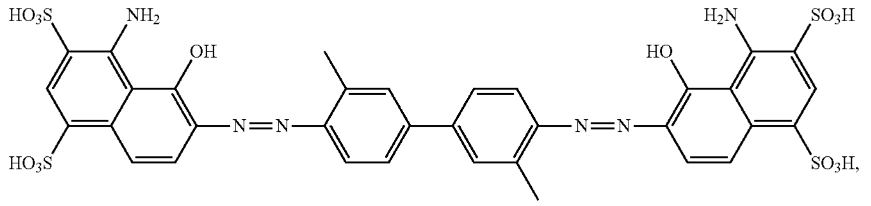 [SMILES: Cc1cc(-c2ccc(N=Nc3ccc4c(S(=O)(=O)O)cc(S(=O)(=O)O)c(N)c4c3O)c(C)c2)ccc1N=Nc1ccc2c(S(=O)(=O)O)cc(S(=O)(=O)O)c(N)c2c1O]

or a pharmaceutically acceptable salt thereof.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or isomers thereof) can include (e.g., can be formed from a gelation mixture including) TB, EB, and/or one or more isomers thereof. The chemical structures for TB and EB can be as shown in FIG. 1. TB, EB, and isomers thereof can have the chemical formula $C_{34}H_{24}N_6O_{14}S_4$. In some cases, an isomer of TB and EB can include four sulfonate groups. In some cases, an isomer of TB and EB can include a similar arrangement of sulfonate groups. In some cases, an isomer of TB and EB can be a similar size molecule to TB and EB. In some cases, TB, EB, or an isomer thereof can be in the form of a salt. For example, TB, EB, or an isomer thereof can be in the form of a sodium (Na) salt or a hydrogen (H) salt. As an alternative to, or in addition to, TB, EB, and/or one or more isomers thereof, a fibrin hydrogel provided herein can include one or more compounds related to TB, EB, and/or one or more isomers thereof. Examples of TB and EB that can be included in a fibrin hydrogel provided herein (e.g., can be included in a gelation mixture for a fibrin hydrogel provided herein) include, without limitation, Trypan blue, VisionBlue®, Direct Blue 53, Azovan Blue, compounds having the structure listed under PubChem Compound ID number (CID) 6296 (TB), and compounds having the structure listed under PubChem CID 9409 (EB). Examples of isomers of TB and EB and related compounds that can be included in a fibrin hydrogel provided herein (e.g., can be included in a gelation mixture for a fibrin hydrogel provided herein) include, without limitation, Direct Blue 2, Melantherine BH, Pontamine sky blue 5B, Azo Fuchsine, and Acid Red 99.

A fibrin hydrogel provided herein (e.g., a fibrin hydrogel including one or more fibrinogen polypeptides, one or more thrombin polypeptides, and TB, EB, and/or one or more isomers thereof) can include any amount of TB, EB, and/or one or more isomers thereof (e.g., can include any amount of TB, EB, and/or one or more isomers thereof within a gelation mixture prior to gelation of the fibrin hydrogel). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include any amount of a compound of Formula (I) and/or or Formula (II) (e.g., can include any amount of a compound of Formula (I) or Formula (II) such as TB, EB, and/or one or more isomers thereof within a gelation mixture prior to gelation of the fibrin hydrogel). For example, a fibrin hydrogel provided herein can include (e.g., can be formed from a gelation mixture including) from about 0.0001% (w/v) to about 0.5% (w/v) a compound of Formula (I) or Formula (II) such as TB, EB, and/or one or more isomers thereof (e.g., from about 0.001% (w/v) to about 0.5% (w/v), from about 0.01% (w/v) to about 0.5% (w/v), from about 0.1% (w/v) to about 0.5% (w/v), from about 0.2% (w/v) to about 0.5% (w/v), from about 0.3% (w/v) to about 0.5% (w/v), from about 0.4% (w/v) to about 0.5% (w/v), from about 0.0001% (w/v) to about 0.4% (w/v), from about 0.0001% (w/v) to about 0.3% (w/v), from about 0.0001% (w/v) to about 0.2% (w/v), from about 0.0001% (w/v) to about 0.1% (w/v), from about 0.0001% (w/v) to about 0.01% (w/v), from about 0.001% (w/v) to about 0.3% (w/v), from about 0.001% (w/v) to about 0.1% (w/v), from about 0.01% (w/v) to about 0.15% (w/v), or from about 0.1% (w/v) to about 0.3% (w/v)). In some cases, a fibrin hydrogel provided herein can include about 0.01% (w/v) a compound of Formula (I) or Formula (II) such as TB, EB, and/or one or more isomers thereof. In some cases, a fibrin hydrogel provided herein can include about 0.15% (w/v) a compound of Formula (I) or Formula (II) such as TB, EB, and/or one or more isomers thereof. In some cases, a fibrin hydrogel provided herein can include a concentration of TB, EB and/or one or more isomers thereof that is lower than a solubility concentration of the TB, EB and/or one or more isomers thereof. For example, a gelation mixture for a fibrin hydrogel provided herein can include less than about 10 mg/mL TB (e.g., about 10 mg/mL TB, 9 mg/mL TB, 8 mg/mL TB, 7 mg/mL TB, 6 mg/mL TB, or 5 mg/mL TB). For example, a gelation mixture for a fibrin hydrogel provided herein can include less than about 50 mg/mL EB (e.g., about 45 mg/mL EB, about 40 mg/mL EB, about 35 mg/mL EB, about 30 mg/mL EB, about 25 mg/mL EB, about 20 mg/mL EB, about 15 mg/mL EB, or about 10 mg/mL EB).

In some cases, a fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) 5 to 15 mg/mL fibrinogen polypeptides, 0.5 to 5 U/mL thrombin polypeptides, and 0.005 to 0.05% (w/v) TB, EB, and/or one or more isomers thereof. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) 5 to 15 mg/mL fibrinogen polypeptides, 0.5 to 5 U/mL thrombin polypeptides, and 0.005 to 0.05% (w/v) TB, EB, and/or one or more isomers thereof.

In some cases, a fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) 10 mg/mL fibrinogen polypeptides, 1 U/mL thrombin polypeptides, and 0.01% (w/v) TB, EB, and/or one or more isomers thereof. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) 10 mg/mL fibrinogen polypeptides, 1 U/mL thrombin polypeptides, and 0.01% (w/v) TB, EB, and/or one or more isomers thereof.

In some cases, a fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) 20 to 60 mg/mL fibrinogen polypeptides, 20 to 40 U/mL thrombin polypeptides, and 0.05 to 0.5% (w/v) TB, EB, and/or one or more isomers thereof. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) 20 to 60 mg/mL fibrinogen polypeptides, 20 to 40 U/mL thrombin polypeptides, and 0.05 to 0.5% (w/v) TB, EB, and/or one or more isomers thereof.

In some cases, a fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) 40 mg/mL fibrinogen polypeptides, 33 U/mL thrombin polypeptides, and 0.12% (w/v) TB, EB, and/or one or more isomers thereof. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) 40 mg/mL fibrinogen polypeptides, 33 U/mL thrombin polypeptides, and 0.12% (w/v) TB, EB, and/or one or more isomers thereof.

In some cases, a fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) one or more additional components. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) one or more additional components. For example, a fibrin hydrogel provided herein can include one or more extracellular matrix (ECM) components (e.g., fibronectin, vitronectin, laminin, and collagen). For example, a fibrin hydrogel provided herein can include one or more coagulation factors (e.g., physiological concentrations of one or more coagulation factors) such as factor IX, prothrombin, factor XIII, and factor VIII. For example, a fibrin hydrogel provided herein can include one or more heparin binding sequences (e.g., heparin binding sequences from antithrombin III, heparin binding sequences from neural cell adhesion molecules, and heparin binding sequences from platelet factor 4). For example, a fibrin hydrogel provided herein can include one or more fibrinolytic agents (e.g., tissue plasminogen activator, plasminogen, and urokinase plasminogen activator). For example, a fibrin hydrogel provided herein can include one or more anti-fibrinolytic agents (e.g., aprotinin, recombinant aprotinin, tranexamic acid, and ε-caproic acid). For example, a fibrin hydrogel provided herein can include one or more growth factors (e.g., fibroblast growth factor, neurotrophin 3, transforming growth factor beta 1, transforming growth factor beta 2, nerve growth factor, brain derived neurotrophic factor, pigment epithelium derived factor, and vascular endothelium growth factor).

In some cases, a fibrin hydrogel provided herein (e.g., a fibrin hydrogel including one or more fibrinogen polypeptides, one or more thrombin polypeptides, and TB, EB, and/or one or more isomers thereof) can include (e.g., can be formed from a gelation mixture including) one or more therapeutic agents. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can include (e.g., can be formed from a gelation mixture including) one or more therapeutic agents. For example, a fibrin hydrogel provided herein can include one or more therapeutic agents and can be used to deliver the one or more therapeutic agents to a mammal. Examples of therapeutic agents that can be included in a fibrin hydrogel provided herein include, without limitation, gene therapy viral vectors, antibodies, small molecules, and cells.

A fibrin hydrogel provided herein (e.g., a fibrin hydrogel including one or more fibrinogen polypeptides, one or more thrombin polypeptides, and TB, EB, and/or one or more isomers thereof) can be visualized (e.g., within a mammal) using any appropriate method. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can be visualized (e.g., within a mammal) using any appropriate method. For example, imaging techniques such as light microscopy, fundus photography, infrared imaging, optical coherence tomography (OCT), computerized tomography (CT), and/or magnetic resonance imaging (MRI) can be used to visualize a fibrin hydrogel provided herein.

In some cases, a fibrin hydrogel provided herein (e.g., a fibrin hydrogel including one or more fibrinogen polypeptides, one or more thrombin polypeptides, and TB, EB, and/or one or more isomers thereof) can have a delayed gelation time (e.g., a delayed polymerization of fibrins within the fibrin hydrogel). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can have a delayed gelation time (e.g., a delayed polymerization of fibrins within the fibrin hydrogel). For example, a fibrin hydrogel provided herein can have a polymerization time that is slower than a polymerization time typically found in fibrin hydrogels that lack TB, EB, and one or more isomers thereof. In some cases, a fibrin hydrogel provided herein can have a polymerization time that is greater than about 2 seconds. In some cases, a fibrin hydrogel provided herein can have a polymerization time that is from about 2 seconds to about 1200 seconds (e.g., about 2 seconds to about 1000 seconds, about 2 seconds to about 800 seconds, about 2 seconds to about 600 seconds, about 2 seconds to about 400 seconds, about 2 seconds to about 200 seconds, about 2 seconds to about 100 seconds, about 2 seconds to about 75 seconds, about 2 seconds to about 60 seconds, about 2 seconds to about 45 seconds, about 2 seconds to about 30 seconds, about 15 seconds to about 1200 seconds, about 30 seconds to about 1200 seconds, about 45 seconds to about 1200 seconds, about 60 seconds to about 1200 seconds, about 120 seconds to about 1200 seconds, about 400 seconds to about 1200 seconds, about 600 seconds to about 1200 seconds, about 800 seconds to about 1200 seconds, about 30 seconds to about 600 seconds, about 60 seconds to about 120 seconds, about 120 seconds to about 360 seconds, about 360 seconds to about 480 seconds, about 480 seconds to about 600 seconds, about 600 seconds to about 720 seconds, about 720 seconds to about 840 seconds, or about 840 seconds to about 1200 seconds). In some cases, the polymerization time can be affected by the concentration of one or more fibrinogen polypeptides within the fibrin hydrogel. For example, a fibrin hydrogel containing about 10 mg/mL fibrinogen polypeptides can have a polymerization time that is from about 30 seconds to about 400 seconds. For example, a fibrin hydrogel containing about 40 mg/mL fibrinogen polypeptides can have a polymerization time that is from about 1 second to about 200 seconds.

In some cases, a fibrin hydrogel provided herein (e.g., a fibrin hydrogel including one or more fibrinogen polypeptides, one or more thrombin polypeptides, and TB, EB, and/or one or more isomers thereof) can have increased shear strength. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can have increased shear strength. For example, a fibrin hydrogel provided herein can have a shear strength that is comparable to or greater than a shear strength typically found in fibrin hydrogels that lack TB, EB, and one or more isomers thereof. In some cases, a fibrin hydrogel provided herein can have a shear modulus of from about 500 Pascal (Pa) to about 50,000 Pa (e.g., from about 500 Pa to about 25,000 Pa, from about 500 Pa to about 10,000 Pa, from about 500 Pa to about 5,000 Pa, from about 500 Pa to about 1,000 Pa, from about 1,000 Pa to about 50,000 Pa, from about 5,000 Pa to about 50,000 Pa, from about 10,000 Pa to about 50,000 Pa, from about 25,000 Pa to about 50,000 Pa, from about 1,000 Pa to about 25,000 Pa, from about 5,000 Pa to about 10,000 Pa, from about 1,000 Pa to about 5,000 Pa, from about 5,000 Pa to about 10,000 Pa, or from about 10,000 Pa to about 25,000 Pa). The shear modulus can vary based on the geometry of the setup in which a fibrin hydrogel is formed. For example, a fibrin hydrogel provided herein can have a shear modulus of from about 1000 Pa to about 3000 Pa (e.g., about 2197±221 Pa). For example, a fibrin hydrogel provided herein can have a shear modulus of from about 1600 Pa to about 2520 Pa (e.g., about 2077±441).

In some cases, a fibrin hydrogel provided herein (e.g., a fibrin hydrogel including one or more fibrinogen polypeptides, one or more thrombin polypeptides, and TB, EB, and/or one or more isomers thereof) can have small fibrils. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can have small fibrils. For example, fibrils within a fibrin hydrogel provided herein can have a diameter (e.g., a mean diameter) that is comparable to or smaller than a diameter (e.g., a mean diameter) of fibrils typically found in fibrin hydrogels that lack TB, EB, and one or more isomers thereof. In some cases, a fibrin hydrogel provided herein can include fibrils having a diameter (e.g., a mean diameter) of from about 1 nanometer (nm) to about 400 nm (e.g., from about 1 nm to about 400 nm, from about 1 nm to about 300 nm, from about 1 nm to about 200 nm, from about 1 nm to about 100 nm, from about 1 nm to about 75 nm, from about 1 nm to about 50 nm, from about 1 nm to about 25 nm, from about 10 nm to about 400 nm, from about 25 nm to about 400 nm, from about 50 nm to about 400 nm, from about 100 nm to about 400 nm, from about 200 nm to about 400 nm, from about 300 nm to about 400 nm, or from about 100 nm to about 300 nm). For example, a fibrin hydrogel provided herein can include fibrils having a diameter (e.g., a mean diameter) of from about 50 nm to about 100 nm. For example, a fibrin hydrogel provided herein can include fibrils having a diameter (e.g., a mean diameter) of from about 40 nm to about 60 nm.

In some cases, a fibrin hydrogel provided herein (e.g., a fibrin hydrogel including one or more fibrinogen polypeptides, one or more thrombin polypeptides, and TB, EB, and/or one or more isomers thereof) can have increased crosslinking density. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can have increased crosslinking density. For example, fibrils within a fibrin hydrogel provided herein can have a crosslinking density that is comparable to or greater than a fibril crosslinking density typically found in fibrin hydrogels that lack TB, EB, and one or more isomers thereof. In some cases, a fibrin hydrogel provided herein can have a fibril crosslinking density of from about 1 crosslink/$\mu m^2$ to about 5,000 crosslinks/$\mu m^2$ (e.g., from about 1 crosslink/$\mu m^2$ to about 4,000 crosslinks/$\mu m^2$, from about 1 crosslink/$\mu m^2$ to about 3,000 crosslinks/$\mu m^2$, from about 1 crosslink/$\mu m^2$ to about 2,000 crosslinks/$\mu m^2$, from about 1 crosslink/$\mu m^2$ to about 1,000 crosslinks/$\mu m^2$, from about 1 crosslink/$\mu m^2$ to about 750 crosslinks/$\mu m^2$, from about 1 crosslink/$\mu m^2$ to about 500 crosslinks/$\mu m^2$, from about 1 crosslink/$\mu m^2$ to about 100 crosslinks/$\mu m^2$, from about 1 crosslink/$\mu m^2$ to about 50 crosslinks/$\mu m^2$, from about 50 crosslink/$\mu m^2$ to about 5,000 crosslinks/$\mu m^2$, from about 100 crosslink/$\mu m^2$ to about 5,000 crosslinks/$\mu m^2$, from about 500 crosslink/$\mu m^2$ to about 5,000 crosslinks/$\mu m^2$, from about 1,000 crosslink/$\mu m^2$ to about 5,000 crosslinks/$\mu m^2$, from about 2,000 crosslink/$\mu m^2$ to about 5,000 crosslinks/$\mu m^2$, from about 3,000 crosslink/$\mu m^2$ to about 5,000 crosslinks/$\mu m^2$, from about 4,000 crosslink/$\mu m^2$ to about 5,000 crosslinks/$\mu m^2$, from about 50 crosslink/$\mu m^2$ to about 3,000 crosslinks/$\mu m^2$, from about 100 crosslink/$\mu m^2$ to about 2,000 crosslinks/$\mu m^2$, from about 500 crosslink/$\mu m^2$ to about 1,000 crosslinks/$\mu m^2$, from about 100 crosslink/$\mu m^2$ to about 400 crosslinks/$\mu m^2$, from about 300 crosslink/$\mu m^2$ to about 500 crosslinks/$\mu m^2$, from about 800 crosslink/$\mu m^2$ to about 1,000 crosslinks/$\mu m^2$, or from about 1,000 crosslink/$\mu m^2$ to about 3,000 crosslinks/$\mu m^2$).

In some cases, a fibrin hydrogel provided herein (e.g., a fibrin hydrogel including one or more fibrinogen polypeptides, one or more thrombin polypeptides, and TB, EB, and/or one or more isomers thereof) can be degradable (e.g., can be biodegradable). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can be degradable (e.g., can be biodegradable). For example, a volume of a fibrin hydrogel (e.g., a fibrin hydrogel that has been delivered to a mammal) can decrease over time. In some cases, a volume of a fibrin hydrogel that has been delivered to a mammal (e.g., a human) can decrease by at least about 25% (e.g., at least about 35%, at least about 50%, at least about 60%, at least about 70%, at least about 80%, at least about 85%, at least about 90%, at least about 92%, at least about 95%, at least about 98%, or at least about 99%) over time. In some cases, a volume of a fibrin hydrogel that has been delivered to a mammal (e.g., a human) can decrease for from about 5 minutes to about 12 months (e.g., from about 5 minutes to about 6 months, from about 5 minutes to about 3 months, from about 5 minutes to about 1 month, from about 5 minutes to about 1 week, from about 5 minutes to about 4 days, from about 5 minutes to about 1 day, from about 5 minutes to about 12 hours, from about 5 minutes to about 6 hours, from about 5 minutes to about 3 hours, from about 5 minutes to about 60 minutes, from about 1 hour to about 12 months, from about 1 week to about 12 months, from about 1 month to about 12 months, from about 6 months to about 12 months, from about 1 hour to about 1 month, or from about 1 day to about 1 week) following delivery. In some cases when a fibrin hydrogel provided herein decreases in volume, the fibrin hydrogel can have been exposed to one or more fibrinolytic enzymes (e.g. plasminogen and tissue plasminogen activator). For example, when a fibrin hydrogel provided herein is exposed to about 1.6 U/mL plasminogen and/or about 17,000 U/mL tissue plasminogen activator (e.g., exposed to about 1.6 U/mL plasminogen and/or about 17,000 U/mL tissue plasminogen activator at about 37° C.), a volume of the fibrin hydrogel can decrease over time. In some cases, a volume of a fibrin hydrogel that has been exposed to one or more fibrinolytic enzymes can decrease for from about 5 minutes to about 200 minutes (e.g., from about 5 minutes to about 180 minutes, from about 5 minutes to about 150 minutes, from about 5 minutes to about 120 minutes, from about 5 minutes to about 90 minutes, from about 5 minutes to about 60 minutes, from about 5 minutes to about 45 minutes, from about 5 minutes to about 30 minutes, from about 5 minutes to about 10 minutes, from about 1 minutes to about 200 minutes, from about 30 minutes to about 200 minutes, from about 45 minutes to about 200 minutes, from about 60 minutes to about 200 minutes, from about 90 minutes to about 200 minutes, from about 120 minutes to about 200 minutes, from about 150 minutes to about 200 minutes, from about 15 minutes to about 180 minutes, from about 30 minutes to about 150 minutes, from about 45 minutes to about 120 minutes, from about 60 minutes to about 90 minutes, from about 30 minutes to about 60 minutes, from about 60 minutes to about 90 minutes, from about 90 minutes to about 120 minutes, from about 120 minutes to about 150 minutes, or from about 150 minutes to about 180 minutes).

In some cases, a fibrin hydrogel provided herein (e.g., a fibrin hydrogel including one or more fibrinogen polypeptides, one or more thrombin polypeptides, and TB, EB, and/or one or more isomers thereof) can have uniform fibrils. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can have uniform fibrils. For example, fibrils within a fibrin hydrogel provided herein can be more uniform (e.g., can have a lower standard deviation value) than fibrils typically found in fibrin hydrogels that lack TB, EB, and one or more isomers thereof.

In some cases, a fibrin hydrogel provided herein (e.g., a fibrin hydrogel including one or more fibrinogen polypeptides, one or more thrombin polypeptides, and TB, EB, and/or one or more isomers thereof) can have a smooth surface. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can have a smooth surface. For example, a fibrin hydrogel provided herein can have a smoother surface (e.g., can have fewer and/or smaller surface abnormalities such as craters and mounds) than fibrin hydrogels that lack TB, EB, and one or more isomers thereof.

A fibrin hydrogel provided herein (e.g., a fibrin hydrogel including one or more fibrinogen polypeptides, one or more thrombin polypeptides, and TB, EB, and/or one or more isomers thereof) can be any size. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can be any size. In some cases, a fibrin hydrogel provided herein can have a width of from about 0.5 millimeters (mm) to about 6 mm (e.g., from about 0.5 mm to about 5 mm, from about 0.5 mm to about 4 mm, from about 0.5 mm to about 3 mm, from about 0.5 mm to about 2 mm, from about 0.5 mm to about 1 mm, from about 1 mm to about 6 mm, from about 2 mm to about 6 mm, from about 3 mm to about 6 mm, from about 4 mm to about 6 mm, from about 5 mm to about 6 mm, from about 1 mm to about 5 mm, from about 2 mm to about 4 mm, from about 1 mm to about 3 mm, or from about 3 mm to about 5 mm). For example, a fibrin hydrogel provided herein can have a width of about 1.5 mm. In some cases, a fibrin hydrogel provided herein can have a length of from about 1 mm to about 8 mm (e.g., from about 1 mm to about 8 mm, from about 1 mm to about 7 mm, from about 1 mm to about 6 mm, from about 1 mm to about 5 mm, from about 1 mm to about 4 mm, from about 1 mm to about 3 mm, from about 2 mm to about 8 mm, from about 3 mm to about 8 mm, from about 4 mm to about 8 mm, from about 5 mm to about 8 mm, from about 6 mm to about 8 mm, from about 2 mm to about 7 mm, from about 3 mm to about 6 mm, from about 4 mm to about 5 mm, from about 2 mm to about 4 mm, from about 3 mm to about 5 mm, or from about 4 mm to about 6 mm). For example, a fibrin hydrogel provided herein can have a length of about 5 mm. In some cases, a fibrin hydrogel provided herein can have a thickness of from about 0.1 μm to about 1,000 μm (e.g., 5 μm to about 1,000 μm, 10 μm to about 1,000 μm, from about 25 μm to about 500 μm, from about 25 μm to about 400 μm, from about 25 μm to about 300 μm, from about 25 μm to about 200 μm, from about 25 μm to about 100 μm, from about 25 μm to about 75 μm, from about 25 μm to about 50 μm, from about 50 μm to about 500 μm, from about 75 μm to about 500 μm, from about 100 μm to about 500 μm, from about 200 μm to about 500 μm, from about 300 μm to about 500 μm, from about 400 μm to about 500 μm, from about 50 μm to about 400 μm, from about 100 μm to about 300 μm, from about 50 μm to about 250 μm, from about 150 μm to about 350 μm, or from about 250 μm to about 450 μm). For example, a fibrin hydrogel provided herein can have a thickness of from about 150 μm to about 380 μm (e.g., about 309±69 μm). For example, a fibrin hydrogel provided herein can have a thickness of from about 200 μm. In some cases, a fibrin hydrogel provided herein can have a surface area that is greater than about 1 $cm^2$. For example, a fibrin hydrogel provided herein can have a surface area of from about 0.05 $cm^2$ to about 300 $cm^2$ (e.g., from about 0.5 $cm^2$ to about 200 $cm^2$, from about 1 $cm^2$ to about 200 $cm^2$, from about 4 $cm^2$ to about 200 $cm^2$, from about 4 $cm^2$ to about 100 $cm^2$, from about 4 $cm^2$ to about 75 $cm^2$, from about 4 $cm^2$ to about 50 $cm^2$, from about 4 $cm^2$ to about 10 $cm^2$, from about 10 $cm^2$ to about 300 $cm^2$, from about 50 $cm^2$ to about 300 $cm^2$, from about 75 $cm^2$ to about 300 $cm^2$, from about 100 $cm^2$ to about 300 $cm^2$, from about 200 $cm^2$ to about 300 $cm^2$, from about 50 $cm^2$ to about 250 $cm^2$, from about 100 $cm^2$ to about 200 $cm^2$, from about 50 $cm^2$ to about 150 $cm^2$, from about 100 $cm^2$ to about 200 $cm^2$, or from about 150 $cm^2$ to about 250 $cm^2$). In some cases, a fibrin hydrogel provided herein can have a surface area of about 15 $cm^2$. In some cases, a fibrin hydrogel provided herein can have a surface area of about 95 $cm^2$.

In some cases, fibrin hydrogel provided herein (e.g., a fibrin hydrogel including one or more fibrinogen polypeptides, one or more thrombin polypeptides, and TB, EB, and/or one or more isomers thereof) can have a width of about 1.5 mm, a length of about 5 mm, and a thickness of about 200 μm. In some cases, fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can have a width of about 1.5 mm, a length of about 5 mm, and a thickness of about 200 μm.

In some cases, a fibrin hydrogel provided herein (e.g., a fibrin hydrogel including one or more fibrinogen polypeptides, one or more thrombin polypeptides, and TB, EB, and/or one or more isomers thereof) can be shaped (e.g., can be shaped using a mold). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can be shaped (e.g., can be shaped using a mold). For example, one or more fibrinogen polypeptides, one or more thrombin polypeptides, and a compound of Formula (I) or Formula (II) such as TB, EB, and/or one or more isomers thereof can be mixed, and, prior to polymerization, can be poured into a mold (e.g., an acetal mold) to polymerize within the mold, thereby shaping the fibrin hydrogel. In some cases, a fibrin hydrogel provided herein can be shaped (e.g., can be shaped using a mold) to fit in a cell culture container (e.g., a cell culture dish, a cell culture plate, and a cell culture flask). For example, a fibrin hydrogel provided herein can be shaped into a circle to fit in a well of a cell culture dish. For example, a fibrin hydrogen provided herein can be shaped into a rectangle to fit in a cell culture flask.

In some cases, a fibrin hydrogel provided herein (e.g., a fibrin hydrogel including one or more fibrinogen polypeptides, one or more thrombin polypeptides, and TB, EB, and/or one or more isomers thereof) can be formed on a surface of a substrate. In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can be formed on a surface of a substrate. Examples of substrate on which a fibrin hydrogel can be formed include, without limitation, slide plates, molds, tubes, microarrays, microchips, and wafers. A substrate can include any appropriate material (e.g., polycarbonate, polystyrene, polypropylene, and glass). A substrate can be any size. For example, a substrate (e.g., a slide plate) that a fibrin hydrogel provided herein can be formed on can have a surface area of from about 0.05 $cm^2$ to about 300 $cm^2$ (e.g., from about 0.5 $cm^2$ to about 200 $cm^2$, from about 1 $cm^2$ to about 200 $cm^2$, from about 4 $cm^2$ to about 200 $cm^2$, from about 4 $cm^2$ to about 100 $cm^2$, from about 4 $cm^2$ to about 75 $cm^2$, from about 4 $cm^2$ to about 50 $cm^2$, from about 4 $cm^2$ to about 10 $cm^2$, from about 10 $cm^2$ to about 300 $cm^2$, from about 50 $cm^2$ to about 300 $cm^2$, from about 75 $cm^2$ to about 300 $cm^2$, from about 100 $cm^2$ to about 300 $cm^2$, from about 200 $cm^2$ to about 300 $cm^2$, from about 50 $cm^2$ to about 250 $cm^2$, from about 100 $cm^2$ to about 200 $cm^2$, from about 50 $cm^2$ to about 150 $cm^2$, from about 100 $cm^2$ to about 200 $cm^2$, or from about 150 $cm^2$ to about 250 $cm^2$).

Also provided herein are methods for making a fibrin hydrogel provided herein (e.g., a fibrin hydrogel including one or more fibrin polypeptides, one or more thrombin polypeptides, and TB, EB, and/or one or more isomers thereof). Also provided herein are methods for making a fibrin hydrogel provided herein (e.g., a fibrin hydrogel including one or more fibrin polypeptides, one or more thrombin polypeptides, and a compound of Formula (I) or Formula (II) such as TB, EB, and/or one or more isomers thereof). In some cases, methods for making a fibrin hydrogel provided herein include making fibrin hydrogels having a delayed gelation time (e.g., a delayed polymerization of fibrins within the fibrin hydrogel). For example, including a compound of Formula (I) or Formula (II) such as TB, EB, and/or one or more isomers thereof in a fibrin hydrogel can be effective to delay the gelation time of a fibrin hydrogel (e.g., to delay polymerization of fibrins within the fibrin hydrogel). A fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) can be made using any appropriate method. In some cases, a compound of Formula (I) or Formula (II) such as TB, EB, and/or one or more isomers thereof can mixed with one or more fibrinogen polypeptides and/or one or more thrombin polypeptides as a solution. In some cases, a compound of Formula (I) or Formula (II) such as TB, EB, and/or one or more isomers thereof can mixed with one or more fibrinogen polypeptides and/or one or more thrombin polypeptides as a powder. In some cases, a compound of Formula (I) or Formula (II) such as TB, EB, and/or one or more isomers thereof and one or more fibrinogen polypeptides can mixed first, and then and one or more thrombin polypeptides can be added. In some cases, a compound of Formula (I) or Formula (II) such as TB, EB, and/or one or more isomers thereof and one or more thrombin polypeptides can mixed first, and then and one or more fibrinogen polypeptides can be added. For example, centrifugal mixing, static mixing, coil/auger/impeller mixing, dynamic/magnetic/bar stirring, aerosolization, container inversion, plate shaker, vortexing, and/or bulk mixing can be used for mixing (e.g., homogenous mixing) of one or more fibrinogen polypeptides, one or more thrombin polypeptides, and a compound of Formula (I) or Formula (II) such as TB, EB, and/or one or more isomers thereof to make a fibrin hydrogel provided herein. In some cases, a fibrin hydrogel can be made by injection molding, pressing, spraying, and/or 3D printing a gelation mixture for a fibrin hydrogel. In some cases, a fibrin hydrogel can be made as described in Example 1.

Also provided herein are methods for using a fibrin hydrogel provided herein (e.g., a fibrin hydrogel including one or more fibrin polypeptides, one or more thrombin polypeptides, and TB, EB, and/or one or more isomers thereof). In some cases, also provided herein are methods for using a fibrin hydrogel provided herein (e.g., a fibrin hydrogel including one or more fibrin polypeptides, one or more thrombin polypeptides, and a compound of Formula (I) or Formula (II) such as TB, EB, and/or one or more isomers thereof). In some cases, a fibrin hydrogel provided herein can be used as a scaffold (e.g., a degradable scaffold) for cell culture applications. For example, a fibrin hydrogel provided herein can be used as a scaffold (e.g., a degradable scaffold) to culture stem cells such as human embryonic stem cells (hESCs) and induced pluripotent stem cells (iPSCs). For example, a fibrin hydrogel provided herein can be used as a scaffold (e.g., a degradable scaffold) to culture retinal pigment epithelium (RPE) cells (e.g., hESC-derived RPE cells or iPSC-derived RPE cells).

Figure 14A:
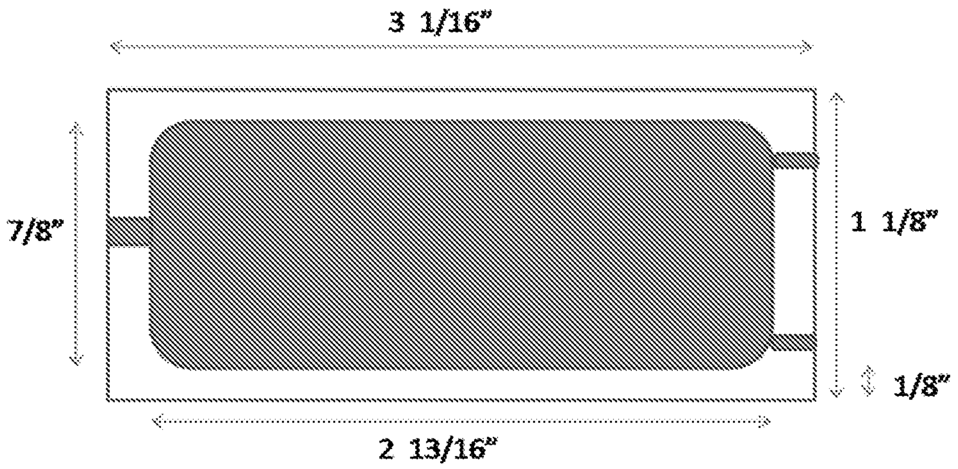
FIGS. 14A-14B.
Figure 14B:
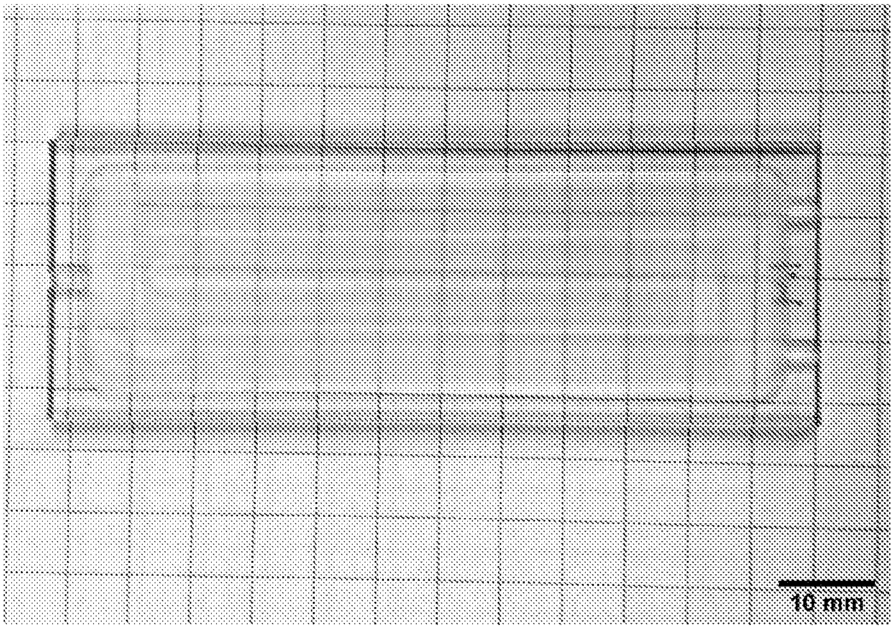
Figure 15:
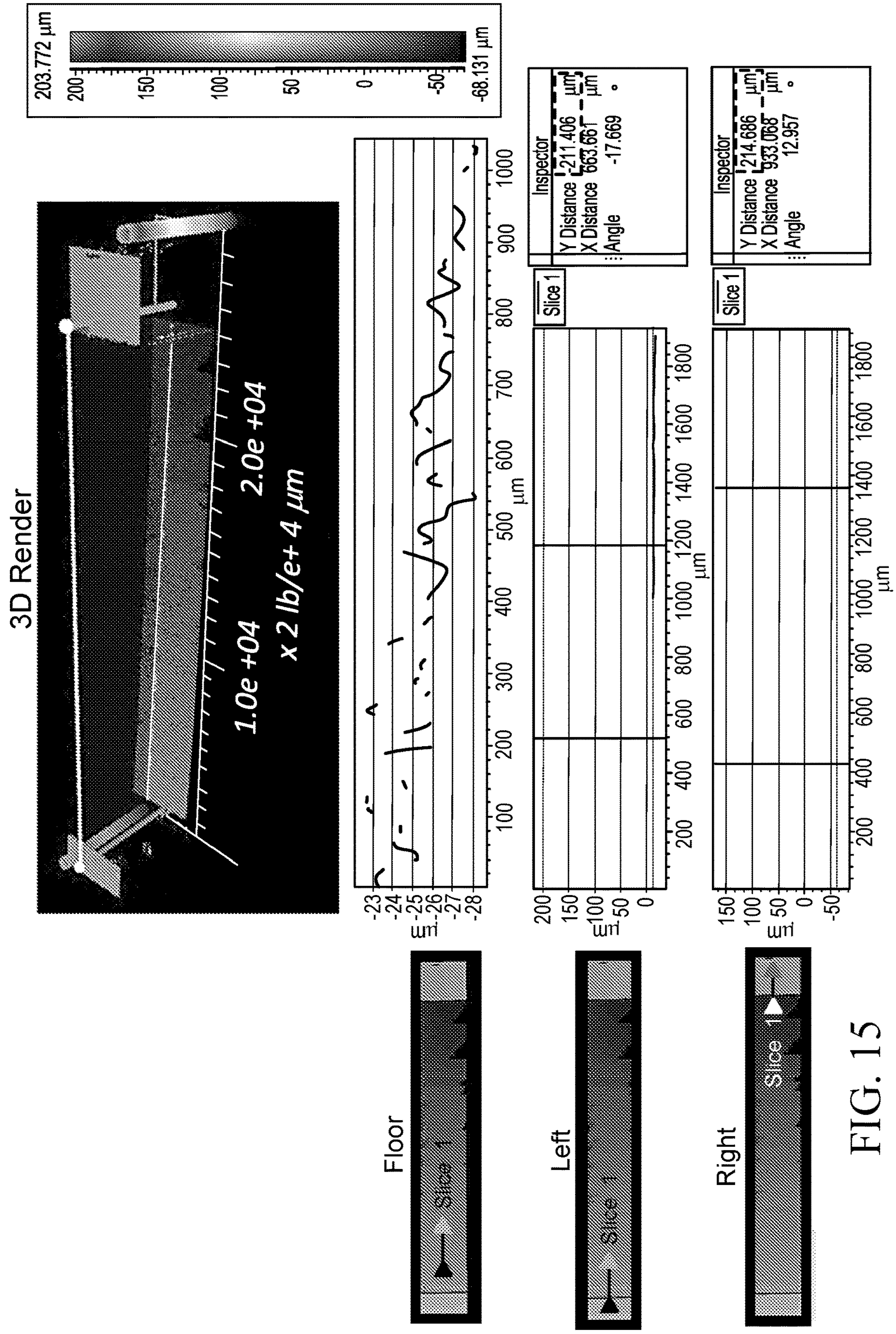
FIG. 15. Interferometry was used to confirm the specifications of the milled polycarbonate plate. The interferometry data was used to generate a 3D render of a cross section of the slide. Measurements were taken across a random section of the floor, the edge on the left and edge on the right and graphed. The variability along the bottom floor was ~5 μm. The left edge measured a depth of 211 μm and the right edge measured a depth of 215 μm.
Figure 16:
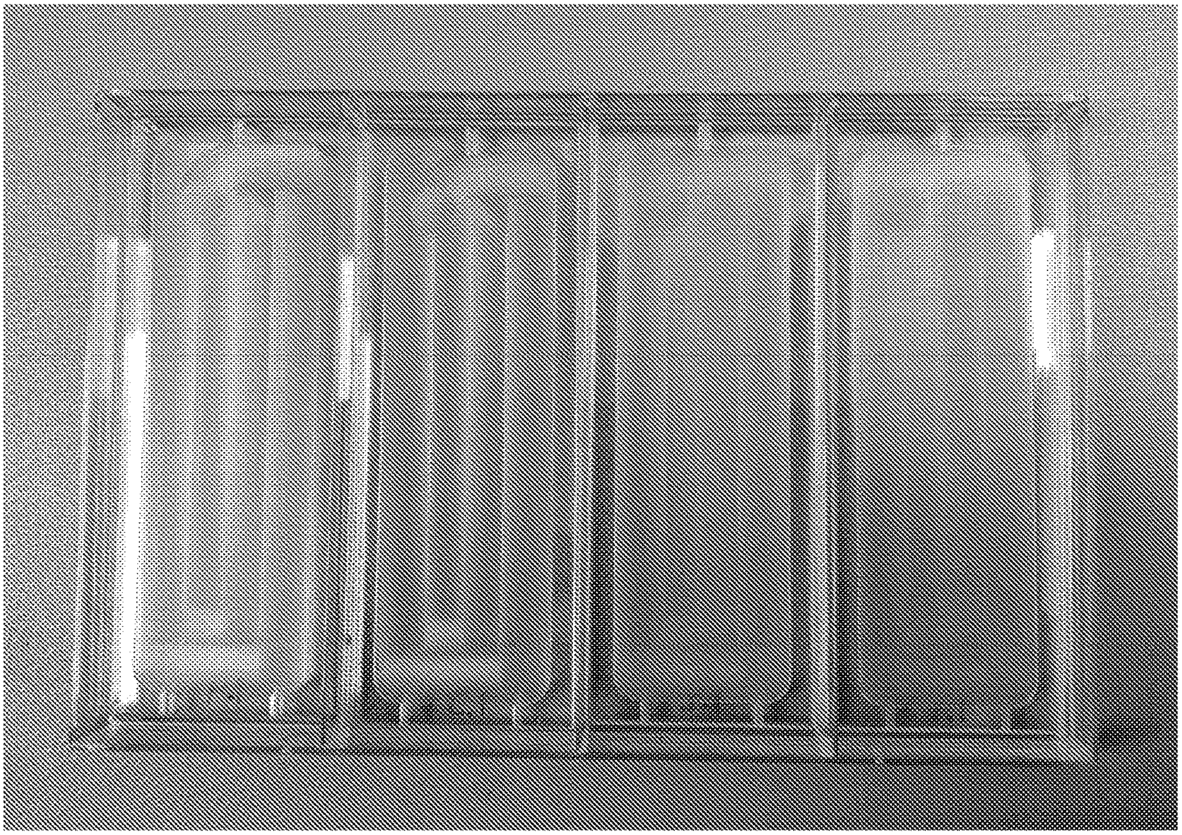
FIG. 16. Photomicrograph of 4 milled slides plated within a 4 well rectangular dish suitable for cell culture.
Figure 17B:
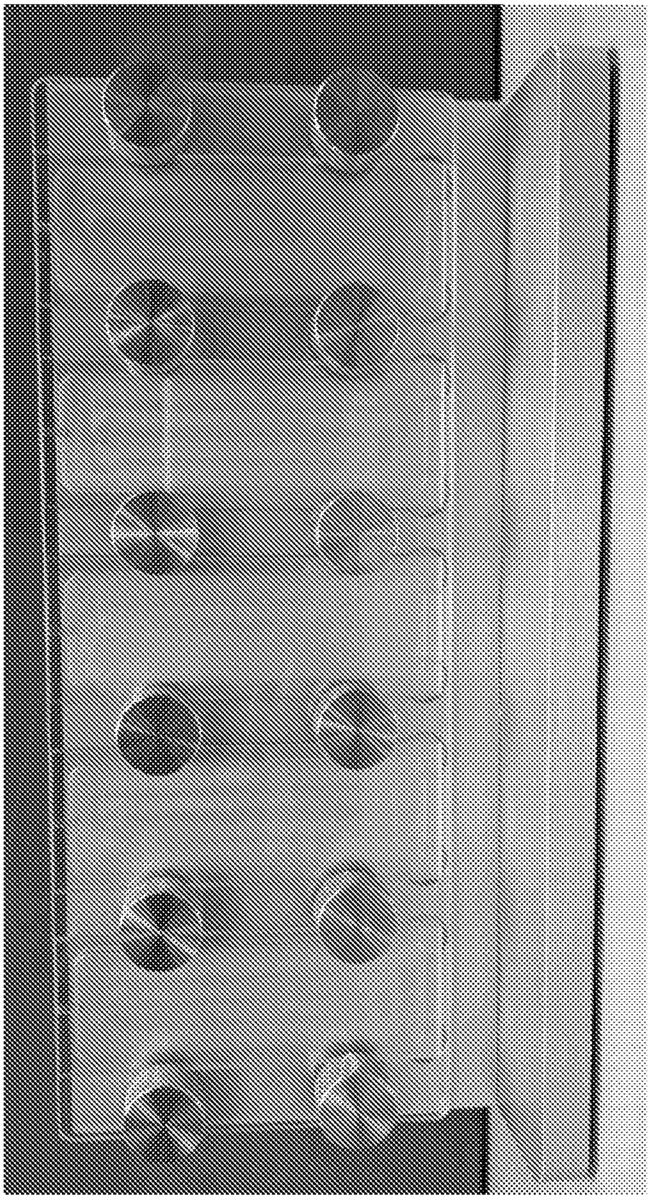
FIGS. 17A-17C.
Figure 17C:
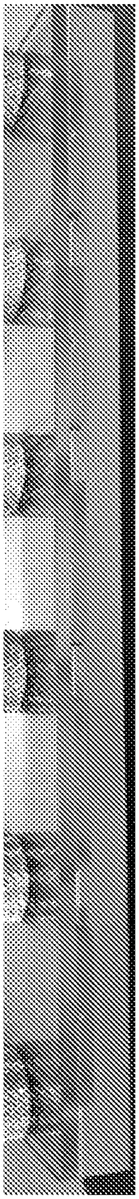
Figure 17A:
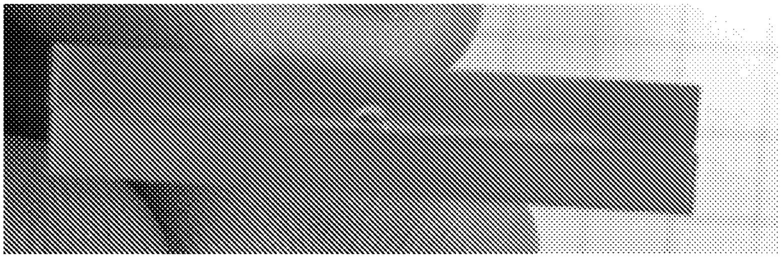
Figure 18A:
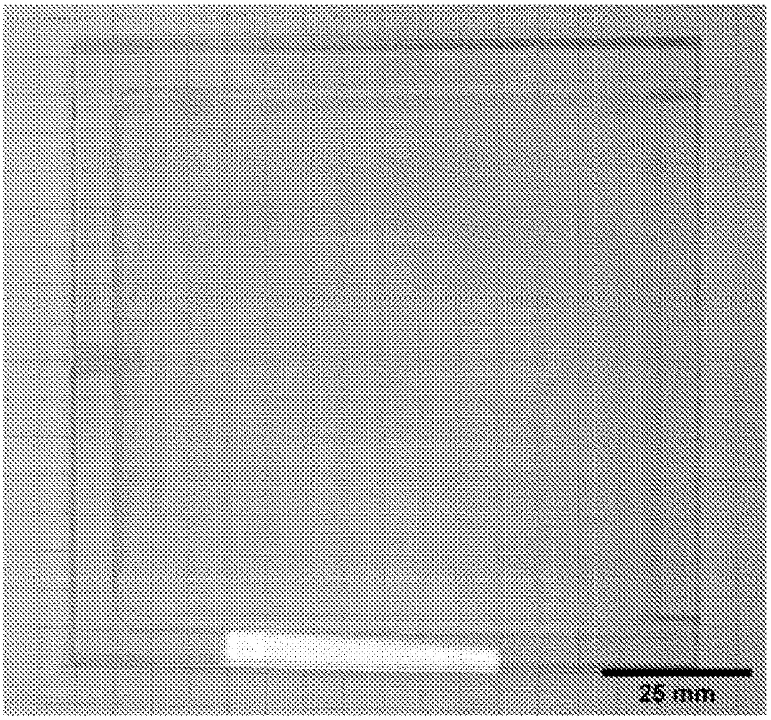
FIGS. 18A-18B.
Figure 18B:
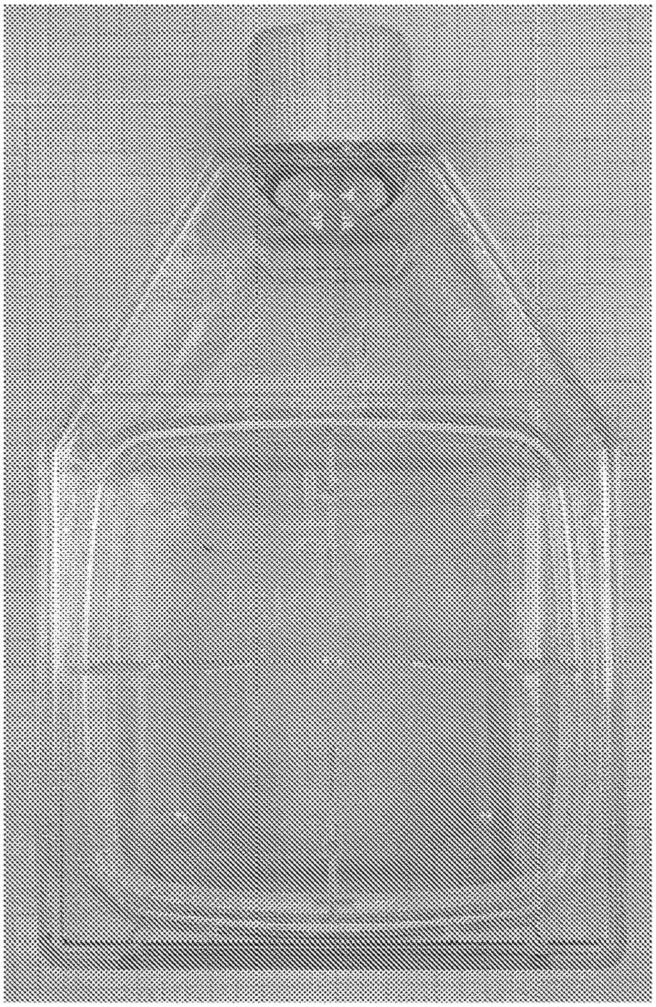
Figure 19B:
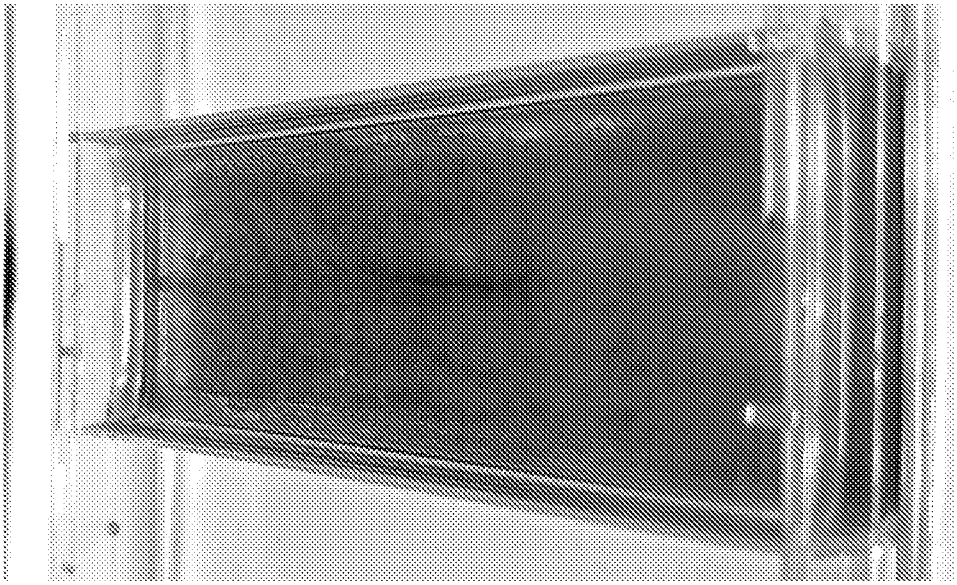
FIGS. 19A-19B.
Figure 19A:
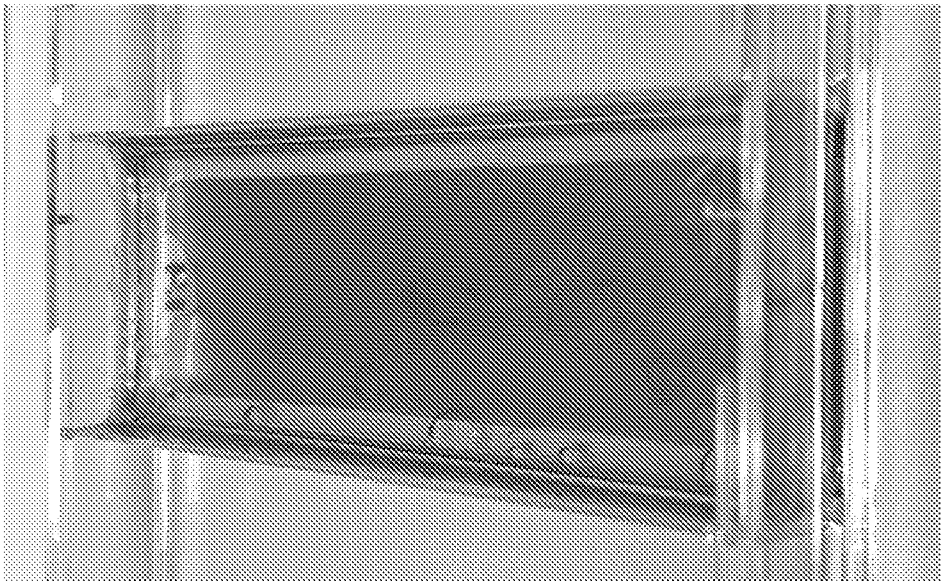
Figure 20:
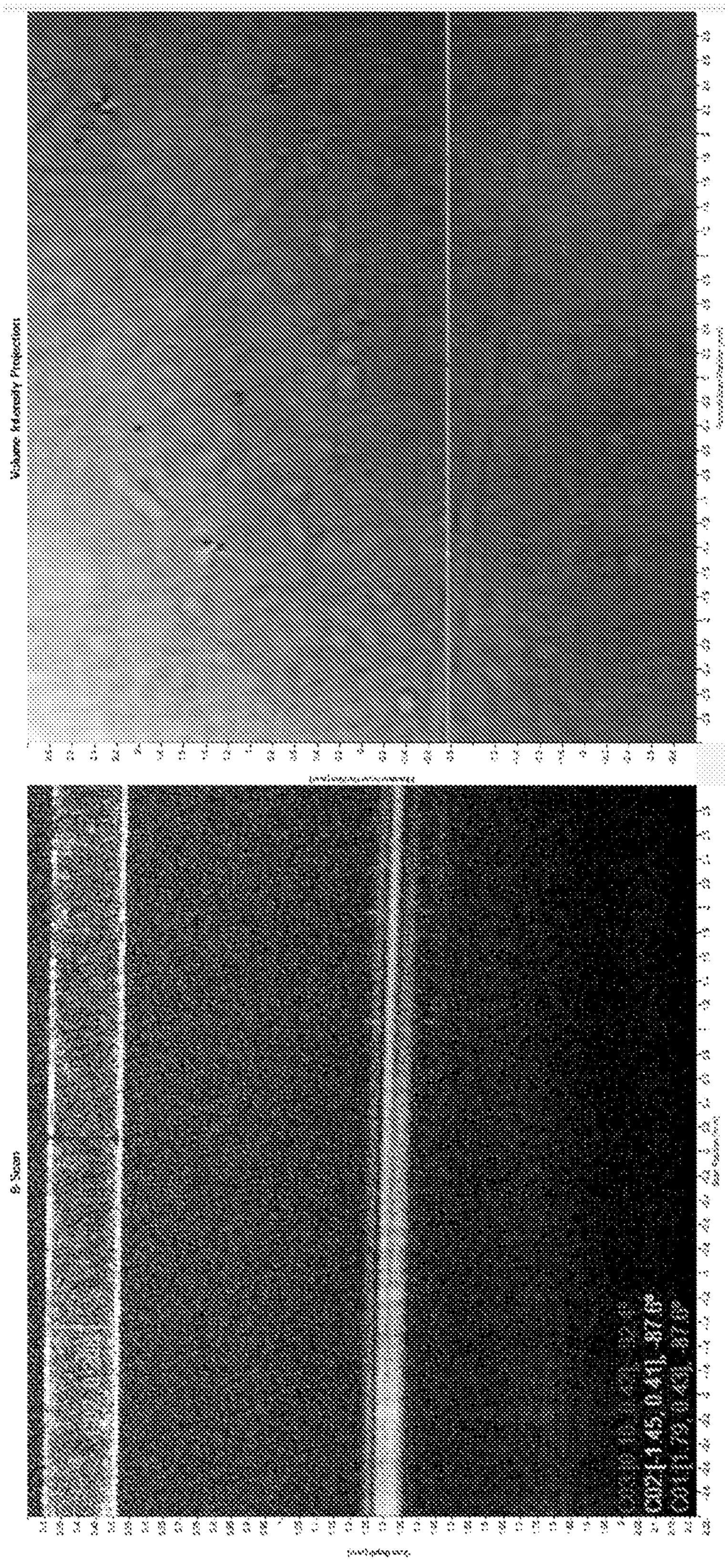
FIG. 20. Representative OCT B-scan and en face (volume intensity projection) of fibrin gel slide. The B-scan shows a smooth top surface of gel with a depth of 208-214 μm.
Figure 21A:
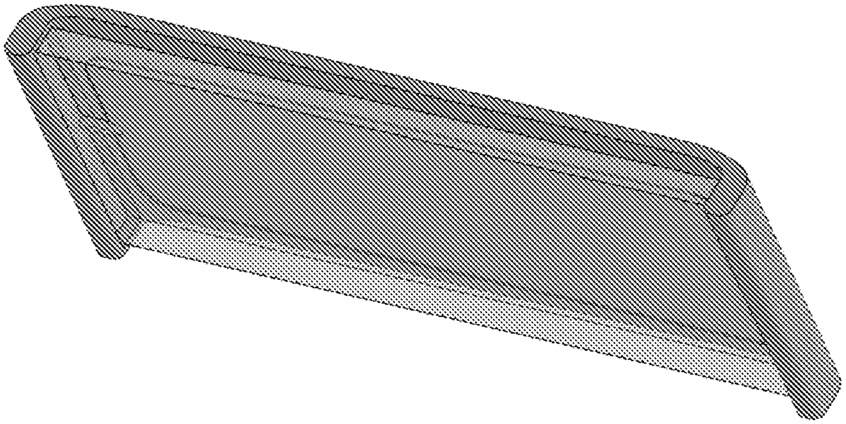
FIGS. 21A-21B. Exemplary fibrin slide plate.
Figure 21B:
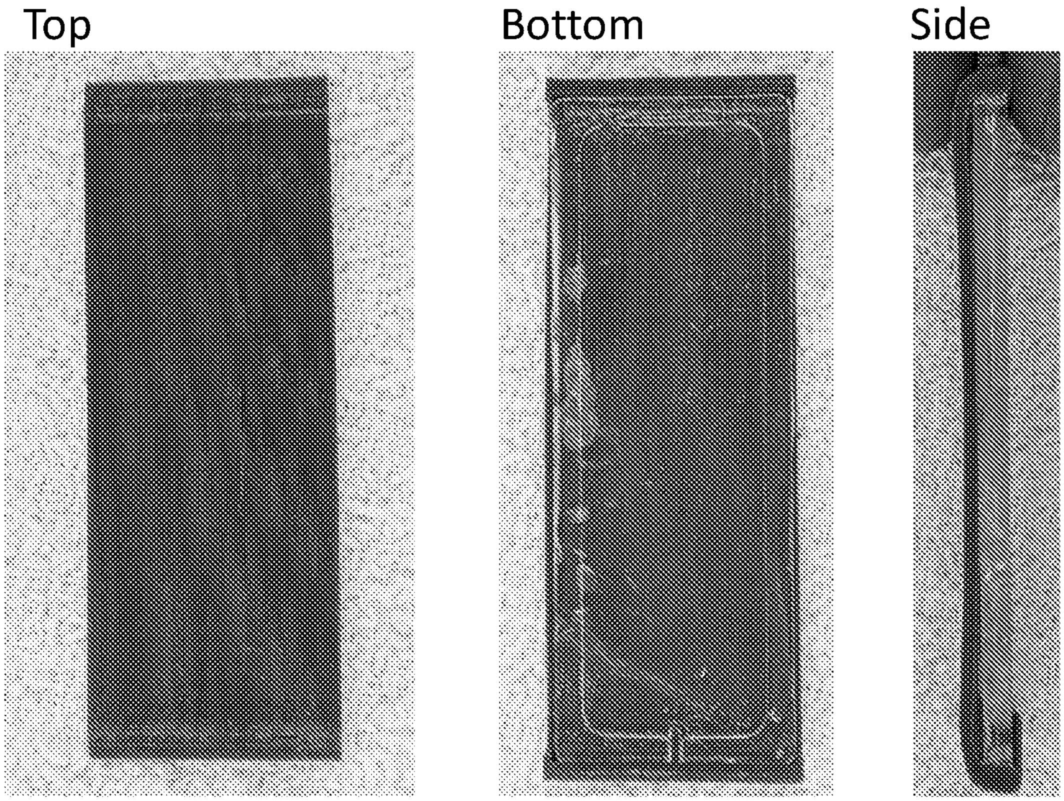

In cases where a fibrin hydrogel provided herein is used for a cell culture application, the fibrin hydrogel can be within (e.g., can be polymerized within) a cell culture container. Examples of cell culture contains that a fibrin hydrogel provided herein can be used within include, without limitation, cell culture dishes, cell culture plates such as multi-well cell culture plates (e.g., 4-well cell culture plates, 6-well cell culture plates, 8-well cell culture plates, 12-well cell culture plates, and 24-well cell culture plates), cell culture flasks (e.g., T25 cell culture flasks, T75 cell culture flasks, T115 cell culture flasks, T125 cell culture flasks, T150 cell culture flasks, and T225 cell culture flasks), custom slide plates, glass slides or coverslips, and transwell-style inserts. In some cases, a cell culture container can be as shown in FIG. 14, FIG. 16, FIG. 17, and/or FIG. 18.

In some cases, a fibrin hydrogel provided herein can be used as a scaffold (e.g., a degradable scaffold) for cell transplantation (e.g., subretinal cell transplantation of stem cells such as hESCs and iPSCs). For example, a fibrin hydrogel provided herein can be used as a scaffold (e.g., a degradable scaffold) to transplant RPE cells (e.g., hESC-derived RPE cells or iPSC-derived RPE cells) into a mammal (e.g., a human) in need thereof (e.g., a mammal, such as a human, having macular degeneration). In some cases, a fibrin hydrogel provided herein can be used as a scaffold for cell transplantation as described elsewhere (see, e.g., United States Patent Application Publication No. 2020/0061246, and US Patent Application Publication No. 2020/0157497).

In some cases, a fibrin hydrogel provided herein can be used as a scaffold (e.g., a degradable scaffold) for tissue engineering applications. For example, a fibrin hydrogel provided herein can be used as a scaffold (e.g., a degradable scaffold) for organs or tissues such as bone, liver, skin, kidney, and cornea. For example, a fibrin hydrogel provided herein can be used as a scaffold (e.g., a degradable scaffold) for wound healing.

In some cases, this document also provides method of using TB, EB, and/or one or more isomers thereof to alter (e.g., slow) polymerization of fibrin within a mammal (e.g., to slow blood clotting within a mammal). In some cases, this document also provides method of using a compound of Formula (I) or Formula (II) such as TB, EB, and/or one or more isomers thereof to alter (e.g., slow) polymerization of fibrin within a mammal (e.g., to slow blood clotting within a mammal). For example, a compound of Formula (I) or Formula (II) such as TB, EB, and/or one or more isomers thereof can be used to slow clot formation (e.g., in vivo clot formation). For example, a compound of Formula (I) or Formula (II) such as TB, EB, and/or one or more isomers thereof can be used to reduce or eliminate thrombi formation (e.g., in diseases such as stroke, myocardial infarction and thrombosis).

Also provided herein are methods for storing (and transporting) a fibrin hydrogel provided herein (e.g., a fibrin hydrogel including one or more fibrin polypeptides, one or more thrombin polypeptides, and TB, EB, and/or one or more isomers thereof). In some cases, also provided herein are methods for storing (and transporting) a fibrin hydrogel provided herein (e.g., a fibrin hydrogel including one or more fibrin polypeptides, one or more thrombin polypeptides, and a compound of Formula (I) or Formula (II) such as TB, EB, and/or one or more isomers thereof). For example, a fibrin hydrogel provided herein can be on a surface of a slide plate (e.g., slides, plates, and molds). In some cases, a fibrin hydrogel on a surface of a slide plate can be packaged in a container (e.g., a pouch). In some cases, two or more (e.g., two, three, four, five, or more) fibrin hydrogel on a surface of a slide plate can be packaged together in a single container (e.g., a pouch).

In some cases, a fibrin hydrogel provided herein (e.g., a fibrin hydrogel including one or more fibrin polypeptides, one or more thrombin polypeptides, and TB, EB, and/or one or more isomers thereof) that is on a surface of slide plate can be covered with a shield plate. In some cases, a fibrin hydrogel provided herein (e.g., a fibrin hydrogel including one or more fibrin polypeptides, one or more thrombin polypeptides, and a compound of Formula (I) or Formula (II) such as TB, EB, and/or one or more isomers thereof) that is on a surface of slide plate can be covered with a shield plate. For example, a shield plate can be attached to (e.g., can be snapped onto, screwed onto, magnetically attached to, or slid onto) a slide plate having a fibrin hydrogel on its surface such that the fibrin hydrogel is between the slide plate and the shield plate. In some cases, a shield plate can protect a surface of the hydrogel from damage.

In some cases, two or more (e.g., two, three, four, five, or more) fibrin hydrogels on a surface of a slide plate can be stacked (e.g., such that the stack alternates slide plates and fibrin hydrogels). For example, when two or more fibrin hydrogels on a surface of a slide plate are stacked, any one or more slide plates within the stack can include a shield attached to the slide plate(s). For example, when two or more fibrin hydrogels on a surface of a slide plate are stacked, a single shield plate can be attached to the stack of slide plates. In some cases when two or more fibrin hydrogels on a surface of a slide plate are stacked, any one or more slide plates within the stack can include one or more grooves on a surface (e.g., the surface opposite the surface having the fibrin hydrogel) of the slide plate (e.g., such that when of two or more fibrin hydrogels on a surface of a slide plate are stacked, the grooved surface of a slide plate can serve as a shield plate).

In some cases, a fibrin hydrogel provided herein (e.g., a fibrin hydrogel including one or more fibrinogen polypeptides, one or more thrombin polypeptides, and TB, EB, and/or one or more isomers thereof) on a surface of slide plate can have an extended shelf life (e.g., as compared to a fibrin hydrogel that is not on a slide plate). In some cases, a fibrin hydrogel provided herein (e.g., a fibrin hydrogel including one or more fibrinogen polypeptides, one or more thrombin polypeptides, and a compound of Formula (I) or Formula (II) such as TB, EB, and/or one or more isomers thereof) on a surface of slide plate can have an extended shelf life (e.g., as compared to a fibrin hydrogel that is not on a slide plate). For example, a fibrin hydrogel provided herein on a surface of slide plate can be stable (e.g., does not degrade and/or lose moisture content) during storage (and transport). In some cases, a fibrin hydrogel provided herein can be packaged in one or more agents that can stabilize the fibrin hydrogel (e.g., one or more anti-fibrinolytic agents such as aprotinin, tranexamic acid, and α-caproic acid). In some cases, a fibrin hydrogel provided herein on a surface of slide plate can be stable for from about 1 day to about 24 months (e.g., from about 1 day to about 18 months, from about 1 day to about 12 months, from about 1 day to about 6 months, from about 1 day to about 3 months, from about 1 day to about 1 month, from about 1 day to about 1 week, from about 1 week to about 24 months, from about 1 month to about 24 months, from about 3 months to about 24 months, from about 6 months to about 24 months, from about 12 months to about 24 months, or from about 18 months to about 24 months). A fibrin hydrogel provided herein can be stable at any appropriate temperature. For example, a fibrin hydrogel provided herein can be stable at from about 4° C. to about 38° C. In some cases, a fibrin hydrogel provided herein can be stable at about 4° C. In some cases, a fibrin hydrogel provided herein can be stable at about 24° C. In some cases, a fibrin hydrogel provided herein can be stable at about 37° C.

The invention will be further described in the following examples, which do not limit the scope of the invention described in the claims.

EXAMPLES

Example 1: Alteration of Fibrin Hydrogel Gelation and Degradation Kinetics Through Addition of Azo Dyes Fibrin is a degradable biopolymer with an excellent clinical safety profile. Use of higher mechanical strength fibrin hydrogels is limited by the rapid rate of fibrin polymerization. The use of higher mechanical strength (fibrinogen concentrations >30 mg/mL) fibrin scaffolds can be used for surgical implantation of cells. However, the rapid polymerization of fibrin at fibrinogen concentrations impairs the ability to scale production of these fibrin scaffolds.

This Example describes the discovery that the azo dye trypan blue (TB) can slow fibrin gelation kinetics allowing for more uniform mixing of fibrinogen and thrombin at high concentrations. A screen of closely related compounds identified similar activity for Evans blue (EB), an isomer of TB. Both TB and EB exhibited a concentration dependent increase in clot time, though EB had a larger effect. While gelation time was increased by TB or EB, overall polymerization time was unaffected. Scanning electron microscopy (SEM) showed similar surface topography, but transmission EM (TEM) showed a higher cross-linking density for gels formed with TB or EB versus controls.

Materials and Methods

Fibrinogen Clotting Assay with Coagulation Analyzer

The effect of various chemical compounds on clotting time was determined. The initial assay was performed with dissolving TB in 1× citrate buffer (20 mM sodium citrate, 100 mM sodium chloride pH 7.4) at the solubility point of TB, 4.58 mM TB concentration. Then, stock solutions of 4.58 mM of a total of 10 different chemical additives (Sigma-Aldrich; St Louis, MO), including TB, EB, polyethylene glycol 1000 (PEG), sodium fluorescein (SF), Bismarck Brown R (BBr), sodium benzene sulfonate (SBS), Congo Red (CR), Alcian Blue (AB), Brilliant Blue R (BB), and indocyanine green (ICG), were prepared in phosphate buffer saline (PBS; Corning). The chemical additives were added to either clinical fibrinogen standards (Stago; Parsippany NJ) or a 1:20 dilution of the Evicel Biologically Active Component 2 (Ethicon), which is a fibrinogen solution (60 mg/mL) and served as the various samples. The same lot of BAC2 was used within each experiment to minimize lot-lot variability.

The Clauss method was used to measure fibrin clotting time. The clotting assay was performed using the Stago STart® Coagulation Analyzer (Stago; Parsippany, NJ) per manufacturer's protocol. The Stago STart uses a mechanical, viscosity-based detection of clotting, independent of sample color and turbidity. Per the protocol, samples were diluted 1:20 in Owren-Koller buffer (Stago) and allowed to equilibrate for 5 minutes at 37° C. Each sample was loaded in a cuvette with a magnetic bead. To start the clotting assay, the thrombin-containing Fibrinogen Assay reagent (Stago) was added to the sample and the clotting was timed by the instrument.

Concentration-dependent effect testing was performed for chemicals that significantly affected clotting time during the screen (TB and EB). Concentrations of 0% (control), 0.01%, 0.05%, 0.1%, 0.2%, 0.3%, and 0.4% w/v dilutions of TB and EB solutions were prepared in PBS. Fibrinogen was then added to the solutions to create a 1:20 dilution sample and the clotting time assay was performed using the coagulation analyzer.

Rheology and Analysis

The viscoelastic mechanical properties of fibrin gels were characterized using oscillatory shear rheology on a Discovery Hybrid Rheometer 2 (TA Instruments; New Castle, DE) with a 20 mm cone-and-plate geometry at a 1° angle and a 20 mm stage. Inertia, friction, and rotational mapping calibrations were performed prior to each experiment. A Peltier temperature-controlled stage maintained 37° C. and a solvent trap was used to control evaporation during experiments lasting longer than 20 minutes. Gels were prepared by mixing specified concentrations of fibrinogen, dye, and thrombin on the stage. Immediately after combining, the geometry head was lowered to 500 μm (~1-3 seconds) before beginning the first experiment. Gelation kinetics were monitored in time sweeps at 1% strain and 10 rad/s angular frequency. Strain sweeps were measured from 0.01-1000% strain at 1 Hz frequency. A frequency sweeps measured from 0.01-3 Hz at 1% strain was used to confirmed fibrin independence of frequency.

Rheometry was performed for samples with no dye (PBS alone), TB, EB, and PEG. Stock fibrinogen (Evicel) was used as is or diluted with PBS. Thrombin was diluted in PBS, with or without the various dyes. To determine the gelation time, a final mixture concentration of 10 mg/mL fibrinogen, 1 U/mL thrombin, and 0.01% w/v dye concentration was used. A time sweep was performed up to 20 minutes, after which some minor effects of evaporation in non-gelled samples introduced noise and could not reliably detect the storage modulus (g'). The gelation time was defined as the point at which the g' exceeded the g" (viscous modulus) and continued to increase over time.

To determine the final polymerization time and resultant shear modulus, a final concentration of 40 mg/mL fibrinogen, 33 U/mL thrombin, and 0.12% w/v dye was used to simulate fibrin scaffold parameters described elsewhere (see, e.g., Gandhi et al., 2018 *Acta Biomater.,* 67:134-46). A time sweep was performed for 2 hours, and the strain sweep was measured following the time sweep to confirm final polymerization had occurred. The shear modulus was determined by averaging values within the linear region of the strain sweep (between 0.01% and 0.5% strain). A 95% confidence interval was defined for the final shear modulus and the lower range value was used as the threshold to determine the final polymerization time.

Electron Microscopy (EM)

Both scanning electron microscopy (SEM) and transmission electron microscopy (TEM) were performed to investigate the effect of the chemical additives on fibril formation microstructure. Gels were made with PBS, TB, or EB as described elsewhere (see, e.g., Gandhi et al., 2018 *Acta Biomater.,* 67:134-46) with the following modifications. Briefly, a mixture of 40 mg/mL fibrinogen, 33 U/mL thrombin, and 0.12% w/v dye final concentrations was plated into a custom acetal mold to create the 300 μm sheet. After a 2 hour incubation at 37° C., the gels were hydrated in PBS for a minimum of 15 minutes.

The gels were then fixed overnight in 2.5% paraformaldehyde and 1% glutaraldehyde in 0.1 M phosphate buffer pH 7 containing 1.0 mM $MgCl_2$ and 0.13 mM $CaCl_2$. After fixation, gels were processed for scanning electron microscopy (SEM). Samples for TEM were processed by initially dehydrating the gels, embedding into plastic resin, and sectioned at a thickness of 100 nm. SEM imaging was performed using a Hitachi S-4700 (Hitachi High Technologies; Schaumburg, IL) microscope. Sections processed for TEM were imaged used a JEOL 1400 microscope (JEOL; Peabody, MA).

Modeling

Modeling was performed using the shear modulus (g') versus time data for each time sweep performed with gels with a final concentration of 40 mg/mL fibrinogen, 33 U/mL thrombin, and 0.12% dye. A biexponential model was used as described elsewhere (see, e.g., Wedgwood et al., *Macromolecular Symposia,* 334:117-25 (2013); and Moreno-Arotzena et al., *Materials* (*Basel*), 8:1636-51 (2015)). The following equation was used:

$$G'(t) = G_1'\left(1 - e^{-\frac{t-x_c}{r_1}}\right) + G_2'\left(1 - e^{-\frac{t-x_c}{r_2}}\right).$$

This equation model assumes a fast (1) and slow (2) kinetic rate. As such $G'_1$ and $G'_2$ are the respective rate associated parameters, $r_1$ and $r_2$ are the respective rates constants, and $X_c$ is a time shift parameter. Modeling was performed using MATLAB (Mathworks; Natick, MA), using the model fit function. Parameters were defined with $r_1 > r_2$ and $x_c$ as positive. Each sample run was best fitted to the model to generate an $r^2 > 0.98$.

Degradation

Fibrin gels were cast as described in the Electron Microscopy section above and hydrated in PBS. A punch was used to generate 5.0 mm×1.5 mm gels. The measured thickness of all the gels was 309±69 μm.

The fibrin gels were then submerged in a PBS solution with 1.6 U/mL plasminogen (Sigma-Aldrich; St Louis, MO) and 17,000 U/mL tissue plasminogen activator (Sigma-Aldrich) in a glass-bottom petri dish (Mattek) and incubated at 37° C. to initiate degradation as described elsewhere (see, e.g., Gandhi et al., 2018 *Acta Biomater.,* 67:134-46). Fibrin gel thickness was monitored over time by imaging with an Envisu R2110 (Leica; Wetzlar, Germany) optical coherence tomograph (OCT) and quantified using the caliper tool within the accompanying InVivoVue software (Leica). Gel thickness was continually measured every 10 minutes until no physical evidence of the insoluble gel remained. The thickness of a gel was measured at 3 different locations (left, middle, right) on each cross-section. The measure at each location was normalized to its initial value and then averaged.

Statistics

All data is provided as average±standard deviation. Data was analyzed using JMP 14 (SAS; Cary, NC). For coagulation analyzer assay of citrate and citrate+TB and rheometry for TB and EB gel time, a student's T-test was used. For all other analysis, a 1-way ANOVA test was used. After ANOVA analysis, significance was tested amongst groups using a Tukey HSD test. Statistical significance was considered for $p<0.05$.

Results

Screen for Chemical Compounds that Alter Fibrin Gelation Kinetics

Figure 3A:
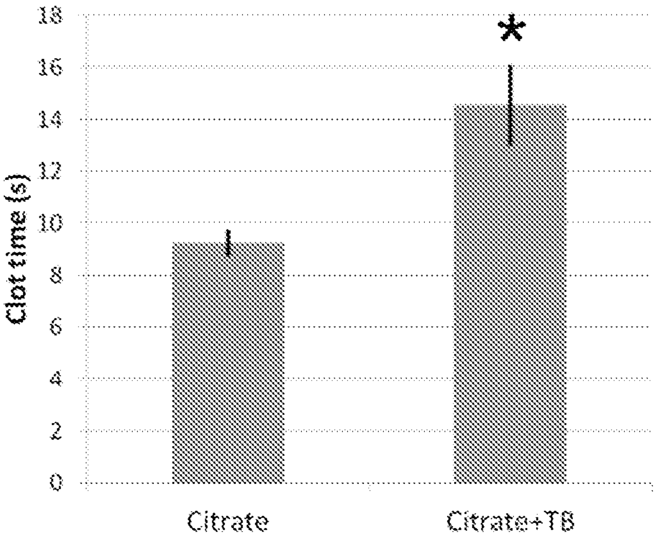
FIGS. 3A-3C. Clotting times for fibrin gels formed with various chemical compounds. A coagulation analyzer was used to determine clot formation time.

In efforts to improve the visibility of fibrin gels during surgical implantation, it was observed that the inclusion of TB in the gelation mixture improved handling of the liquid phase of the gelation reaction. To determine whether TB alters gelation kinetics, the clotting time of a fibrin was examined gel using a coagulation analyzer. A coagulation analyzer is a specialized clinical instrument that is used to quantify fibrinogen concentrations in patient blood samples via the Clauss Method (Clauss, *Acta Haematol.,* 17:237-46 (1957)). This method follows the time it takes for a mixture of fibrinogen and thrombin to initially clot. The coagulation analyzer chosen for this work utilizes mechanical detection, instead of the more common optical detector system, due to potential interaction with the use of various color dyes. A clinical standard from the manufacturer was used to test if adding TB would alter gelation kinetics. Samples diluted in only 1× citrate buffer (20 mM sodium citrate, 100 mM sodium chloride pH 7.4) had a gelation time of 9.2±0.4 seconds and samples diluted in citrate+TB had a slower gelation time of 14.6±1.5 seconds (average±sd, n=8, $p<0.001$) (FIG. 3A).

Figure 2:
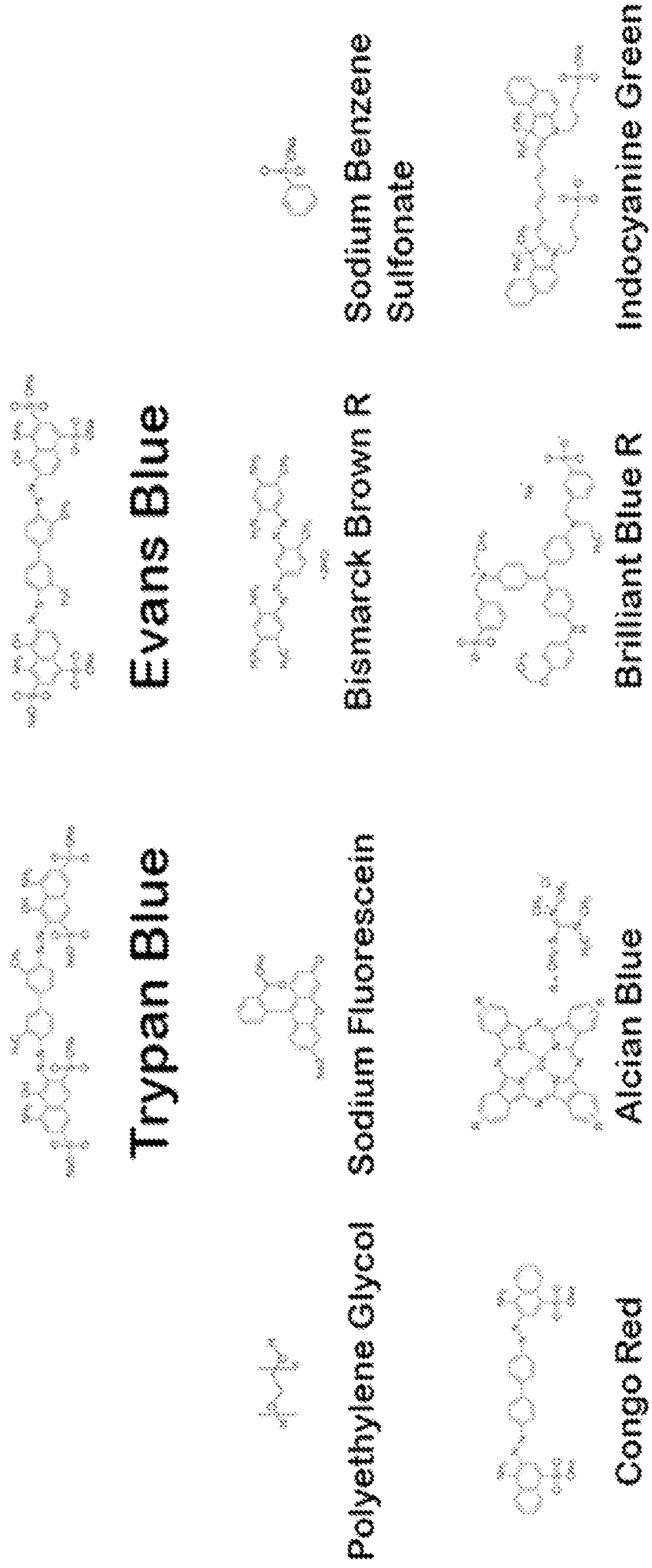
FIG. 2. Chemical structures of screened compounds. TB is classified as an azo dye; a central benzidine structure interconnects mirrored structures of an azo bond to a napthalene backbone with an amine, an alcohol, and two sulfonate functional groups each. Evans blue (EB) is a position isomer of TB, with the sulfonates at slightly different locations along the naphthalene group. Polyethylene glycol (PEG) 1000 mimics the same size without charge or functional groups. Sodium fluorescein (SF) is an unrelated dye. Bismarck Brown (BBr) contains azo and amine groups. Sodium Benzene Sulfonate (SBS) contains a sulfonate group and similar charge. Congo Red (CR) contains azo, sulfonate, benzidine, and amine groups. In fact, the only major difference between CR and TB is that CR contains a total of 2 sulfonate groups and TB has 4. Alcian Blue (AB) is a blue dye with unrelated chemistry or size. Brilliant Blue R (BB) is a similarly sized non-azo dye with sulfonate and amine groups. Indocyanine green (ICG) is a dye with sulfonate and amine groups.
Figure 3B:
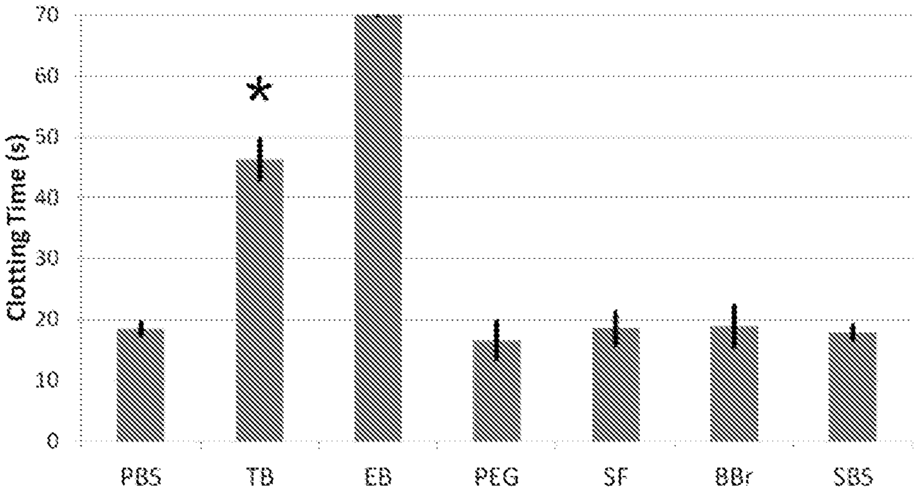
Figure 3C:
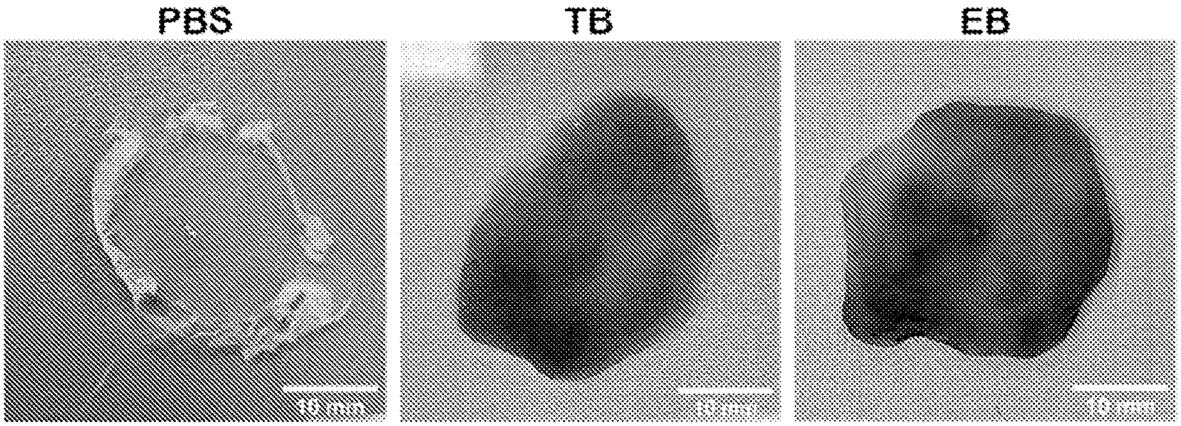

To better understand how TB alters gelation kinetics and to identify other small molecules that may perform better at slowing fibrin gelation kinetics, a screen of related chemical compounds was performed. The composition of the chemical library screened was based on properties of TB, including molar size, charge, and functional groups within its chemical structure. Table 1 lists the chemical agents selected for screening, the structures of which are summarized in FIG. 2. The screen was performed using the coagulation analyzer but, rather than using a clinical standard, fibrinogen and thrombin sourced from tissue glue was used at a fixed concentration. All agents were tested at multiple concentrations up to a maximum of 4.58 mM (the solubility point of TB), with the exception of sodium benezene sulfonate (SBS), which was also tested at 18.32 mM to match the total charge of TB. Congo red (CR), alcian blue (AB), brilliant blue (BB), and indocyanine green (ICG) each repeatedly caused protein precipitation during the assay and were excluded from further analysis (Table 1). The gelation times for the remaining compounds, were 18.4±1.0 sec for controls (PBS), 46.3±3.2 sec for TB, >70 sec for EB, 16.6±3.0 sec for PEG, 18.5±2.6 sec for SF, 18.9±3.3 sec for BBr, and 17.8±1.1 sec for SBS, (n=10, $p<0.001$) (FIG. 3B). According the post-hoc Tukeys HSD test, TB was statistically different from all other groups ($p<0.001$). EB tested greater than 70 seconds on each trial, beyond the detection limit of the analyzer, but fibrin containing EB was manually confirmed to have gelled after the assay was completed. Although EB extended gelation time beyond the ability of our instrument to measure accurately, the lack of an accurate clot time for EB caused us to exclude it from the statistical analysis. These data demonstrate that TB and EB alter gelation kinetics of fibrin but that this is not a generalized property of related compounds.

TABLE 1

Chemical compounds investigated in a screen for effect on fibrin clotting time.

| Chemical | Molar Mass (g/mol) | Charge | Chemistry: Azo | Sulfonate | Benzidine | Amine | Effect on Clotting Time |
|---|---|---|---|---|---|---|---|
| Trypan Blue (TB) | 960.81 | 4− | x | x | x | x | Increase |
| Evans Blue (EB) | 960.81 | 4− | x | x | x | x | Increase |
| Polyethylene Glycol (PEG) 1000 | 950-1050 | 0 | | | | | No effect |
| Sodium Fluorescein (SF) | 376.27 | 2− | | | | | No effect |
| Bismarck Brown R (BBr) | 461.39 | 0 | x | | | x | No effect |
| Sodium Benzene Sulfonate (SBS) | 180.16 | 1− | | x | | | No effect |
| Congo Red (CR) | 696.66 | 2− | x | x | x | x | Precip |
| Alcian Blue (AB) | 1298.86 | 4+ | | | | | Precip |
| Brilliant Blue R (BB) | 825.97 | 1− | | x | | x | Precip |
| Indocyanine Green (ICG) | 774.96 | 1− | | x | | x | Precip |

The Effects of TB and EB are Dose Dependent

Figure 4A:
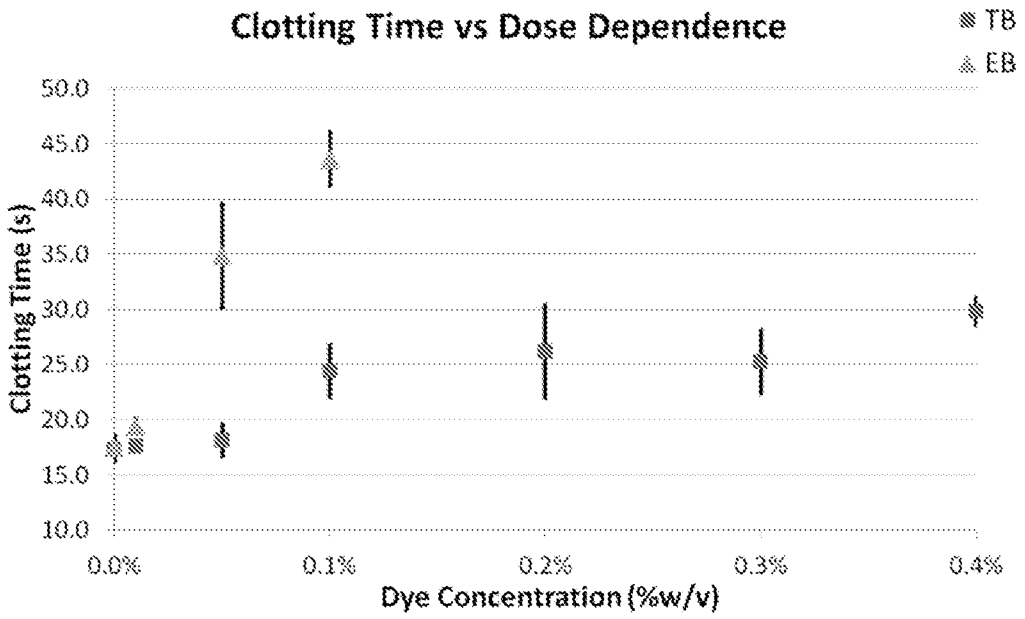
FIGS. 4A-4B. Concentration variation effects on fibrin clotting time.

As TB and EB appeared to have an effect on clotting time, the concentration of the added dye was varied to see if a relationship existed with to clotting time using the clotting assay described in the previous section with tissue glue as the source of fibrinogen and thrombin. As shown in FIG. 4A, clotting time for gels without dye (0% w/v) was 17.5±1.1 seconds (n=10). Clotting times for gels made with 0.010%, 0.05%, and 0.10% (w/v) EB were 19.4±0.7, 34.8±4.7, and 43.6±2.5 seconds (n=10), respectively. Clotting was observed for gels made with 0.2-0.4% EB, but the clotting time was >70 seconds and thus out of the range of detection of the coagulation analyzer. Clotting times for gels made with 0.01%, 0.05%, 0.10%, 0.2%, 0.3%, and 0.4% (w/v) TB were 17.6±0.3, 18.1±1.4, 24.4±2.3, 26.2±4.2, 25.2±2.9, and 29.8±1.2 seconds (n=10), respectively. Increasing dye concentration relative to fibrinogen concentration results in an increase in clotting time.

Figure 4B:
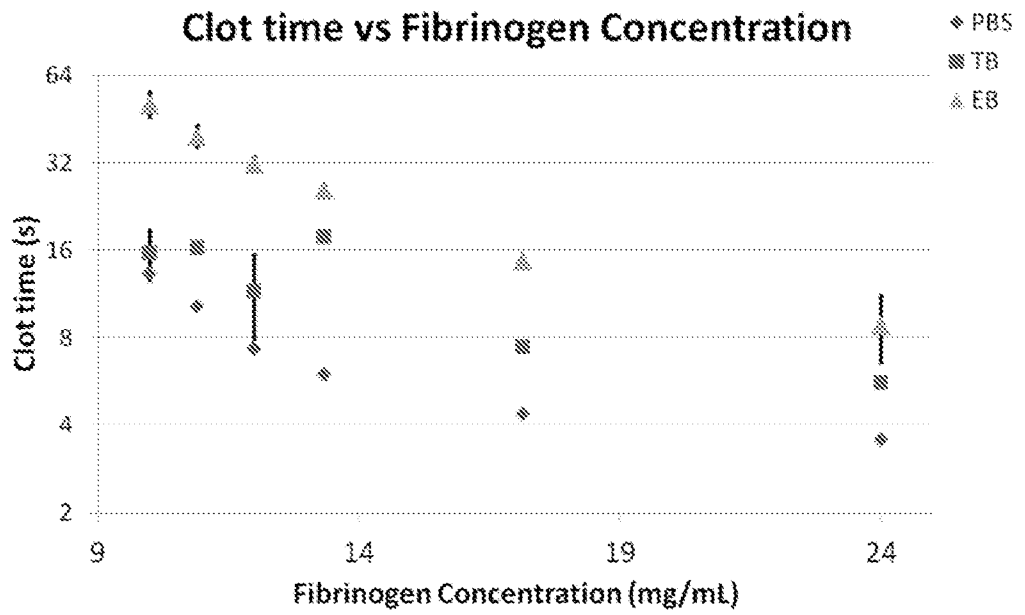

To examine the effect of TB or EB on gelation kinetics is independent of fibrinogen concentration, fibrinogen concentration was varied while keeping dye concentration fixed at 0.1% w/v and the clotting time determined (FIG. 4B). At a fibrinogen concentration of 10.0 mg/mL, the clot time for PBS, TB and EB were 13.3±0.3, 15.7±3.1, and 50.9±4.9 seconds, respectively. At a fibrinogen concentration of 10.9 mg/mL, the clot time for PBS, TB and EB were 10.3±0.2, 16.3±0.4, and 39.5±3.3 seconds, respectively. At a fibrinogen concentration of 12.0 mg/mL, the clot time for PBS, TB and EB were 7.3±0.2, 11.6±3.7, and 31.7±1.8 seconds, respectively. At a fibrinogen concentration of 13.3 mg/mL, the clot time for PBS, TB and EB were 6.0±0.3, 18.1±0.4, and 25.7±1.0 seconds, respectively. At a fibrinogen concentration of 17.1 mg/mL, the clot time for PBS, TB and EB were 4.4±0.1, 7.4±0.1, and 14.8±0.4 seconds, respectively. Finally, at a fibrinogen concentration of 24.0 mg/mL, the clot time for PBS, TB and EB were 3.6±0.1, 5.6±0.1, and 8.9±2.3 seconds, respectively. All three group trends confirm the inverse relationship between clotting time and fibrinogen concentration, as predicted by the Clauss method. The dyes appear to maintain their increased clot time independent of the fibrinogen concentration.

Gelation Kinetics at Lower Fibrinogen Concentrations Determined by Rheometry

Rheometry was used to confirm findings obtained using the coagulation analyzer and test conditions at higher fibrinogen concentrations used in high mechanical strength scaffolds. While clotting time and gelation time are similar properties, the terms are utilized discretely due to the differences in the respective assays. However, in controls for gels at higher fibrinogen concentrations, thrombin concentrations were decrease by orders of magnitude to assess initial gel time based on the sensitivity of the rheometer. In order to consistently detect a gelation time, when the g' value (shear modulus) becomes greater than the g" value (viscous modulus), conditions were set to 10 g/mL fibrinogen and 1 U/mL thrombin final concentration using tissue glue for all samples. Sample conditions tested using rheometry included use of PBS (control), TB, EB, or PEG solution to dilute the thrombin so that the final gel concentration of the dye was 0.01% w/v. For EB samples with higher dye concentration, the gelation time was too long to detect reliably due to evaporative effects, even when using a solvent trap. However, gel properties were confirmed mechanically after allowing the mixture to sit. PEG was used as a negative control in addition to PBS due to potential molality effects.

Figure 5A:
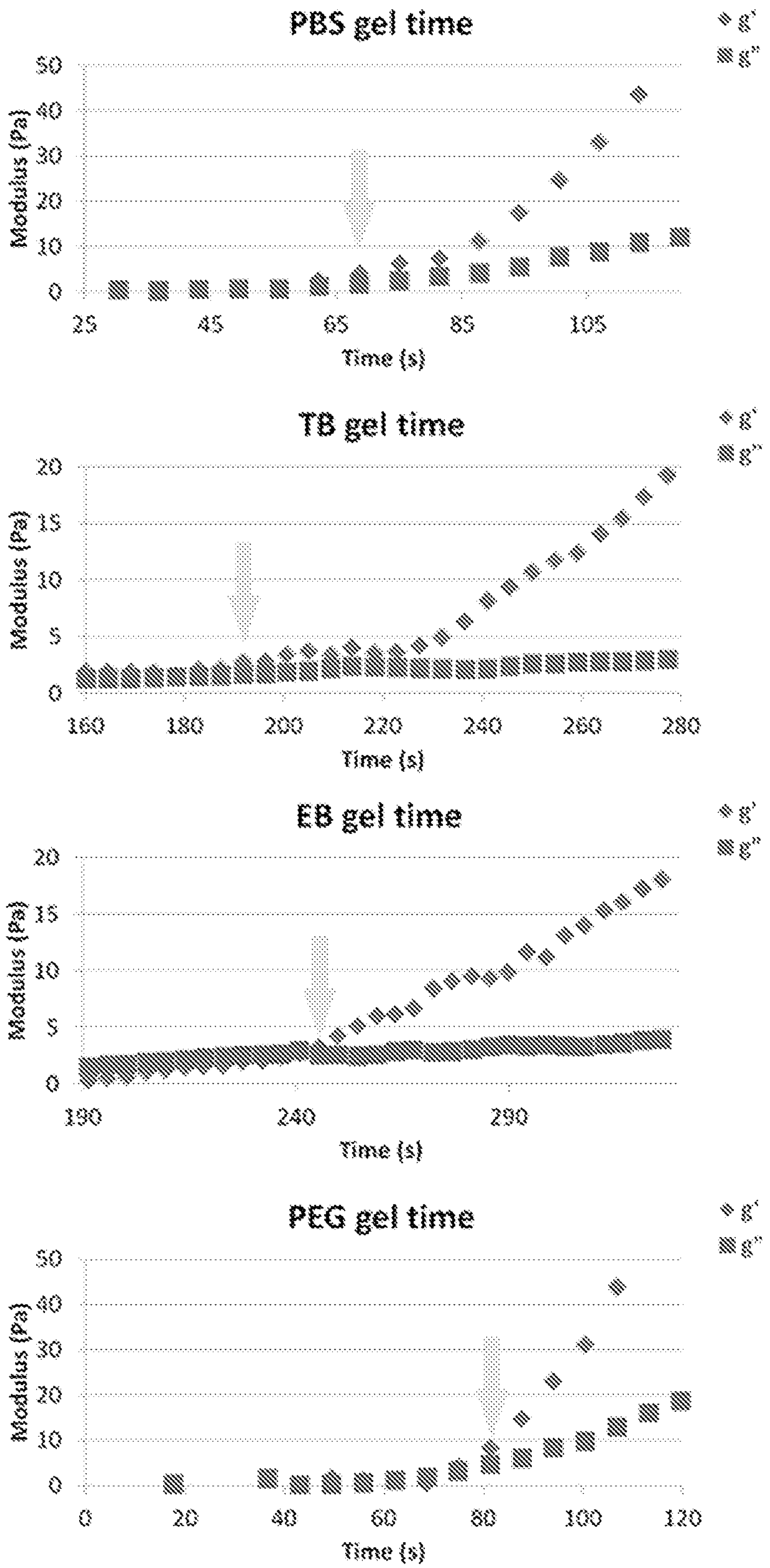
FIGS. 5A-5B. Rheometry investigation of initial gelation time of fibrin gels with added dye. A rheometer was used to assess gelation parameters.
Figure 5B:
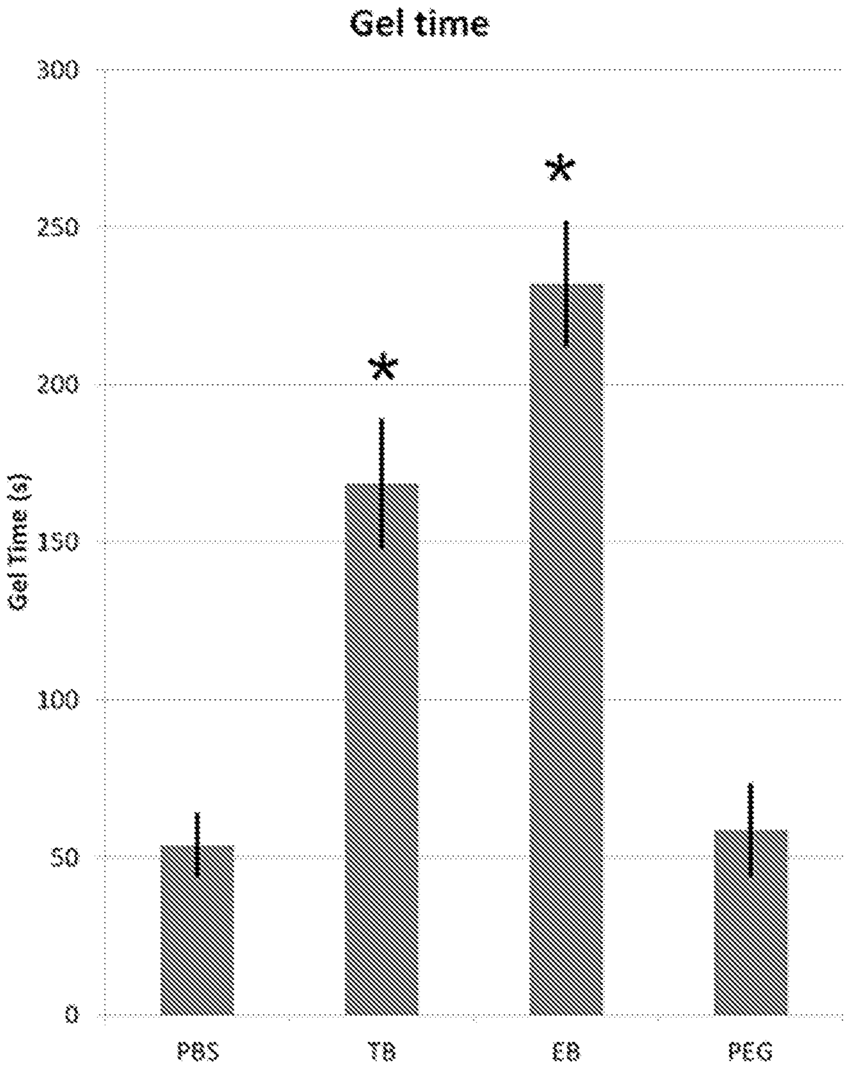

Overall, all four test samples showed somewhat similar trends in rheometry measurements, albeit at different time scales. Initially, g' and g" values were on the same scale (<2 Pa). While there were individual data points that reported a g' value greater than g", the values were considered background as compared to conditions tested without thrombin (no gelation initiated). Due to this, the gelation time was calculated as when the g' values exceeded the g" value and continued to grow over time (arrow, FIG. 5A). All four test samples showed a clear point at which the g' value began to increase over time relative to the g" value (FIG. 5A). Samples with PBS and PEG showed an exponent growth of g' once gelation once initiated, while TB and EB showed a more gradual growth once gelation was initiated followed by more exponential growth. Samples containing PBS resulted in a gelation time of 53.8±9.7 seconds (FIG. 5B). Samples containing TB resulted in a gelation time of 168.7±19.9 seconds. Samples containing EB resulted in a gelation time of 232.1±19.3 seconds. Samples containing PEG resulted in a gelation time of 58.5±14.4 seconds. Statistically, there was significant trend (n=3, $p<0.001$). Within groups, the TB group was significantly different from the PBS and PEG groups ($p<0.001$) and EB group ($p=0.006$), while the EB group was significantly different from the PBS and PEG groups ($p<0.001$). The PBS and PEG groups were not different ($p=0.98$).

Figure 6:
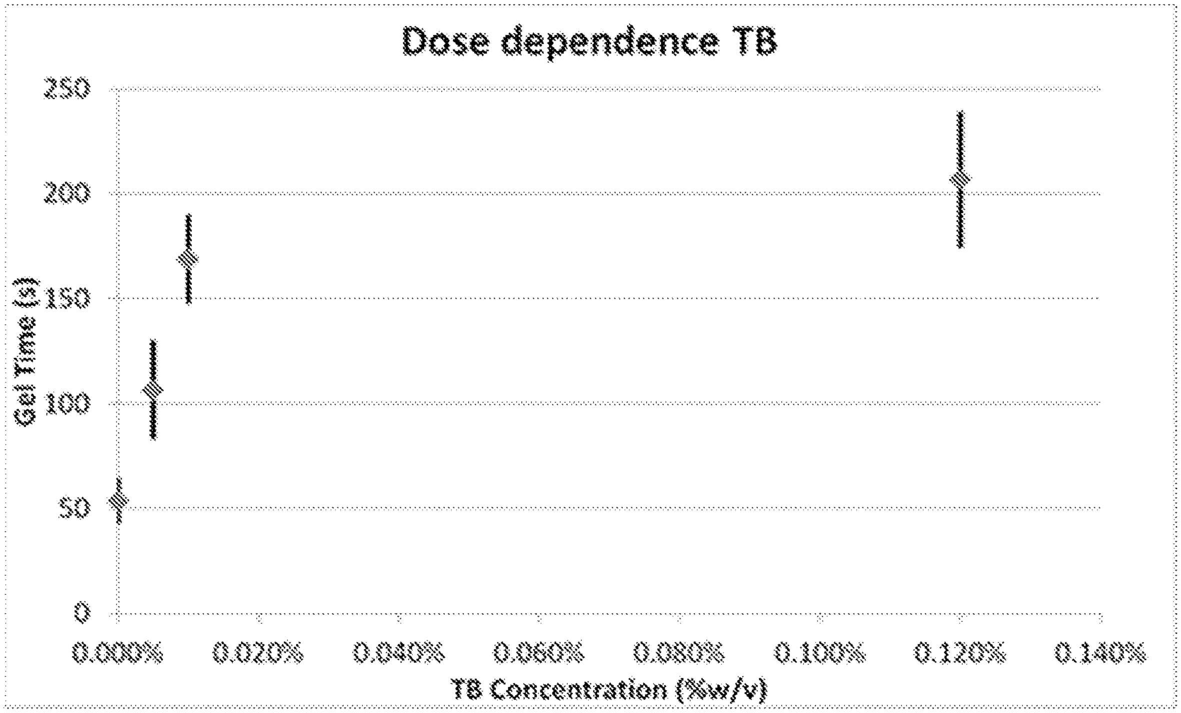
FIG. 6. Graph showing gelation time at various concentrations of TB under rheology experiments. Fibrin gels were made with 10 mg/mL fibrinogen and 1 U/mL thrombin final concentration. TB concentrations (% w/v) represent final gel mixture concentrations. These data confirm previously established dose dependence in FIG. 2 by a second method.

Testing TB at various dye concentrations confirmed the previously established dose dependent relationship between dye concentration and gelation time (FIG. 6). At TB concentrations of 0%, 0.005%, 0.01%, and 0.12% w/v the gelation times were 53.8±9.7, 106.4±22.5, 168.7±19.9, and 206.7±31.3 seconds (n=3).

Gelation Kinetics at Higher Fibrinogen Concentrations Determined by Rheometry

With confirming that both TB and EB, but not PEG, cause a substantial increase in gelation time, polymerization time was measured. The polymerization time is the total time for the hydrogel to fully form with no remaining soluble fibrin monomer. Functionally, this is defined as the point at which the shear modulus no longer changes. Quantitatively, this is defined at the point at which the g' reaches its maximum and plateaus over time.

To test if the inclusion of TB and EB would alter the polymerization time, the previous rheometry setup was used over a longer range of time. Unfortunately, evaporative effects were detected as early as 2 hours. At the 10 mg/mL fibrinogen, 1 U/mL thrombin concentration, the PBS group did not gel within the 2 hours and evaporative effects were visualized in the set up with the gel shrinking over time. When the top plate was removed, mechanical manipulation of the gel showed that the polymerization was not complete, with presence of liquid pools. The surface was sticky, and the presence of non-cross-linked fibrin was evident. To measure polymerization time reliably, the fibrinogen and thrombin concentrations were increased. A 40 mg/mL fibrinogen and 33 U/mL thrombin final concentration is capable of fully polymerizing within 2 hours (see, e.g., Gandhi et al., *Acta Biomater.,* 67:134-46 (2018)). As such, the rheometry experiment were repeated at these concentrations. A final concentration of 0.12% w/v for TB, EB and PEG was used.

Figure 7A:
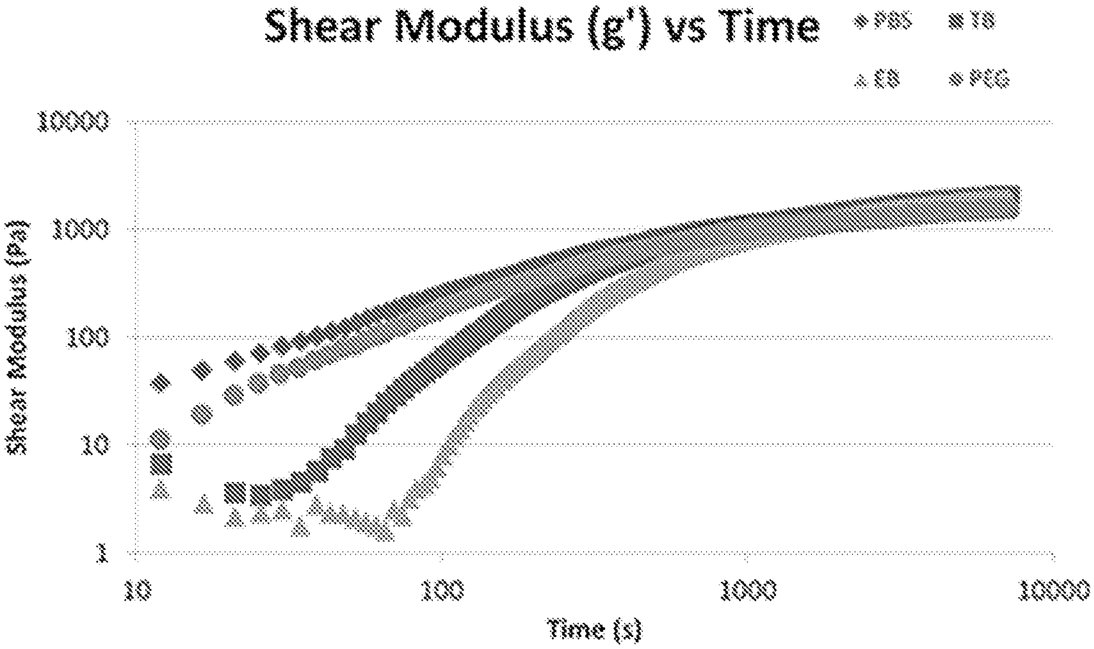
FIGS. 7A-7C. Shear modulus of higher fibrinogen concentration gels.
Figure 7B:
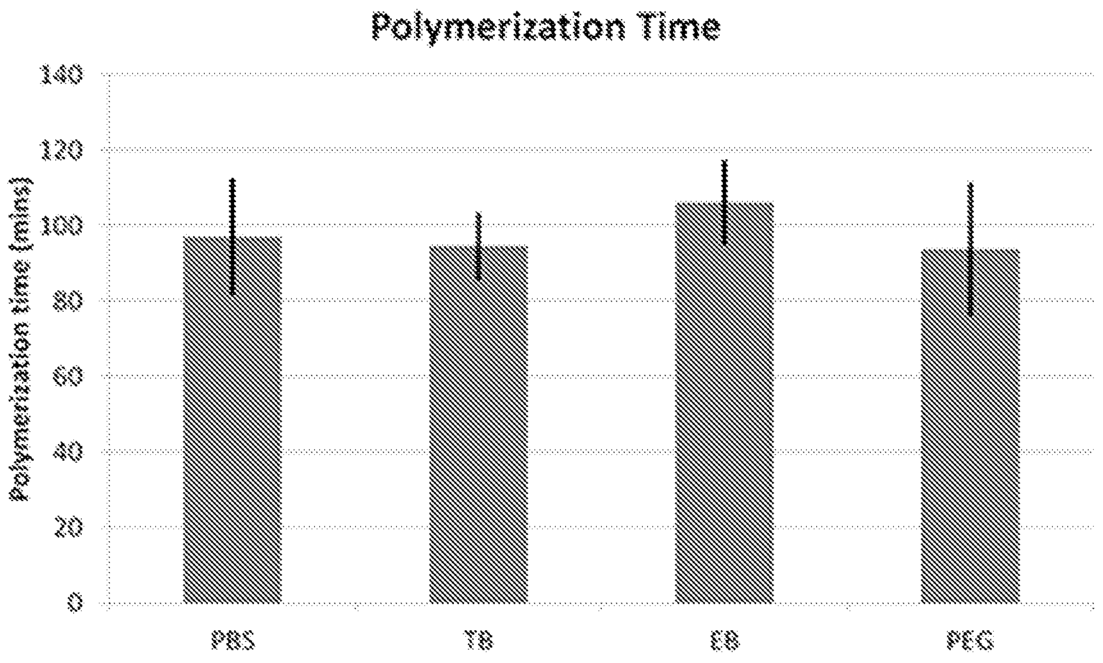
Figure 7C:
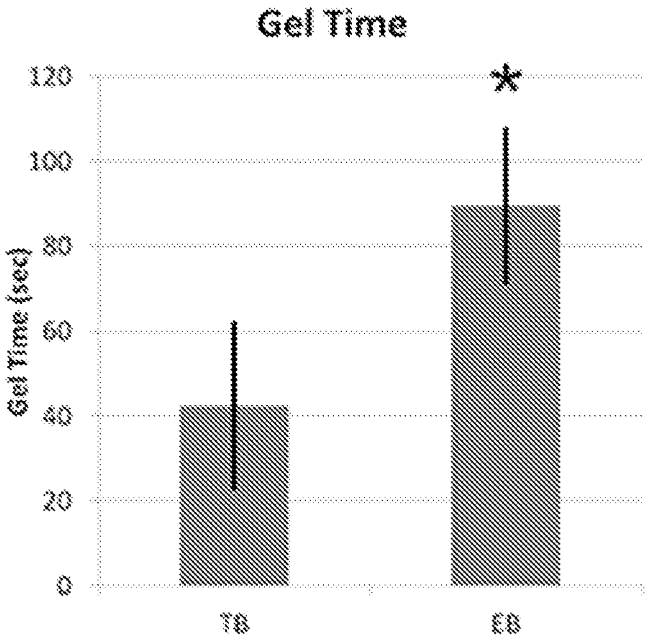

At these higher fibrinogen and thrombin concentrations, both TB and EB continue to have an effect on gelation time. This can be visualized on the log (g') vs log (time) graph (FIG. 7A) with the TB and EB groups showing initial gelation after a shifted time delay (FIG. 7B). At these higher concentrations, gels made with TB resulted in a gelation time of 42.4±19.4 seconds and EB of 89.6±17.9 seconds, a significant difference (n=3, $p=0.037$) (FIG. 7C).

Figure 8A:
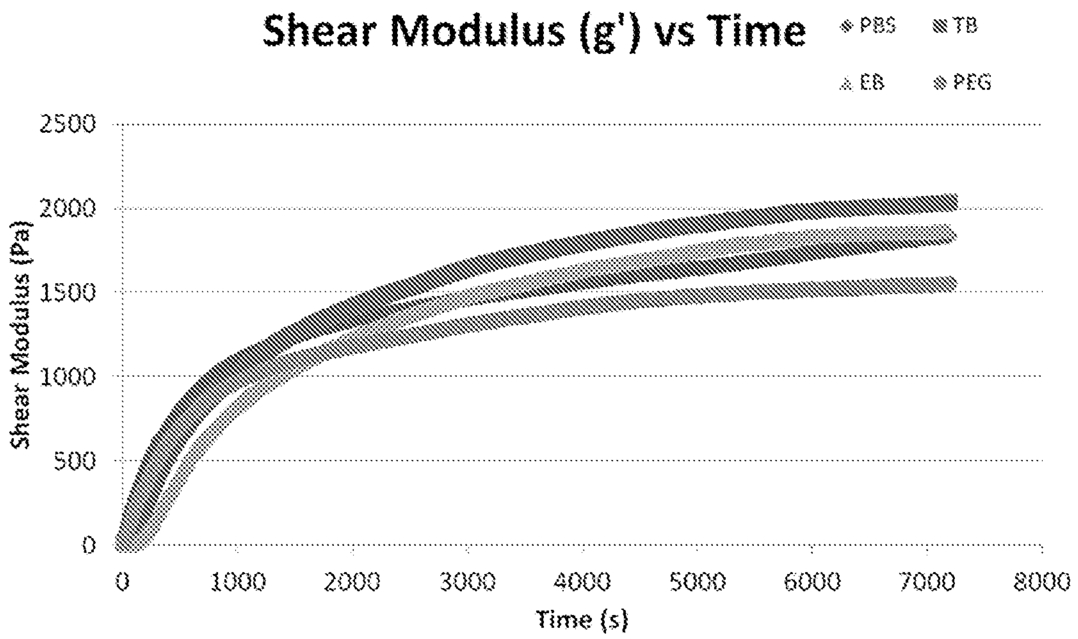
FIGS. 8A-8B. Shear Modulus higher fibrinogen concentration gels.
Figure 8B:
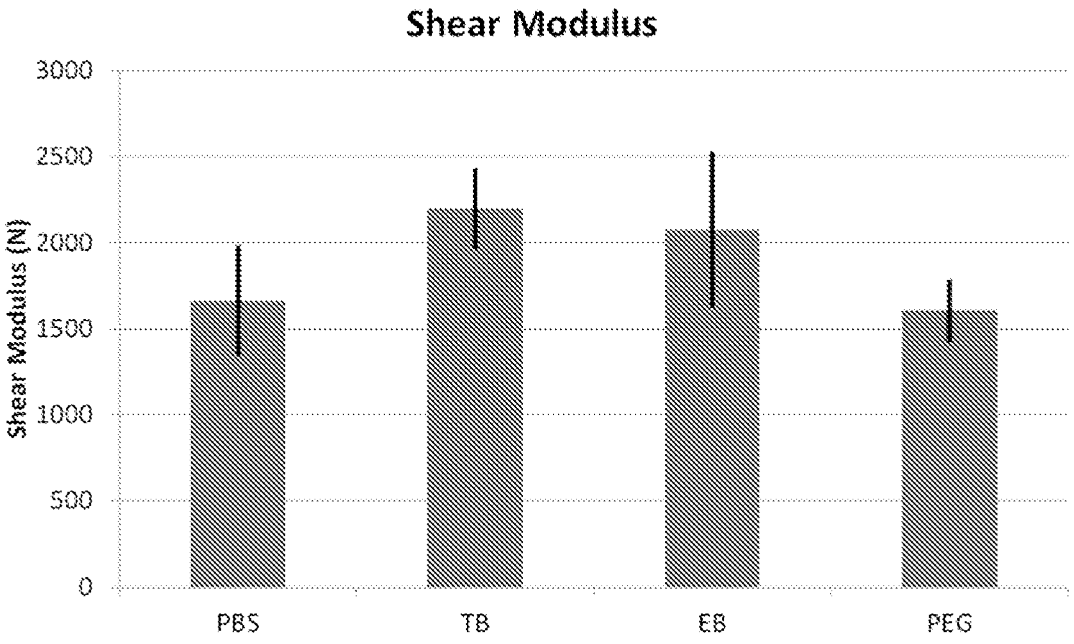

Similar to the previous experiment, the shear modulus (g') showed growth over time for all four conditions (FIG. 8A). Both PBS and PEG groups show g' values greater than g" values at the first detectable time point (12 seconds), showing that both groups had already past the initial gelation time. TB and EB show a delay in gelation but appear to quickly approach the PBS and PEG groups. Near the 1000 sec mark, all four groups appear to show a similar growth of g' overtime. A strain sweep was measured at the end of the time sweep to confirm that the gel had completed polymerization within the 2 hour time frame. Shear modulus values from the linear portion of the strain sweep were verified with rheological data described elsewhere (see, e.g., Wedgwood et al., *Macromolecular Symposia,* 334:117-25 (2013); and Moreno-Arotzena et al., *Materials* (*Basel*), 8:1636-51 (2015)), and used to determine the final gel shear modulus. Using this shear modulus value, the polymerization time for each sample was calculated. The polymerization times for PBS, TB, EB, and PEG groups were 97.0±14.9, 94.6±8.3, 106.2±10.7, 93.8±17.0 minutes (n=3, p=0.654) (FIG. 8B). These data conclude that the inclusion of TB or EB did not alter the final polymerization time.

Rheometry Shear Modulus

Shear modulus (g') is often accepted as an indicator of the mechanical properties of a fibrin hydrogel, with higher shear modulus values indicating a stronger or stiffer gel. In the time sweep data, shear modulus grows over time with initial exponential growth, followed by a swift plateau (FIG. 8A). FIGS. 7A and 8A show the same data, but FIG. 7A uses log scales and FIG. 8A does not to visualize the differences between groups. A strain sweep was measured at the end of the time sweep for the high concentration gels to obtain a final shear modulus. The strain sweep confirms the plateau as the final shear modulus (g'). The final shear moduli (g') for PBS, TB, EB, and PEG groups were 1664±308, 2197±221, 2077±441, and 1606±169 Pa (FIG. 8B). While TB appears to be greater than PBS and PEG controls, there is no statistically significant result (n=3, p=0.089).

Modeling Kinetics

Figure 9A:
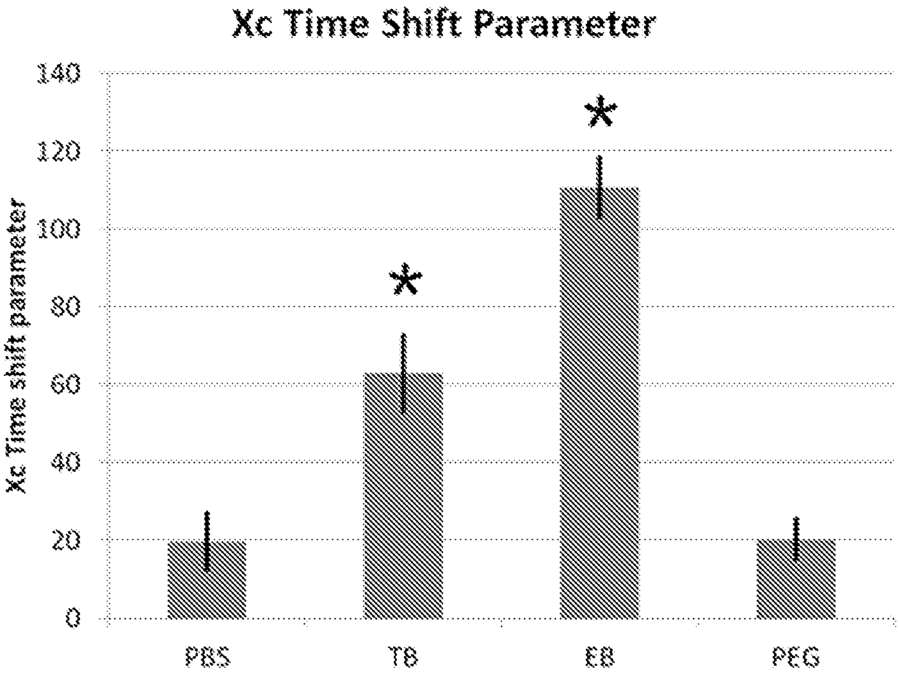
FIGS. 9A-9B. Fibrin gel shear modulus data modeling parameters.
Figure 9B:
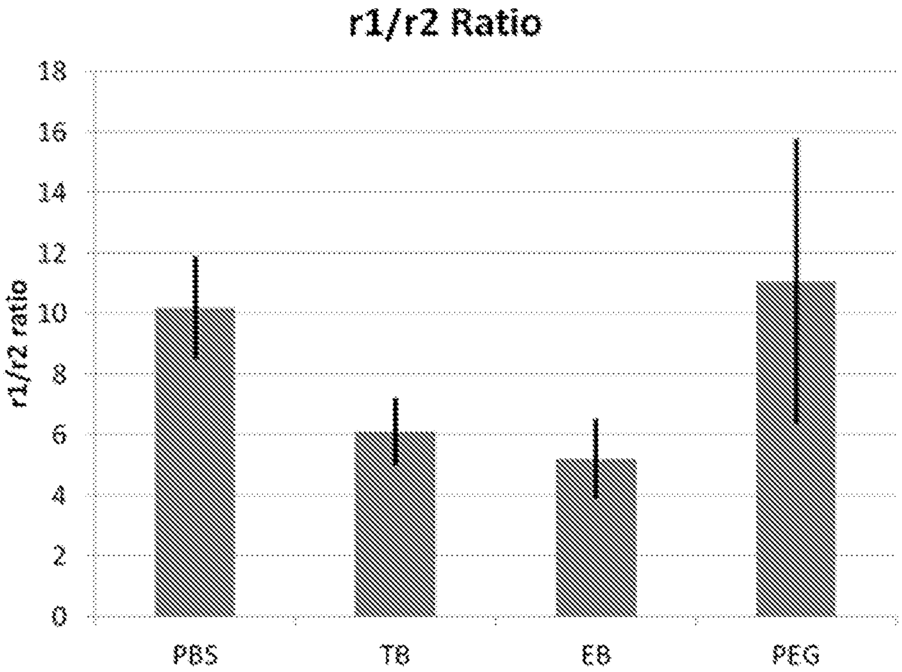

Previous work has fitted fibrin gelation kinetics to a biexponential model (see, e.g., Moreno-Arotzena et al., *Materials* (*Basel*), 8:1636-51 (2015)). In this model, gelation, as measured by the shear modulus over time, consists of a fast and slow reaction rate. Each time sweep series was fitted to the biexponential model to determine the fast (1) and slow (2) associated parameters, reaction rates and time shift parameter (Table 2 and FIG. 9). The time shift parameters ($x_c$) for the PBS, TB, EB, and PEG groups were 19.7±7.2, 62.9±9.7, 110.6±7.6, and 20.3±5.0 sec (n=3, p<0.001) (FIG. 9A). Within groups, all groups were significantly different from each other (p<0.001), except between the PEG and PBS groups (p=0.999). This re-affirms the shifted delay in gelation onset for TB and EB groups and confirms that the effect is not due to changes in molality. To understand if there is a change in reaction rates, the ratio of the fast to slow reaction rate was compared. The ratios, r1/r2, for PBS, TB, EB and PEG groups were 10.2±1.6, 6.1±1.0, 5.2±1.2, and 11.0±4.6 second$^{-1}$ (n=3, p=0.057) (FIG. 9B). These data suggest there may be a change in the reaction rates, though the data are not significant.

TABLE 2

Modeling parameters yielded from fitting shear modulus (g') versus time (t) data for the various investigated groups using a biexponential model (avg ± sd, n = 3).

$$G'(t) = G'_1\left(1 - e^{\frac{t-x_c}{r_1}}\right) + G'_2\left(1 - e^{\frac{t-x_c}{r_2}}\right)$$

| | PBS | TB | EB | PEG |
|---|---|---|---|---|
| $G'_1$ | 1020 ± 525 | 1555 ± 92 | 927 ± 395 | 880 ± 467 |
| $G'_2$ | 822 ± 98 | 800 ± 186 | 787 ± 210 | 895 ± 233 |
| $x_c$ | 20 ± 7 | 63 ± 10 | 111 ± 8 | 20 ± 5 |
| $r_1$ | 3287 ± 295 | 2679 ± 366 | 3720 ± 732 | 3707 ± 1120 |
| $r_2$ | 325 ± 26 | 455 ± 131 | 739 ± 205 | 345 ± 37 |

Electron Microscopy Imaging

To detect microstructure changes within gels made of TB and EB, both scanning (SEM) and transmission electron microscopy (TEM) were performed on high concentration gels made with a custom mold. Fibrin gels made with PBS appeared to have an unanticipated surface topography, with significant fibril alignment to create a smoother surface with crater-like mesh voids. As this was unanticipated, SEM was performed on PBS fibrin gels without the mold. These gels appeared as a random network of varying diameter fibrils cross-linked to create a mesh.

Figure 10:
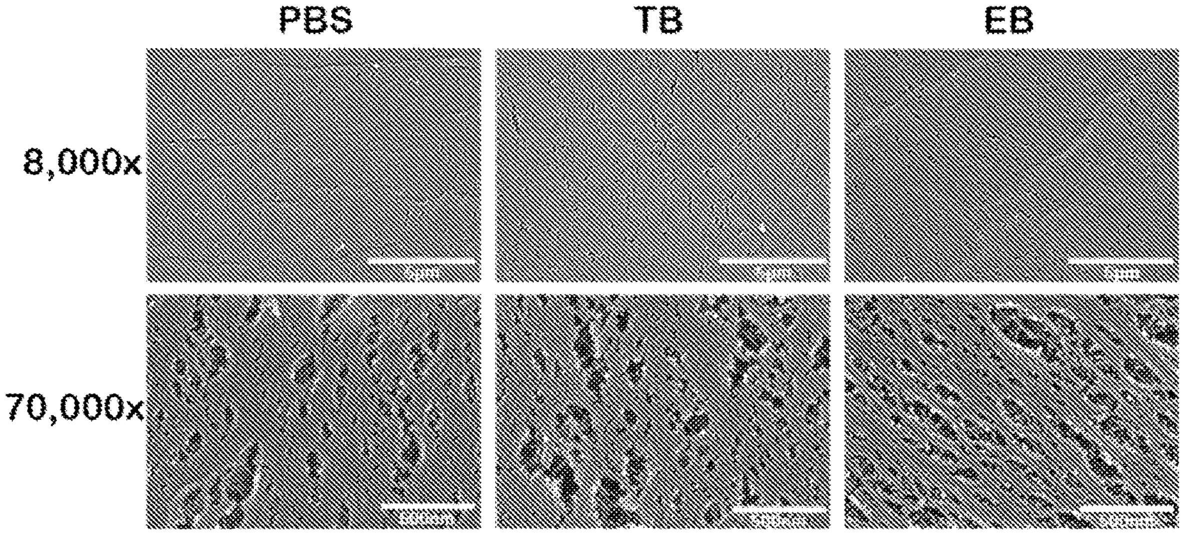
FIG. 10. Representative scanning electron microscopy (SEM) photomicrographs of fibrin gels made of 40 mg/mL fibrinogen, 33 U/mL thrombin, 0.12% dye final concentrations using a custom polyoxymethylene (POM) mold. Due to the hydrophobic nature of the mold, the fibrils along the surface appear to align more uniformly. Gels made with PBS had a wavy texture to the surface with irregular appearance of craters and mounds across the surface. Gels made with TB and EB appeared more uniform in nature FIG. 11. Representative transmission electron microscopy (TEM) photomicrographs of cross-sectional fibrin gels made of 40 mg/mL fibrinogen, 33 U/mL thrombin, 0.12% dye final concentrations using a custom polyoxymethylene (POM) mold. Though the surfaces appeared more similar between gels made with PBS, TB or EB, the inner volume shows a marked difference. Overall, it appears the gels made with TB and EB have much higher cross-linking, more uniform and thinner fibril size, and more uniform spread of fibrils compared to those made with PBS.

Fibrin gels made with TB and EB appeared to have a similar SEM morphology (FIG. 10). Fibrils are aligned parallel to the top surface plane with crater-like voids appearing fairly heterogeneously across the surface. At higher magnification, individual fibrils can be seen within the bulk volume of the gel.

Figure 11:
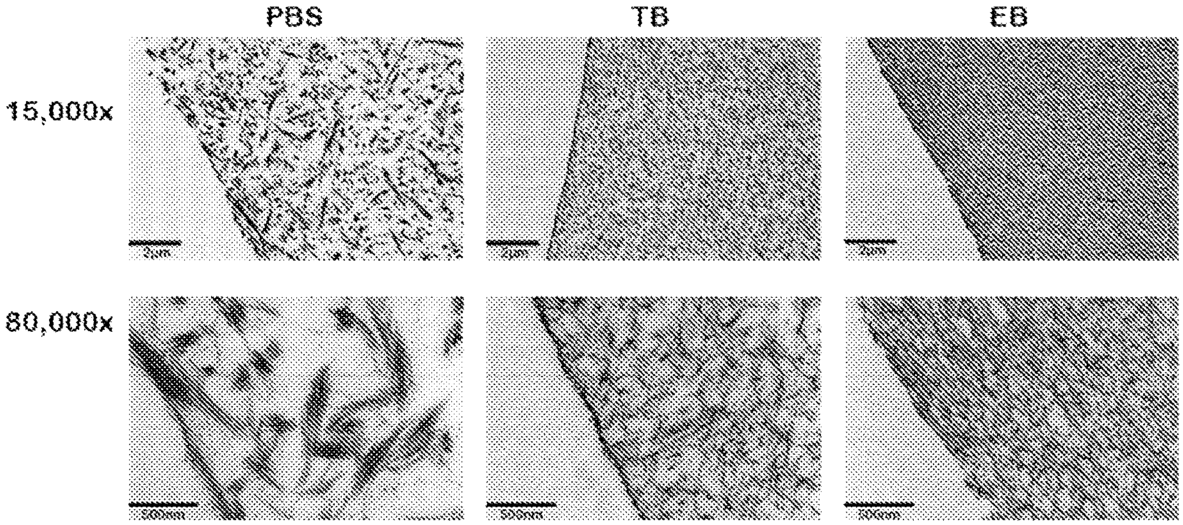

TEM was then performed to visualize the cross section of the fibrin gels. TEM images of the three conditions showed remarkable differences between gels made with PBS versus with TB or EB (FIG. 11). The PBS fibrin gel appears to have larger mesh spaces, with a large range of fibril diameters and orientation. Many fibrils with diameters in the range of 100-200 nm are present. The TB fibrin gels appear to be far more uniform in fibril diameter, fibril length, fibril density, and cross-linking density. Fibril diameters appear much smaller than those in the PBS gels, with the largest appearing in the range of 50-75 nm. The EB fibril gels appear similar to the TB fibrin gels with a more uniform morphology across the cross-section. In the EB fibrin gels, the mesh size appears to be smaller than that of the TB fibrin gel. In the EB fibrin gels it is difficult to discern individual fibrils, suggesting smaller fibril diameters and more cross-linking density. In EB fibrin gels, the largest diameters are in the range of 40-60 nm. The edges of all three gels appear to be very dark, suggesting an increased packing density, re-affirming the findings of the SEM images. These data conclude that TB and EB alter the microstructure of fibrin gels to create a more uniform fibril size and crosslink density.

Fibrin Gel Degradation Kinetics

One reason to utilize fibrin gels as scaffolds for cell transplantation is their attractive degradation properties. For example, fibrin gels implanted in the subretinal space of a pig eye can degrade safely within 8 weeks (see, e.g., Gandhi et al., *PLoS ONE,* 15:e0227641 (2020)). Because of this finding, it was evaluated whether TB or EB would alter the degradation kinetics of the gel in vitro.

Figure 12A:
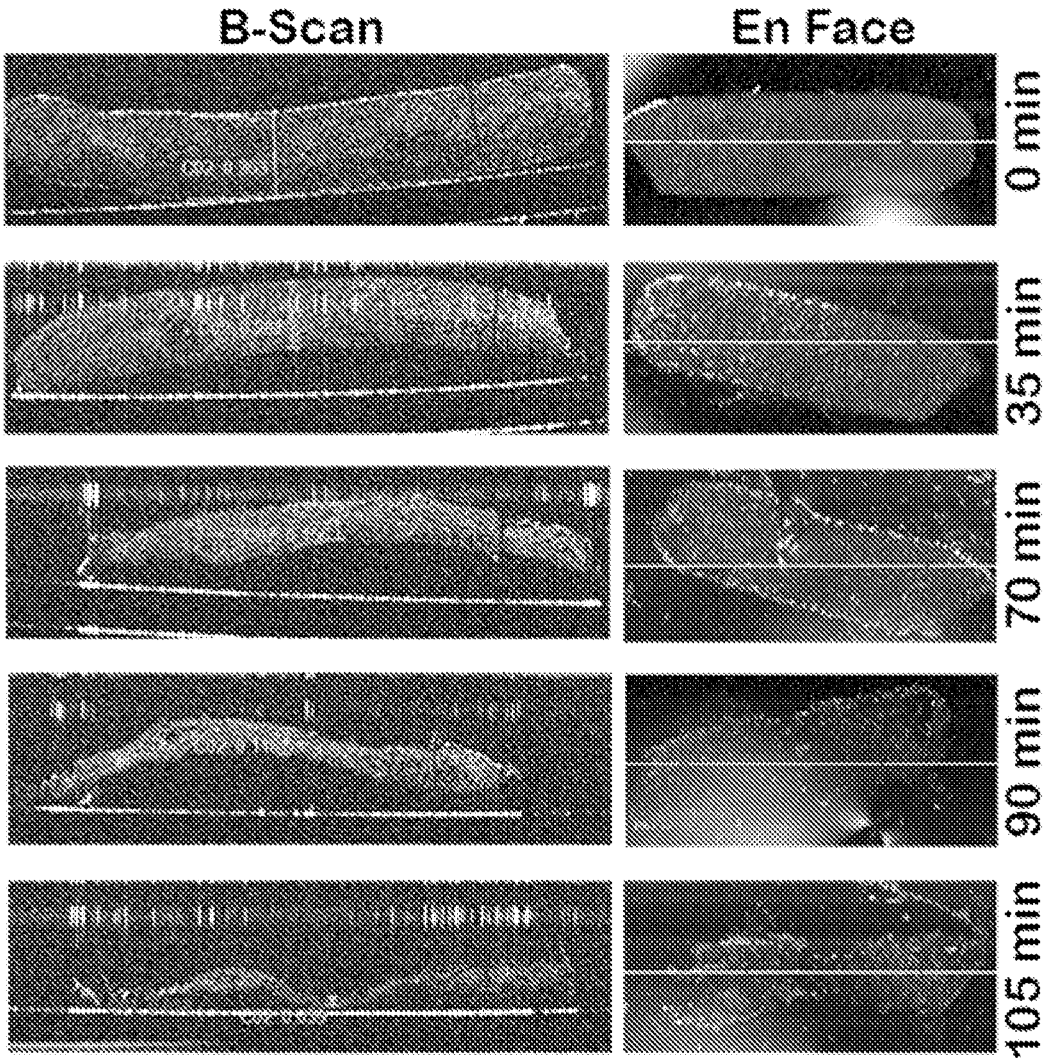
FIGS. 12A-12C. Evaluation of degradation of fibrin gels made with PBS, TB or EB.

Fibrin gels produced using PBS, TB, or EB with a geometry of 1.5 mm wide×5.0 mm long×0.2 mm thick were generated. Gels were hydrated in PBS prior to incubation in a solution of tissue plasminogen activator (tPA) and plasminogen (P) at 37° C. Optical Coherence Tomography (OCT) was used to image the gels over time to visualize the cross-sectional thickness (FIG. 12A). Over time, the thickness of the gel appeared to decrease. As the thickness decreased, the gel appeared to curve slightly. Surface degradation appeared to be non-uniform with varying levels of degradation at different points along the surface. No qualitative differences appeared in the OCT imaging of the three groups, with the except that the TB and EB appeared to have more uniform degradation in any given cross-sectional plane than PBS.

Figure 12B:
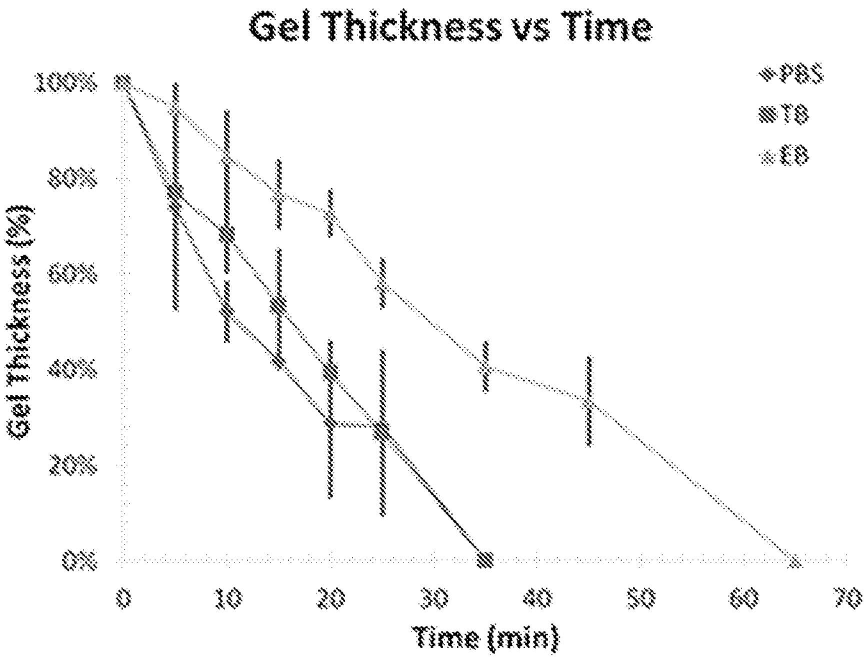
Figure 12C:
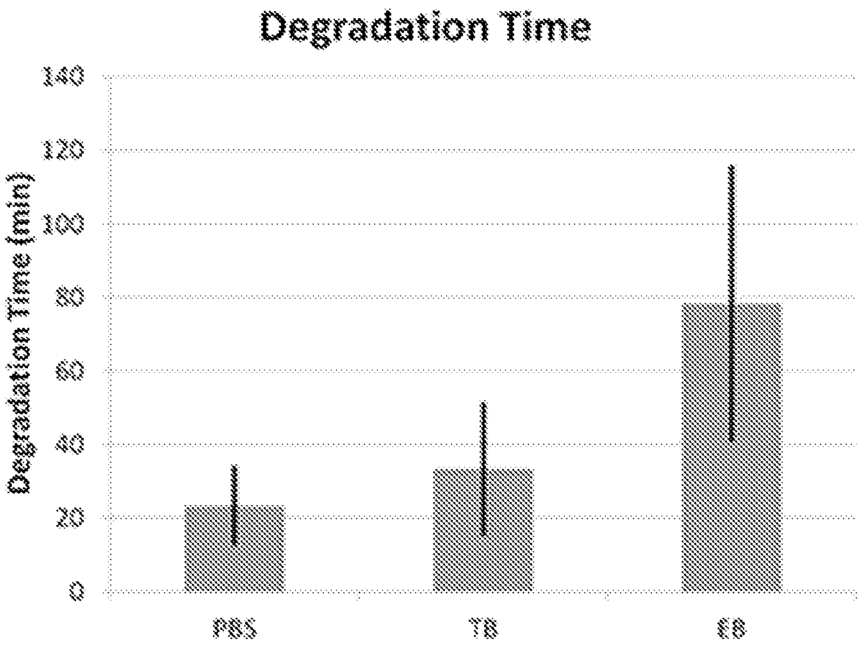
Figure 13A:
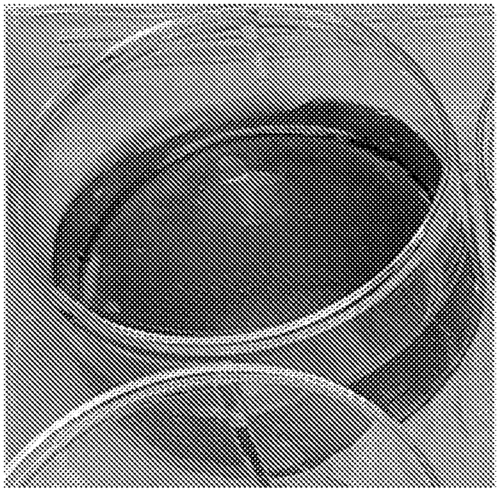
FIGS. 13A-13D.
Figure 13B:
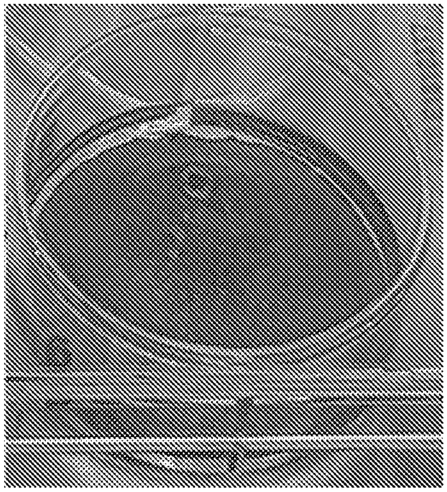
Figure 13C:
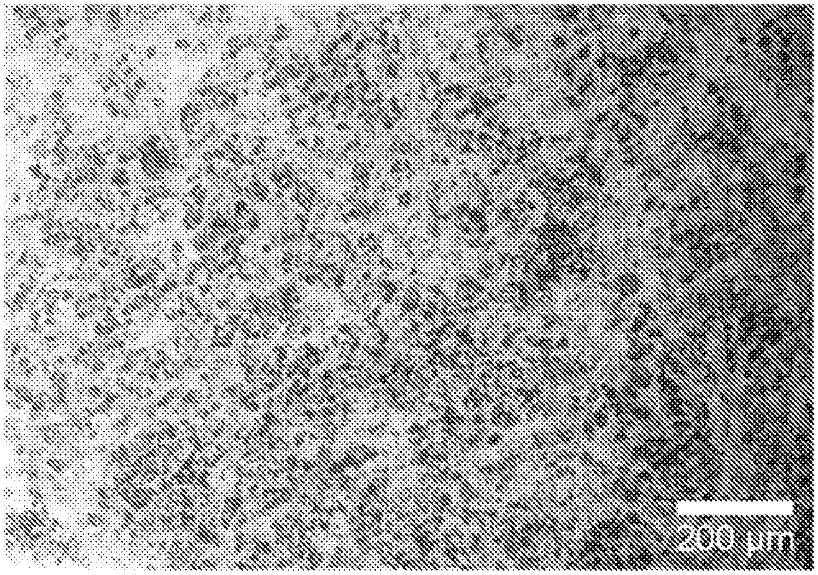
Figure 13D:
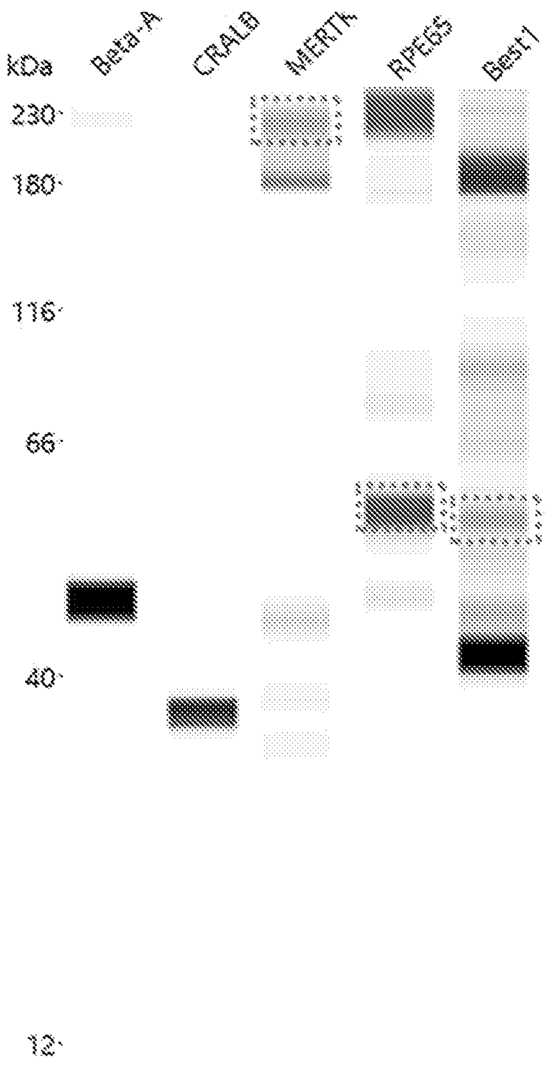

Quantitatively, the EB fibrin gels appeared to have a slower degradation than the TB and PBS gels (FIG. 12B). Over time, the remaining gel thickness appears to be mostly linear for all three groups. For the PBS, TB and EB gels, the degradation time was 23±10, 33±18, and 78±37 minutes, respectively (FIG. 12C). Although it appears the EB gels have a higher degradation time, the result was not statistically significant (n=3, p=0.068).

Together these results demonstrate that TB and EB can increase the gelation time of fibrin hydrogels without negatively altering the final polymerization time or shear modulus. For example, TB and EB can alter the microstructure of the fibrin gel to generate smaller, more uniform fibrils with increased cross-link density. As such, addition of TB and EB to fibrin gelation solutions can improve the handling time of fibrin manufacture, enabling alternative means to generate high mechanical strength fibrin gels for cell scaffolding applications at commercial scale.

Example 2: Methods for Manufacturing of Fibrin Hydrogel Scaffold Slide Plates Fibrin hydrogels can be used for regenerative medicine applications due to their biocompatibility and biodegradable properties. This Example describes an exemplary protocol for the generation and sealing of fibrin gel slides.

| Reagent |
| --- |
| Evicel 2 mL Kit |
| PBS, Ca Mg free |
| Trypan Blue, 4% Solution |
| Tranexamic Acid |

| Supply |
| --- |
| 200 μm slides |
| Sterile Gauze Square, 4" × 4" |
| 18 ga Needle |
| 11 to 1 kit Nordson |
| Nordson Static Mixer |
| 4 well rectangular plates |
| 1/16" luer lok connector |
| 1/16" ID tygon tubing, 1 cm long |
| 1 mL Pipette Tips |
| Sterile Plate Sealer Film |
| Sterile cleanroom tape |
| Plate Sealer Roller |
| Sterile Water (for water bath) |
| Sterile 6" × 8" Ziploc ® Bags |
| Sterile 10" × 12" Ziploc ® Bags |

| Equipment |
| --- |
| Biological Safety Cabinet |
| Incubator |
| Refrigerator |
| 37° C. Water Bath |
| 1 mL Pipettor |
| Pipet-Aid |
| Aluminum Slide Holder with Cover Plate and 12 screws |

| Processing Steps |
| --- |
| 1. Print a label for each plate plus 2 sample labels with the following information: |
| 2. Place thrombin and fibrinogen vials (1 kit for 5 slides) in a sterile Ziploc ®bag and seal. Place in the 37° C. water bath and submerge bag. Thaw for 1-10 minutes. Remove vials from bag, wipe vials with sterile IPA wipes. Discard the vials if they do not thaw within 10 minutes. |
| 3. Spray and wipe the inside of the biological safety cabinet with 70% IPA. Open consumable materials and aseptically set up processing field. |
| 4. Inspect vials for compromised seal and precipitate formation. Discard if noticed. |
| 5. Pipette 1 mL of Trypan blue solution into a 1.5 mL tube. Repeat for a total of 2 tubes per kit/holder. |
| 6. Set up plate holder with 5 slides. Single sprue hole on slide should face up and away from the aluminum. Attach cover plate and screw in 12 screws so that it is finger tight. |
| 7. Attach 18 ga needle to 1 mL syringe and use to collect 0.6 mL of thrombin solution. Avoid bubbles. Throw away additional vials of thrombin. |
| 8. Collect 0.4 mL of Trypan Blue solution into 1 mL syringe with thrombin. Invert syringe a few times to mix so color is homogenous. |
| 9. Attach 18 ga needle to the 11 mL syringe and collect all 2 mL of BAC2 solution from each vial. Avoid introducing bubbles into the syringe by preventing aspiration of air from each vial. |
| 10. Collect 0.75 mL of trypan blue solution into 11 mL syringe with BAC2. Invert syringe a few times to mix so color is homogeneous. |
| 11. Clip on 11 mL and 1 mL syringe to holder. Screw on Static mixer so that it is finger tight. |
| 12. Attach 1/16" fitting to luer lok connector with 1/16" silicone tubing. |
| 13. Line up the tubing to the sprue hole and push down with sufficient weight to seal around sprue hole. Dispense by plunging down on the syringe holder until the surface is filled and the air vents on the bottom are filled. Repeat for remaining 4 slides on the holder, working quickly. |
| 14. Repeat for additional holder if necessary. |
| 15. Place holder into sterile ziplok bag and seal. |
| 16. For each holder, use new kits (steps 6-15). |
| 17. 1 Evicel kit should produce up to 5 slides. |
| 18. Incubate all holders at 37° C. in incubator for 2-3 hours. |
| 19. Remove holders from incubator. Remove the cover plate carefully from each well, using a spatula bar if necessary. If the gel sticks to the cover plate and lifts off of the slide, discard the slide. |
| 20. Place a slide in a 4-well rectangular plate. Add 6 mL PBS to each slide/well. Swirl plate gently 3-10× to remove air bubbles. Allow the PBS to re-hydrate the fibrin gels for 15-30 minutes at room temperature in the biosafety cabinet. |
| 21. Aspirate PBS and fill each well with 10-12 mL of PBS, until well is 80-95% filled. |
| 22. Seal wells with plate sealer tape. Ensure it is sealed using the roller if necessary. |
| 23. Re-attach plate lid. Use sterile cleanroom tape to seal the lid to the plate. |

-continued

| Processing Steps |
| --- |
| 24. Affix label to each plate lid. |
| 25. Triple bag each plate using the sterile Ziploc ® bags. |
| 26. Retain 1 plate at room temperature for degradation testing. The remaining plates are routed for OCT imaging as per QC1, Optical Coherence Tomography Imaging procedure. |
| 27. Discard all solutions in biohazard waste. |

Example 3: Methods for Packaging of Fibrin Hydrogel Scaffold Plates

This Example describes a scaled method to manufacture fibrin hydrogels provided herein to have a more stable shelf-life and to make transport of the slide plates easier.

Fibrin hydrogels were manufactured within a slide plate as per example 2. A shield plate was snapped onto each slide plate to protect the top surface of the gel from damage. Sufficient clearance was provided to prevent contact of the shield plate and gel surface and to allow for liquid to keep the gel hydrated. A 3"×5" pre-sterilized foil pouch was filled with 5 mL of PBS with 2.5 mg/mL tranexamic acid. The slide plate with the shield plate was placed within the foil to fully submerge in the liquid. The foil pouch was heat sealed. The sealed product was then stored at various temperatures (ranging from 4° C. to 37° C.). The packaged product was then used at various time points to test shelf life.

This procedure can be performed using current Good Manufacturing Practices (cGMP). Sterility of the final packaged product can be maintained by performing the packaging step aseptically within a biosafety cabinet.

Example 4: Exemplary Embodiments

Embodiment 1. A fibrin hydrogel comprising (a) a fibrinogen polypeptide; (b) a thrombin polypeptide; and (c) Trypan Blue or an isomer thereof.

Embodiment 2. The fibrin hydrogel of embodiment 1, wherein said fibrin hydrogel comprises said Trypan Blue.

Embodiment 3. The fibrin hydrogel of embodiment 1, wherein said fibrin hydrogel comprises said isomer.

Embodiment 4. The fibrin hydrogel of any one of embodiments 1-3, wherein said fibrin hydrogel comprises from about 10 mg/mL to about 60 mg/mL of said fibrinogen polypeptide.

Embodiment 5. The fibrin hydrogel of embodiment 4, wherein said fibrin hydrogel comprises 40 mg/mL of said fibrinogen polypeptide.

Embodiment 6. The fibrin hydrogel of any one of embodiments 1-3, wherein said fibrin hydrogel comprises from about 0.1 U/mL to about 1200 U/mL of said thrombin polypeptide.

Embodiment 7. The fibrin hydrogel of embodiment 6, wherein said fibrin hydrogel comprises about 33 U/mL of said thrombin polypeptide.

Embodiment 8. The fibrin hydrogel of any one of embodiments 1-3, wherein said fibrin hydrogel comprises from about 0.0001% (w/w) to about 0.5% (w/w) of said Trypan Blue.

Embodiment 9. The fibrin hydrogel of embodiment 8, wherein said fibrin hydrogel comprises about 0.15% (w/w) of said Trypan Blue.

Embodiment 10. The fibrin hydrogel of any one of embodiments 1-9, wherein the polymerization time of said fibrin hydrogel is from about 2 seconds to about 1200 seconds.

Embodiment 11. The fibrin hydrogel of any one of embodiments 1-9, wherein said fibrin hydrogel comprises fibrils having a diameter of from about 1 nanometer (nm) to about 400 nm.

Embodiment 12. The fibrin hydrogel of any one of embodiments 1-9, wherein said fibrin hydrogel comprises fibrils having a crosslinking density of from about 1 crosslink/$\mu m^2$ to about 5,000 crosslinks/$\mu m^2$.

Embodiment 13. The fibrin hydrogel of any one of embodiments 1-9, wherein said fibrin hydrogel comprises a shear modulus of from about 1900 Pa to about 2420 Pa.

Embodiment 14. The fibrin hydrogel of any one of embodiments 1-9, wherein the surface area of said fibrin hydrogel is from about 0.05 $cm^2$ to about 300 $cm^2$.

Embodiment 15. The fibrin hydrogel of any one of embodiments 1-9, wherein the thickness of said fibrin hydrogel is from about 0.1 μm to about 1,000 μm.

Embodiment 16. The fibrin hydrogel of any one of embodiments 1-9, wherein said fibrin hydrogel is made by injection molding.

Embodiment 17. A fibrin hydrogel comprising (a) a fibrinogen polypeptide; (b) a thrombin polypeptide; and (c) Evans Blue or an isomer thereof.

Embodiment 18. The fibrin hydrogel of embodiment 17, wherein said fibrin hydrogel comprises said Evans Blue.

Embodiment 19. The fibrin hydrogel of embodiment 17, wherein said fibrin hydrogel comprises said isomer.

Embodiment 20. The fibrin hydrogel of any one of embodiments 17-19, wherein said fibrin hydrogel comprises from about 10 mg/mL to about 60 mg/mL of said fibrinogen polypeptide.

Embodiment 21. The fibrin hydrogel of embodiment 17, wherein said fibrin hydrogel comprises 40 mg/mL of said fibrinogen polypeptide.

Embodiment 22. The fibrin hydrogel of any one of embodiments 17-19, wherein said fibrin hydrogel comprises from about 0.1 U/mL to about 1200 U/mL of said thrombin polypeptide.

Embodiment 23. The fibrin hydrogel of embodiment 22, wherein said fibrin hydrogel comprises about 33 U/mL of said thrombin polypeptide.

Embodiment 24. The fibrin hydrogel of any one of embodiments 17-22, wherein said fibrin hydrogel comprises from about 0.0001% (w/w) to about 0.5% (w/w) of said Evans Blue.

Embodiment 25. The fibrin hydrogel of embodiment 24, wherein said fibrin hydrogel comprises about 0.15% (w/w) of said Evans Blue.

Embodiment 26. The fibrin hydrogel of any one of embodiments 17-25, wherein the polymerization time of said fibrin hydrogel is from about 2 seconds to about 1200 seconds.

Embodiment 27. The fibrin hydrogel of any one of embodiments 17-25, wherein said fibrin hydrogel comprises fibrils having a diameter of from about 1 nanometer (nm) to about 400 nm.

Embodiment 28. The fibrin hydrogel of any one of embodiments 17-25, wherein said fibrin hydrogel comprises fibrils having a crosslinking density of from about 1 crosslink/μm$^2$ to about 5,000 crosslinks/μm$^2$.

Embodiment 29. The fibrin hydrogel of any one of embodiments 17-25, wherein said fibrin hydrogel comprises a shear modulus of from about 1600 Pa to about 2520 Pa.

Embodiment 30. The fibrin hydrogel of any one of embodiments 17-25, wherein a surface area of said fibrin hydrogel is from about 0.05 cm$^2$ to about 300 cm$^2$.

Embodiment 31. The fibrin hydrogel of any one of embodiments 17-25, wherein a thickness of said fibrin hydrogel is from about 0.1 μm to about 1,000 μm.

Embodiment 32. The fibrin hydrogel of any one of embodiments 17-25, wherein said fibrin hydrogel is made by injection molding.

Embodiment 33. A fibrin hydrogel comprising (a) greater than about 30 mg/mL of a fibrinogen polypeptide, and (b) a thrombin polypeptide; wherein said fibrin hydrogel comprises a shear modulus of from about 1900 Pa to about 2420 Pa.

Embodiment 34. The fibrin hydrogel of embodiment 33, wherein said fibrin hydrogel comprises from about 30 mg/mL to about 60 mg/mL of said fibrinogen polypeptide.

Embodiment 35. The fibrin hydrogel of embodiment 34, wherein said fibrin hydrogel comprises 40 mg/mL of said fibrinogen polypeptide.

Embodiment 36. The fibrin hydrogel of any one of embodiments 33-35, wherein said fibrin hydrogel comprises from about 0.1 U/mL to about 1200 U/mL of said thrombin polypeptide.

Embodiment 37. The fibrin hydrogel of embodiment 36, wherein said fibrin hydrogel comprises about 33 U/mL of said thrombin polypeptide.

Embodiment 38. The fibrin hydrogel of any one of embodiments 33-35, wherein said fibrin hydrogel comprises Trypan Blue or an isomer thereof.

Embodiment 39. The fibrin hydrogel of embodiment 38, wherein said fibrin hydrogel comprises from about 0.0001% (w/w) to about 0.5% (w/w) of said Trypan Blue or said isomer.

Embodiment 40. The fibrin hydrogel of any one of embodiments 33-37, wherein said fibrin hydrogel comprises Evans Blue or an isomer thereof.

Embodiment 41. The fibrin hydrogel of embodiment 40, wherein said fibrin hydrogel comprises from about 0.0001% (w/w) to about 0.5% (w/w) of said Evans Blue or said isomer.

Embodiment 42. The fibrin hydrogel of any one of embodiments 33-41, wherein the polymerization time of said fibrin hydrogel is from about 2 seconds to about 1200 seconds.

Embodiment 43. The fibrin hydrogel of any one of embodiments 33-41, wherein said fibrin hydrogel comprises fibrils having a diameter of from about 1 nanometer (nm) to about 400 nm.

Embodiment 44. The fibrin hydrogel of any one of embodiments 33-41, wherein said fibrin hydrogel comprises fibrils having a crosslinking density of from about 1 crosslink/μm$^2$ to about 5,000 crosslinks/μm$^2$.

Embodiment 45. The fibrin hydrogel of any one of embodiments 33-41, wherein the surface area of said fibrin hydrogel is from about 0.05 cm$^2$ to about 300 cm$^2$.

Embodiment 46. The fibrin hydrogel of any one of embodiments 33-41, wherein the thickness of said fibrin hydrogel is from about 0.1 μm to about 1,000 μm.

Embodiment 47. The fibrin hydrogel of any one of embodiments 33-41, wherein said fibrin hydrogel is made by injection molding.

Embodiment 48. A fibrin hydrogel comprising (a) greater than about 30 mg/mL of a fibrinogen polypeptide, and (b) a thrombin polypeptide; wherein the polymerization time of said fibrin hydrogel is from about 2 seconds to about 1200 seconds.

Embodiment 49. The fibrin hydrogel of embodiment 48, wherein said fibrin hydrogel comprises from about 30 mg/mL to about 60 mg/mL of said fibrinogen polypeptide.

Embodiment 50. The fibrin hydrogel of embodiment 49, wherein said fibrin hydrogel comprises 40 mg/mL of said fibrinogen polypeptide.

Embodiment 51. The fibrin hydrogel of any one of embodiments 48-50, wherein said fibrin hydrogel comprises from about 0.1 U/mL to about 1200 U/mL of said thrombin polypeptide.

Embodiment 52. The fibrin hydrogel of embodiment 51, wherein said fibrin hydrogel comprises about 33 U/mL of said thrombin polypeptide.

Embodiment 53. The fibrin hydrogel of any one of embodiments 48-52, wherein said fibrin hydrogel comprises Trypan Blue or an isomer thereof.

Embodiment 54. The fibrin hydrogel of embodiment 53, wherein said fibrin hydrogel comprises from about 0.0001% (w/w) to about 0.5% (w/w) of said Trypan Blue or said isomer.

Embodiment 55. The fibrin hydrogel of any one of embodiments 48-52, wherein said fibrin hydrogel comprises Evans Blue or an isomer thereof.

Embodiment 56. The fibrin hydrogel of embodiment 55, wherein said fibrin hydrogel comprises from about 0.0001% (w/w) to about 0.5% (w/w) of said Evans Blue or said isomer.

Embodiment 57. The fibrin hydrogel of any one of embodiments 48-56, wherein said fibrin hydrogel comprises a shear modulus of from about 1900 Pa to about 2420 Pa.

Embodiment 58. The fibrin hydrogel of any one of embodiments 48-56, wherein said fibrin hydrogel comprises fibrils having a diameter of from about 1 nanometer (nm) to about 400 nm.

Embodiment 59. The fibrin hydrogel of any one of embodiments 48-56, wherein said fibrin hydrogel comprises fibrils having a crosslinking density of from about 1 crosslink/μm$^2$ to about 5,000 crosslinks/μm$^2$.

Embodiment 60. The fibrin hydrogel of any one of embodiments 48-56, wherein the surface area of said fibrin hydrogel is from about 0.05 cm$^2$ to about 300 cm$^2$.

Embodiment 61. The fibrin hydrogel of any one of embodiments 48-56, wherein the thickness of said fibrin hydrogel is from about 0.1 μm to about 1,000 μm.

Embodiment 62. The fibrin hydrogel of any one of embodiments 48-56, wherein said fibrin hydrogel is made by injection molding.

Embodiment 63. A fibrin hydrogel comprising (a) a fibrinogen polypeptide; (b) a thrombin polypeptide; and (c) a compound of Formula (I):

(I)

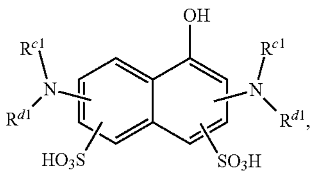

or a pharmaceutically acceptable salt thereof, wherein:

$R^{c1}$ and $R^{d1}$ are each independently selected from H and $C_{1-3}$ alkyl, or $R^{c1}$ and $R^{d1}$, together with the N atom to which they are attached form a group of formula:

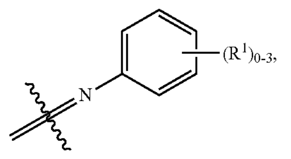

wherein each $R^1$ is independently selected from $C_{1-3}$ alkyl and $C_{1-3}$ alkoxy.

Embodiment 64. The fibrin hydrogel of embodiment 63, wherein $R^{c1}$ and $R^{d1}$ are each independently selected from H and $C_{1-3}$ alkyl.

Embodiment 65. The fibrin hydrogel of embodiment 63, wherein the compound of Formula (I) has formula:

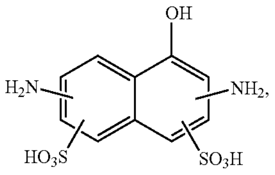

or a pharmaceutically acceptable salt thereof.

Embodiment 66. The fibrin hydrogel of embodiment 63, wherein $R^{c1}$ and $R^{d1}$, together with the N atom to which they are attached form a group of formula:

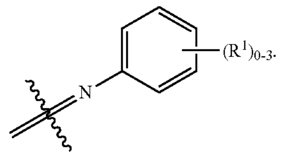

Embodiment 67. The fibrin hydrogel of embodiment 66, wherein $R^1$ is $C_{1-3}$ alkyl.

Embodiment 68. The fibrin hydrogel of embodiment 66, wherein $R^1$ is $C_{1-3}$ alkoxy.

Embodiment 69. The fibrin hydrogel of embodiment 66, wherein $R^{c1}$ and $R^{d1}$, together with the N atom to which they are attached form a group of formula:

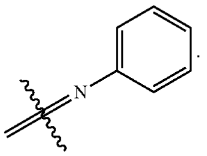

Embodiment 70. The fibrin hydrogel of embodiment 63, wherein the compound of Formula (I) has formula:

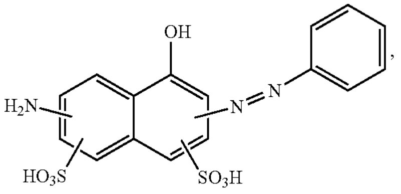

or a pharmaceutically acceptable salt thereof.

Embodiment 71. The fibrin hydrogel of embodiment 63, wherein the compound of Formula (I) has formula:

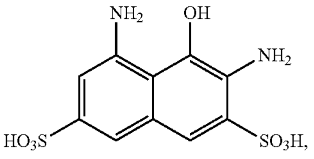 [SMILES: Nc1c(S(=O)(=O)O)cc2cc(S(=O)(=O)O)cc(N)c2c1O]

or a pharmaceutically acceptable salt thereof.

Embodiment 72. The fibrin hydrogel of embodiment 63, wherein the compound of Formula (I) has formula:

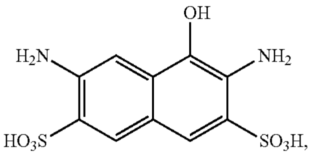 [SMILES: Nc1cc2c(O)c(N)c(S(=O)(=O)O)cc2cc1S(=O)(=O)O]

or a pharmaceutically acceptable salt thereof.

Embodiment 73. The fibrin hydrogel of embodiment 63, wherein the compound of Formula (I) has formula:

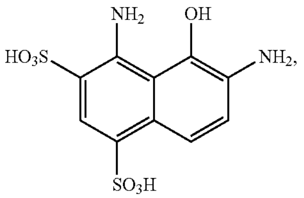

or a pharmaceutically acceptable salt thereof.

Embodiment 74. The fibrin hydrogel of any one of embodiments 63-73, wherein said fibrin hydrogel comprises from about 10 mg/mL to about 60 mg/mL of said fibrinogen polypeptide.

Embodiment 75. The fibrin hydrogel of embodiment 74, wherein said fibrin hydrogel comprises 40 mg/mL of said fibrinogen polypeptide.

Embodiment 76. The fibrin hydrogel of any one of embodiments 63-73, wherein said fibrin hydrogel comprises from about 0.1 U/mL to about 1200 U/mL of said thrombin polypeptide.

Embodiment 77. The fibrin hydrogel of embodiment 76, wherein said fibrin hydrogel comprises about 33 U/mL of said thrombin polypeptide.

Embodiment 78. The fibrin hydrogel of any one of embodiments 63-77, wherein the polymerization time of said fibrin hydrogel is from about 2 seconds to about 1200 seconds.

Embodiment 79. The fibrin hydrogel of any one of embodiments 63-77, wherein said fibrin hydrogel comprises fibrils having a diameter of from about 1 nanometer (nm) to about 400 nm.

Embodiment 80. The fibrin hydrogel of any one of embodiments 63-77, wherein said fibrin hydrogel comprises fibrils having a crosslinking density of from about 1 crosslink/μm$^2$ to about 5,000 crosslinks/μm$^2$.

Embodiment 81. The fibrin hydrogel of any one of embodiments 63-77, wherein said fibrin hydrogel comprises a shear modulus of from about 1900 Pa to about 2420 Pa.

Embodiment 82. The fibrin hydrogel of any one of embodiments 63-77, wherein the surface area of said fibrin hydrogel is from about 0.05 cm$^2$ to about 300 cm$^2$.

Embodiment 83. The fibrin hydrogel of any one of embodiments 63-77, wherein the thickness of said fibrin hydrogel is from about 0.1 μm to about 1,000 μm.

Embodiment 84. The fibrin hydrogel of any one of embodiments 63-77, wherein said fibrin hydrogel is made by injection molding.

Embodiment 85. A fibrin hydrogel comprising (a) a fibrinogen polypeptide; (b) a thrombin polypeptide; and (c) a compound of Formula (II):

(II)

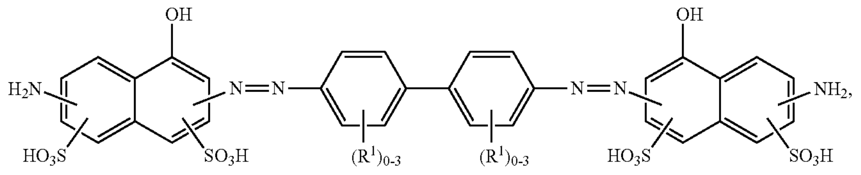

or a pharmaceutically acceptable salt thereof, wherein: each $R^1$ is independently selected from $C_{1-3}$ alkyl and $C_{1-3}$ alkoxy.

Embodiment 86. The fibrin hydrogel of embodiment 85, wherein the compound of Formula (II) has formula:

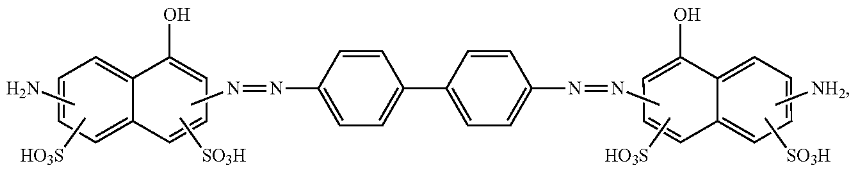

or a pharmaceutically acceptable salt thereof.

Embodiment 87. The fibrin hydrogel of embodiment 85, wherein the compound of Formula (II) has formula:

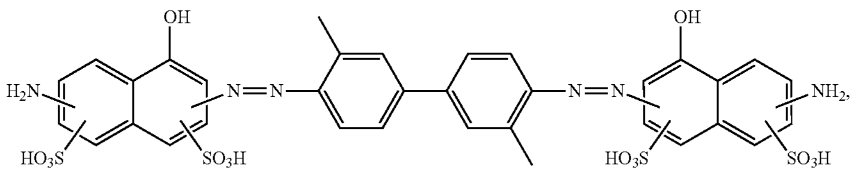

or a pharmaceutically acceptable salt thereof.

Embodiment 88. The fibrin hydrogel of embodiment 85, wherein the compound of Formula (II) has formula:

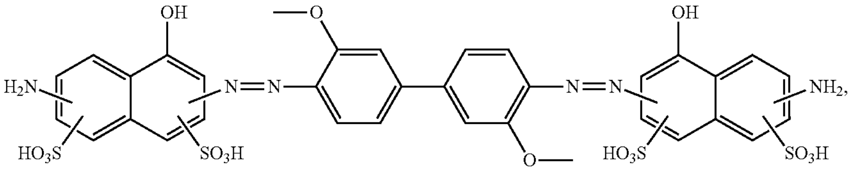

or a pharmaceutically acceptable salt thereof.

Embodiment 89. The fibrin hydrogel of embodiment 85, wherein the compound of Formula (II) has formula:

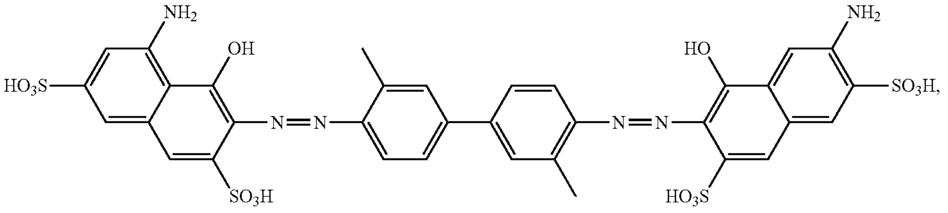 [SMILES: Cc1cc(-c2ccc(N=Nc3c(S(=O)(=O)O)cc4cc(S(=O)(=O)O)cc(N)c4c3O)c(C)c2)ccc1N=Nc1c(S(=O)(=O)O)cc2cc(S(=O)(=O)O)c(N)cc2c1O]

or a pharmaceutically acceptable salt thereof.

Embodiment 90. The fibrin hydrogel of embodiment 85, wherein the compound of Formula (II) has formula:

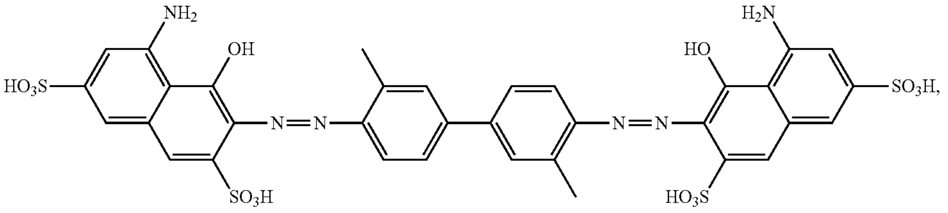 [SMILES: Cc1cc(-c2ccc(N=Nc3c(S(=O)(=O)O)cc4cc(S(=O)(=O)O)cc(N)c4c3O)c(C)c2)ccc1N=Nc1c(S(=O)(=O)O)cc2cc(S(=O)(=O)O)cc(N)c2c1O]

or a pharmaceutically acceptable salt thereof.

Embodiment 91. The fibrin hydrogel of embodiment 85, wherein the compound of Formula (II) has formula:

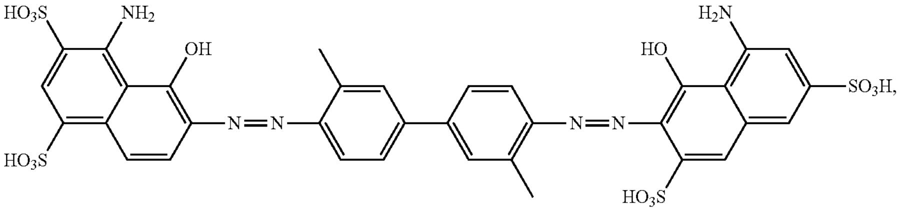 [SMILES: Cc1cc(-c2ccc(N=Nc3c(S(=O)(=O)O)cc4cc(S(=O)(=O)O)cc(N)c4c3O)c(C)c2)ccc1N=Nc1ccc2c(S(=O)(=O)O)cc(S(=O)(=O)O)c(N)c2c1O]

or a pharmaceutically acceptable salt thereof.

Embodiment 92. The fibrin hydrogel of embodiment 85, wherein the compound of Formula (II) has formula:

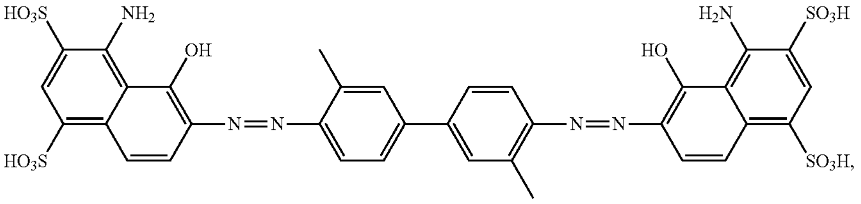 [SMILES: Cc1cc(-c2ccc(N=Nc3ccc4c(S(=O)(=O)O)cc(S(=O)(=O)O)c(N)c4c3O)c(C)c2)ccc1N=Nc1ccc2c(S(=O)(=O)O)cc(S(=O)(=O)O)c(N)c2c1O]

or a pharmaceutically acceptable salt thereof.

Embodiment 93. The fibrin hydrogel of any one of embodiments 85-92, wherein said fibrin hydrogel comprises from about 10 mg/mL to about 60 mg/mL of said fibrinogen polypeptide.

Embodiment 94. The fibrin hydrogel of embodiment 93, wherein said fibrin hydrogel comprises 40 mg/mL of said fibrinogen polypeptide.

Embodiment 95. The fibrin hydrogel of any one of embodiments 85-92, wherein said fibrin hydrogel comprises from about 0.1 U/mL to about 1200 U/mL of said thrombin polypeptide.

Embodiment 96. The fibrin hydrogel of embodiment 95, wherein said fibrin hydrogel comprises about 33 U/mL of said thrombin polypeptide.

Embodiment 97. The fibrin hydrogel of any one of embodiments 85-96, wherein the polymerization time of said fibrin hydrogel is from about 2 seconds to about 1200 seconds.

Embodiment 98. The fibrin hydrogel of any one of embodiments 85-96, wherein said fibrin hydrogel comprises fibrils having a diameter of from about 1 nanometer (nm) to about 400 nm.

Embodiment 99. The fibrin hydrogel of any one of embodiments 85-96, wherein said fibrin hydrogel comprises fibrils having a crosslinking density of from about 1 crosslink/$\mu m^2$ to about 5,000 crosslinks/$\mu m^2$.

Embodiment 100. The fibrin hydrogel of any one of embodiments 85-96, wherein said fibrin hydrogel comprises a shear modulus of from about 1600 Pa to about 2520 Pa.

Embodiment 101. The fibrin hydrogel of any one of embodiments 85-96, wherein a surface area of said fibrin hydrogel is from about 0.05 $cm^2$ to about 300 $cm^2$.

Embodiment 102. The fibrin hydrogel of any one of embodiments 85-96, wherein a thickness of said fibrin hydrogel is from about 0.1 μm to about 1,000 μm.

Embodiment 103. The fibrin hydrogel of any one of embodiments 85-96, wherein said fibrin hydrogel is made by injection molding.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fibrin hydrogel comprising (a) about 30 mg/mL to about 60 mg/mL of a fibrinogen polypeptide, (b) about 0.1 U/mL to about 50 U/mL of a thrombin polypeptide, and (c) from about 0.01% (w/v) to about 0.15% (w/v) Trypan Blue, Evans Blue, or an isomer thereof; wherein said fibrin hydrogel comprises a shear modulus of from about 1900 Pa to about 2420 Pa, and wherein said Trypan Blue, said Evans Blue, or said isomer thereof was added to a gelation mixture comprising said fibrinogen polypeptide and said thrombin polypeptide to form said fibrin hydrogel.

2. The fibrin hydrogel of claim 1, said fibrin hydrogel comprising from about 0.1% (w/v) to about 0.3% (w/v) of Trypan Blue, Evans Blue, or an isomer thereof.

3. The fibrin hydrogel of claim 1, wherein said fibrin hydrogel comprises about 40 mg/mL of said fibrinogen polypeptide.

4. The fibrin hydrogel of claim 1, wherein said fibrin hydrogel comprises about 33 U/mL of said thrombin polypeptide.

5. The fibrin hydrogel of claim 1, wherein said fibrin hydrogel comprises fibrils having a diameter of from about 1 nanometer (nm) to about 400 nm.

6. The fibrin hydrogel of claim 1, wherein said fibrin hydrogel comprises fibrils having a crosslinking density of from about 1 crosslink/$\mu m^2$ to about 5,000 crosslinks/$\mu m^2$.

7. A fibrin hydrogel comprising (a) about 30 mg/mL to about 60 mg/mL of a fibrinogen polypeptide, (b) about 0.1 U/mL to about 50 U/mL of a thrombin polypeptide, and (c) from about 0.01% (w/v) to about 0.15% (w/v) Trypan Blue, Evans Blue, or an isomer thereof; wherein the gelation time of said fibrin hydrogel is from about 100 seconds to about 250 seconds, and wherein said Trypan Blue, said Evans Blue, or said isomer thereof was added to a gelation mixture comprising said fibrinogen polypeptide and said thrombin polypeptide to form said fibrin hydrogel.

8. The fibrin hydrogel of claim 7, said fibrin hydrogel comprising from about 0.1% (w/v) to about 0.3% (w/v) of Trypan Blue, Evans Blue, or an isomer thereof.

9. The fibrin hydrogel of claim 7, wherein said fibrin hydrogel comprises about 40 mg/mL of said fibrinogen polypeptide.

10. The fibrin hydrogel of claim 7, wherein said fibrin hydrogel comprises about 33 U/mL of said thrombin polypeptide.

11. The fibrin hydrogel of claim 7, wherein said fibrin hydrogel comprises fibrils having a diameter of from about 1 nanometer (nm) to about 400 nm.

12. The fibrin hydrogel of claim 7, wherein said fibrin hydrogel comprises fibrils having a crosslinking density of from about 1 crosslink/$\mu m^2$ to about 5,000 crosslinks/$\mu m^2$.

* * * * *